United States Patent [19]

Schwartz et al.

[11] Patent Number: 5,455,262
[45] Date of Patent: Oct. 3, 1995

[54] MERCAPTOSULFIDE METALLOPROTEINASE INHIBITORS

[75] Inventors: Martin A. Schwartz, Tallahassee, Fla.; Harold Van Wart, Los Altos, Calif.

[73] Assignee: Florida State University, Tallahassee, Fla.

[21] Appl. No.: 132,414

[22] Filed: Oct. 6, 1993

[51] Int. Cl.$^6$ .......... A61K 31/40; A61K 31/165; C07D 209/32; C07C 233/05
[52] U.S. Cl. .......... 514/418; 514/399; 514/419; 514/601; 514/602; 514/604; 514/616; 514/618; 548/340.1; 548/485; 548/494; 548/495; 564/80; 564/81; 564/85; 564/153; 564/154
[58] Field of Search .......... 564/154, 153, 564/80, 81, 85, 154; 514/618, 19, 20, 601, 602, 604, 616, 418, 419, 399; 548/485, 494, 495, 340.1

[56] References Cited

U.S. PATENT DOCUMENTS

| | | | |
|---|---|---|---|
| 4,513,009 | 4/1985 | Roques et al. | 514/618 |
| 5,145,872 | 9/1992 | Chiarino et al. | 514/19 |

FOREIGN PATENT DOCUMENTS

| | | | |
|---|---|---|---|
| 0482539 | 4/1992 | European Pat. Off. | 514/19 |
| 0497192A2 | 8/1992 | European Pat. Off. | C07C 259/06 |
| WO90/05716 | 5/1990 | WIPO | C07C 259/06 |
| WO91/15507 | 10/1991 | WIPO | C07K 5/06 |
| WO92/21360 | 12/1992 | WIPO | A61K 37/00 |

OTHER PUBLICATIONS

Schwartz et. al., Matrix Supplement No. 1, pp. 309–310, 1992.
M. Brannstrom, et al., "Inhibitors of Mammalian Tissue Collagenase and Metalloproteinases Suppress Ovulation in the Perfused Rat Ovary", Endicrinology 122:1715–1721 (1988).
C. Librach, et al., "92–kD Type IV Collagenase Mediates Invasion of Human Cytotrophoblasts", J. Cell Biol. 113:437–449 (1991).
M. A. Schwartz, et al., "Synthetic Inhibibors of Bacterial and Mammalian Interstitial Collagenases", Prog. Medicinal Chem. 29:271–334 (1992).
L. M. Matrisian, "The Matrix–Degrading Metalloproteinases", Bioessays 14: 455–463 (1992).
H. Birkedal–Hansen, et al., "Matrix Metalloproteinases: A Review", Crit Revs. Oral Biol. Med. 4(2): 197–250 (1993).
J. M. Delaisse, et al., "The Effects of Inhibitors of Cysteine–Proteinases and Collagenase on the Resorptive Activity of Isolated Osteoclasts", Bone 8: 305–313 (1987).
J. M. Delaisse, et al., "A New Synthetic Inhibitor of Mammalian Tissue Collagenase Inhibits Bone Resorption in Culture", Biochem. Biophys. Res. Communs. 133: 483–490 (1985).

M. A. Moses, et al., "Inhibitors of Angiogenesis (Review)", Biotechnology 9: 630–634 (1991).
R. Langer, et al., "Control of tumor growth in animals by infusion of an angiogenesis inhibitor", Proc. Natl. Acad. Sci. USA 77: 4331–4335 (1980).
J. White, "Minocycline for Dystrophic Epidermolysis Bullosa", Lancet I: 966 (1988).
P. Humbert, et al., "Tetracyclines for Dystrophic Epidermolysis Bullosa", Lancet II: 277 (1989).
F. Burns, et al., "Inhibition of Alkali–Induced Corneal Ulceration and Perforation by a Thiol Peptide", Invest. Ophthalmol. Vis. Sci. 31:107–114 (1990).
A. Henney, et al., "Localization of stromelysin gene expression in atherosclerotic plaques by in situ hybridization", Proc. Natl. Acad. Sci. USA 88:8154–8158 (1991).
J. D'Arniento, et al., "Collagenase Expression in the Lungs of Transgenic Mice Causes Pulmonary Emphysema", Cell 71:955–961 (1992).

Primary Examiner—Shailendra Kumar
Attorney, Agent, or Firm—Senniger, Powers, Leavitt & Roedel

[57] ABSTRACT

Novel mercaptosulfide matrix metalloproteinase inhibitors of the Formula I,

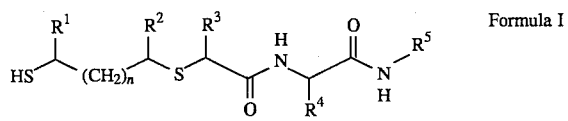

wherein:

n is 0 or 1;

$R^1$ is selected from the group consisting of hydrogen, lower alkyl, amino lower alkyl, carbamoyl lower alkyl, PhtN(lower alkyl), TsNH(lower alkyl); and $R^2$ is selected from the group consisting of hydrogen, lower alkyl, amino lower alkyl, carbamoyl lower alkyl, PhtN(lower alkyl), TsNH (lower alkyl); or $R^1$ and $R^2$ together are —$CH_2$—$CH_2$—$CH_2$—;

$R^3$ is selected from the group consisting of hydrogen, lower alkyl, aralkyl and heteroaralkyl; and $R^4$ is selected from the group consisting of hydrogen, lower alkyl, amino lower-alkyl, guanyl lower-alkyl, imidazoylalkyl, aralkyl and 2-indolylmethyl; and $R^5$ is selected from the group consisting of lower alkyl, aralkyl and —$CH(R^6)$—$C(O)NH_2$, wherein
$R^6$ is selected from the group consisting of hydrogen, lower-alkyl, amino lower-alkyl, guanyl lower-alkyl, imidazoylalkyl, hydroxymethyl, 1-hydroxyethyl, mercapto lower-alkyl, and methylthio lower-alkyl;
or
a pharmaceutically acceptable ester, ether or salt thereof, useful for treating diseases and disease conditions associated with matrix metalloproteinase modulation.

41 Claims, No Drawings

MERCAPTOSULFIDE METALLOPROTEINASE INHIBITORS

BACKGROUND OF THE INVENTION

1. Field of the Invention

This invention relates to pharmaceutically active mercaptosulfide derivatized peptides useful as inhibitors of the matrix metalloproteinase (MMP) family of enzymes for use in modulating physiological functions or treating diseases and disease conditions associated with MMP modulation, for example: arthritic diseases, such as osteoarthritis (OA), rheumatoid arthritis (RA), septic arthritis, soft tissue rheumatism, polychondritis and tendonitis; tumor invasion in certain cancers; periodontal diseases; corneal ulceration, e.g., that induced by alkali or other burns, by radiation, by vitamin E or retinoid deficiency; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; angiogenesis relating to tumor growth or to the neovascularization associated with diabetic retinopathy and macular degeneration; coronary thrombosis associated with atherosclerotic plaque rupture; and pulmonary emphysema. In addition to the compounds and their use, the invention also relates to their precursors, to their preparation and to pharmaceutical compositions using the compounds of the invention.

2. Background Information

The MMPs are a family of zinc-containing proteinases believed to be responsible for the metabolic turnover of protein components of the extracellular matrix of humans. At present there are at least eight known human MMP.

Various disease and disease conditions have been linked with the actions or presence of MMP, e.g., elevated levels of certain of these enzymes exists in joints of arthritic humans and animals and therefore have been linked to the degradation of the major components of articular cartilage and basement membranes. It is presently believed that the collective action of the MMP on extracellular matrix macromolecules is responsible for the destruction of connective tissue, however, the precise role of each enzyme in the process is not yet well understood. It has also been reported that certain MMP may be instrumental in mediating certain normal physiological functions that involve the breakdown or development of tissue.

It has been desired to selectively inhibit certain MMP enzymes, specifically those which modulate certain diseases, physiological conditions and disease conditions, in order that such conditions could be controlled.

It has been surprisingly discovered that a family of mercaptosulfide derivatized polypeptides are potent inhibitors of MMP, thereby affording a method of treating MMP-mediated diseases and disease conditions, and controlling MMP-mediated physiological functions.

SUMMARY OF THE INVENTION

Novel mercaptosulfide matrix metalloproteinase inhibitors of the Formula I,

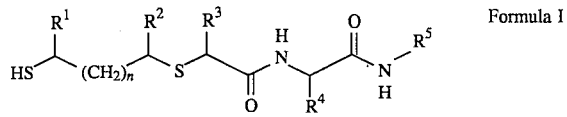

wherein:

n is 0 or 1;

$R^1$ is selected from the group consisting of hydrogen, lower alkyl, amino lower alkyl, carbamoyl lower alkyl, PhtN(lower alkyl), TsNH-(lower alkyl); and $R^2$ is selected from the group consisting of hydrogen, lower alkyl, amino lower alkyl, carbamoyl lower alkyl, PhtN(lower alkyl), TsNH-(lower alkyl); or $R^1$ and $R^2$ together are —CH$_2$—CH$_2$—CH$_2$—;

$R^3$ is selected from the group consisting of hydrogen, lower alkyl, aralkyl and heteroaralkyl; and $R^4$ is selected from the group consisting of hydrogen, lower alkyl, amino lower-alkyl, guanyl lower-alkyl, imidazoylalkyl, aralkyl and 2-indolylmethyl; and $R^5$ is selected from the group consisting of lower alkyl, aralkyl and —CH($R^6$)—C(O)NH$_2$, wherein $R^6$ is selected from the group consisting of hydrogen, lower-alkyl, amino lower-alkyl, guanyl lower-alkyl, imidazoylalkyl, hydroxymethyl, 1-hydroxyethyl, mercapto lower-alkyl, and methylthio lower-alkyl;

or a pharmaceutically acceptable ester, ether or salt thereof, useful for treating diseases and disease conditions associated with MMP modulation, e.g., arthritic diseases, such as osteoarthritis (OA), rheumatoid arthritis (RA), septic arthritis, soft tissue rheumatism, polychondritis and tendonitis; tumor invasion in certain cancers, periodontal diseases; corneal ulceration, e.g., that induced by alkali or other burns, by radiation, by vitamin E or retinoid deficiency; ulceration of the skin and gastrointestinal tract, and abnormal wound healing; post operative conditions, including colonic anastomosis; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; demyelinating diseases of the central and peripheral nervous systems, including syndromes in which myelin loss is the primary pathological event and those in which demyelination follows axonal atrophy, e.g., multiple sclerosis, angiogenesis relating to tumor growth on to the neovascularization associated with diabetic retinopathy and macular degeneration; and coronary thrombosis associated with atherosclerotic plaque rupture.

DETAILED DESCRIPTION

Definitions and General Parameters

The term "alkyl" refers to a branched or straight chain monovalent saturated aliphatic hydrocarbon radical of one to twenty carbon atoms.

The term "lower-alkyl" refers to a branched or straight chain monovalent alkyl radical of one to six carbon atoms. This term is further exemplified by such radicals as methyl, ethyl, propyl, isopropyl, butyl (e.g., isobutyl, t-butyl, or n-butyl), pentyl, and hexyl.

The term "aryl" refers to an aromatic monovalent carbocyclic radical, which can optionally be mono-, di-, tri- or tetra-substituted, independently, with lower alkyl (e.g., methylphenyl, ethylphenyl), lower-alkyoxy (e.g., 4-methoxyphenyl), hydroxy (e.g., 4-hydroxyphenyl) halo, carboxy, lower-alkoxycarbonyl, carbamoyl, mono- and dimethylcarbamoyl, lower-alkyl carbonyl (such as, methylcarbonyl and ethylcarbonyl), hydroxymethyl, amino, trifluoromethyl, cyano or nitro.

The term "aralkyl" refers to the group (aryl)-(lower-alkyl)-. For example, typical aralkyl groups are e.g., phenylmethyl (i.e., benzyl), phenylethyl, 4-hydroxyphenylmethyl, or 4-methoxyphenylmethyl.

The term "heteroaryl" refers to aromatic monovalent mono- or bi-carbocyclic radical having at least one heteroatom, i.e., nitrogen, oxygen or sulfur, which can optionally be mono- or di-substituted adjacent to the heteroatom, independently, with lower alkyl, halo, cyano, amino or trifluoromethyl. For example, typical heteroaryl groups with one or more nitrogen atoms are tetrazoyl, pyridyl (e.g., 4-pyridyl, 3-pyridyl, 2-pyridyl), 2-indolyl, 3-indolyl, pyridazinyl, quinolinyl, 2-quinolinyl, 3-quinolinyl, imidazolyl, isoquinolinyl, pyrazolyl, pyrazinyl, pyrimidinyl, pyridonyl or pyridazinonyl; typical oxygen heteroaryl radicals with oxygen atom are furanyl, or benzofuranyl; typical sulfur heteroaryl radicals are thienyl, and benzothiophenyl.

The term "heteroaralkyl" refers to the group (heteroaryl)-(lower alkyl). For example, typical heteroaralkyl groups are e.g., imidazoyl lower-alkyl, such as, 4-imidazolylmethyl, 3-imidazolylmethyl, 4-imidazoylethyl, or indolyl lower-alkyl, such as, 2-indolylmethyl, 3-indolylmethyl, The term "guanyl" refers to the moiety carbamimidoylamino

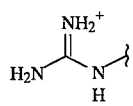

The term "PhtN" refers to

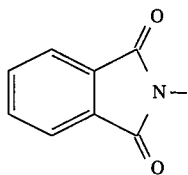

i.e., phthalimido moiety.

The term "PhtN ( lower alkyl )" refers to

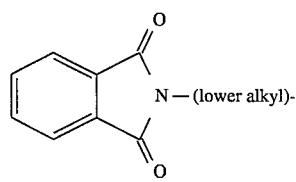

e.g., PhtNBu (i.e., 4-phthalimidobutyl) or PhtNEt (i.e., 2-phthalimidoethyl).

The term "PheNHMe" refers to

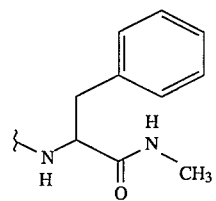

The term "TrpNHMe" refers to

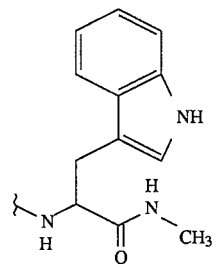

The term "Phe-Ala-OH" refers to

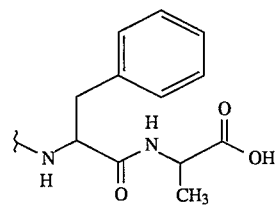

The term "TsNH-(lower alkyl)" refers to

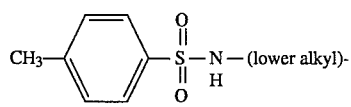

e.g., 4-(p-toluenesulfonamido)-butyl.

The term "blocking group" or "BG" refer to a chemical group which exhibits the following characteristics. The group must react selectively in good yield to give a blocked or protected substrate that is stable to the projected reactions; and the blocking group must be selectively removable in good yield by readily available, preferably nontoxic reagents that do not attack the functional group(s) generated in such projected reactions. For example, typical blocking groups are benzyloxycarbonyl, tert-butyldimethylsilyl, or benzyl [for additional blocking or protecting groups see "Protective Groups", J. F. W. McOmie, *Adv. Org. Chem.*, 3, 191 (1963) or "Protective Groups in Organic Synthesis", Theodora W. Greene and Peter G. M. Wilts, John Wiley & Sons, 2nd Edition, 1991] are used for protecting substrates containing the chemical moieties, such as 4-hydroxyphenylmethyl, 3-indolylmethyl, 4-aminobutyl, 3-guanylpropyl or 4-imidazoylmethyl.

The term "blocked" refers to a chemical moiety that has been treated with a blocking group.

The term "de-blocking" reagent refers to a reagent which is used to remove a blocking group, e.g., elemental Na and liquid ammonia for debenzylation of S-benzyl (Evans, D. A.; Mathre, D. J.; Scott, W. L. *J. Org. Chem.* 1985, 50, 1830–1835), 10% Pd/C with catalytic amount of cyclohexylamine and H$_2$ gas for removing CBz from imine moiety, or tetrabutylammonium fluoride hydrate for remove t-butyldimethylsilyl moiety.

"Enantiomers" are two stereoisomers whose molecules are non-superimposable mirror images of one another.

"Diastereoisomers" or "diastereomers" are stereoisomers with two or more centers of asymmetry and whose molecules are not mirror images of one another.

The term "racemic" means existing as a racemate, or as a 50—50 mixture of two enantiomers, also denoted by "dl" or "±".

The terms "D" and/or "L" refers to the absolute configuration at an asymmetric carbon of a molecule assigned according to experimental chemical correlation with that of the α-carbon of a modified or unmodified amino acid residue (using the absolute configuration of the α-carbon of D- or L-serine as the standard).

The designation "DL" indicates a mixture of the D and L stereoisomers or that diastereomers were separated but not identified.

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures. Specific illustrations of suitable separation and isolation procedures can be had by reference to the examples hereinbelow. However, other equivalent separation or isolation procedures can also be used.

Nomenclature

The following convention of abbreviations and nomenclature has been adopted and will be used to name the compounds of the present invention.

Common naturally occurring amino acids relating to the present invention are listed below in tables according to their radical type (e.g., aliphatic, aromatic, basic or substituted aliphatic).

|  | Radical | Abbreviation |
|---|---|---|
| Aliphatic Amino Acids | | |
| Glycine | H | Gly |
| Alanine | methyl | Ala |
| Val | 2-propyl | Val |
| Leucine | 2-methylpropyl | Leu |
| Isoleucine | 2-butyl | Ile |
| Aromatic Amino Acids | | |
| Phenylalanine | benzyl | Phe |
| Tyrosine | 4-hydroxyphenylmethyl | Tyr |
| Tryptophan | 3-indolylmethyl | Trp |
| Basic Amino Acids | | |
| Lysine | 4-aminobutyl | Lys |
| Arginine | 3-guanylpropyl | Arg |
| Histidine | 4-imidazoylmethyl | His |
| Substituted Amino Acids | | |
| Cysteine | thiolmethyl | Cys |
| Methionine | methylthioethyl | Met |
| Serine | hydroxymethyl | Ser |
| Threonine | 1-hydroxyethyl | Thr |

The abbreviation "Ac-" refers to the acetyl radical.

The abbreviation "Bn-" or "Bnz-" refers to the benzyl radical (i.e., phenylmethyl).

The abbreviation "AcS-" refers to the thiolacetyl radical.

The abbreviation "-OEt" refers the ethoxy radical.

The abbreviation "RS-" refers to a lower-alkyl sulfide radical.

The abbreviation "BnS-" refers to the benzylsulfide radical.

The abbreviation "TBS" refers to the tert-butyldimethylsilyl radical.

The abbreviation "Cbz" refers to the benzyloxycarbonyl radical, i.e.,

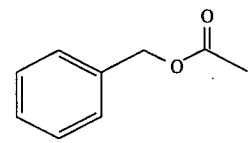

The abbreviation "(Phet)" refers to the modified amino acid with phenylethyl as the radical, i.e.,

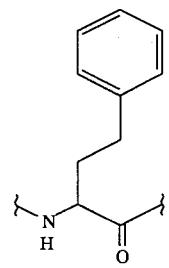

The abbreviation "(Tyr-OCH$_3$)" refers to the modified amino acid with 4-methoxyphenylmethyl as the radical, i.e.,

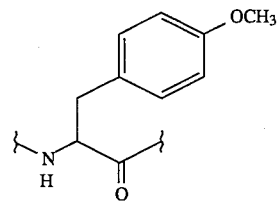

Certain naming conventions are accepted to represent the structure of modified peptides. For example, a modification of the C=O group of an amino acid residue is signified by the usual three-letter code for the residue followed by the formula of the group that has replaced the C=O, separated by a hyphen, all enclosed in parentheses, a modification of the NH group of a residue is analogously indicated by the three-letter code for the residue preceded by the formula of the group substituting for the NH, separated by a hyphen, all enclosed in parentheses, and the stereoconfiguration of the α-carbon of a residue is indicated by the letters L or D preceding the three-letter code for the residue. The absence of either letters, or the presence of both letters indicates a mixture of the L and D isomers, or that diastereomers were separated but not identified.

Some representative compounds are named in the following examples.

For example,

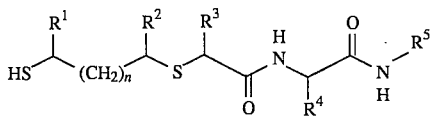

where n is 0, $R^1$ and $R^2$ are hydrogen, $R^3$ is 2-methylpropyl, $R^4$ is phenylmethyl, $R^5$ is —CH($R^6$)—C(O)NH$_2$ and $R^6$ is methyland the carbon that is the point of attachment for $R^3$ is in the D-configuration, is designated as HS(CH$_2$)$_2$—(S-D-Leu)-Phe-NHMe.

For example,

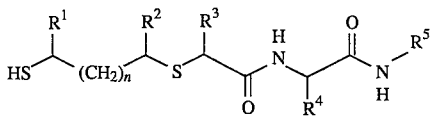

where n is 0, $R^1$ is methyl, $R^2$ is hydrogen, $R^3$ is 2-methylpropyl, $R^4$ is phenylmethyl, $R^5$ is —CH($R^6$)—C(O)NH$_2$ and $R^6$ is methyl, and the carbon that is the point of attachment for $R^3$ is in the D-configuration and the carbon that is the point of attachment for $R^1$ is in the S-configuration, is designated as HS(S)CHMeCH$_2$—(S-D-Leu)-Phe-NHMe.

For example,

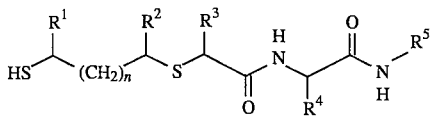

where n is 0, $R^1$ is hydrogen, $R^2$ is methyl, $R^3$ is 2-methylpropyl, $R^4$ is phenylmethyl, $R^5$ is —CH($R^6$)—C(O)NH$_2$ and $R^6$ is methyl, and the carbon that is the point of attachment for $R^3$ is in the D-configuration and the carbon that is the point of attachment for $R^1$ is in the R-configuration, is designated as HSCH$_2$(R)CHMe-(S-D-Leu)-Phe-NHMe.

For example,

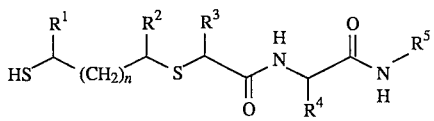

where n is 0, $R^1$ and $R^2$ are —CH$_2$—CH$_2$—CH$_2$—, $R^3$ is 2-methylpropyl, $R^4$ is phenylmethyl, $R^5$ is —CH($R^6$)—C(O)NH$_2$ and $R^6$ is methyl, and the carbon that is the point of attachment for $R^3$ is in the D-configuration, is designated as HS-(1,2-cyclopentyl)-(S-D-Leu)-Phe-NHMe.

For example,

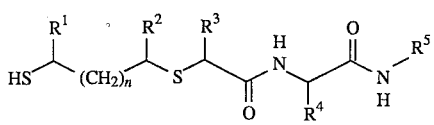

where n is 1, $R^1$ and $R^2$ are —CH$_2$—CH$_2$—CH$_2$—, $R^3$ is 2-methylpropyl, $R^4$ is phenylmethyl, $R^5$ is —CH($R^6$)—C(O)NH$_2$ and $R^6$ is methyl, and the carbon that is the point of attachment for $R^3$ is in the D-configuration, is designated as HS-(1,3-cyclohexyl)-(S-D-Leu)-Phe-NHMe.

Synthesis of the Compounds of Formula I

Reaction Scheme A describes the preparation of compounds of Formula I where $R^1$ and $R^2$ are the same substituent, and $R^3$, $R^4$, $R^5$, $R^6$ and $R^7$ are the same as described in the Summary of the Invention.

Reaction Scheme B describes the preparation of compounds of Formula I where $R^2$ is hydrogen, n is 0, and $R^1$, $R^3$, $R^4$, $R^5$, $R^6$ and $R^7$ are the same as described in the Summary of the Invention.

Reaction Scheme C describes the preparation of compounds of Formula I where $R^1$ is hydrogen, n is 0, and $R^2$, $R^3$, $R^4$, $R^5$, $R^6$ and $R^7$ are the same as described in the Summary of the Invention.

The compounds described in Reaction Schemes A, B and C may contain single or multiple chiral centers and therefore may exist as enantiomers or diastereomers. It should be understood that unless otherwise indicated, the compounds described in Reaction Schemes A, B and C are intended to represent enantiomeric and/or diastereomeric mixtures, either racemic or non-racemic. The scope of the subject invention herein is considered to encompass all stereoisomers of the subject compounds and mixtures thereof.

REACTION SCHEME A

Starting Materials

The compounds of Formula 1, i.e., amino acids (natural and modified) are commercially available from Aldrich Chemical Company or Sigma Chemical Company, or can be prepared following procedures known to those of ordinary skill in the art.

Preparation of Formula 2

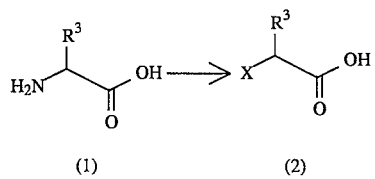

An amino acid or modified amino acid, i.e., a compound of Formula 1, is combined with about 3.5 molar equivalents of a halogen salt, such as, NaBr, KBr, NaCl, KCl, NaI, KI, preferably, KBr, and a strong acid, concentrated H$_2$SO$_4$ (about 0.2 mL/molar equivalent) in water at a temperature in the range of about –10° C. to 0° C., preferably about –4° C. To this solution is added about 1.5 molar equivalents of a nitrosating reagent, such as, NaNO$_2$ over a period of about 1 hour. After completion of the addition, the reaction mixture is stirred for an additional 1 hour. The solution is extracted with a nonpolar organic solvent, e.g., methylene chloride. The organic layer is washed, dried and evaporated to yield the desired 2-halo-optionally substituted carboxylic acid, i.e., a compound of Formula 2.

Preparation of Formula 4

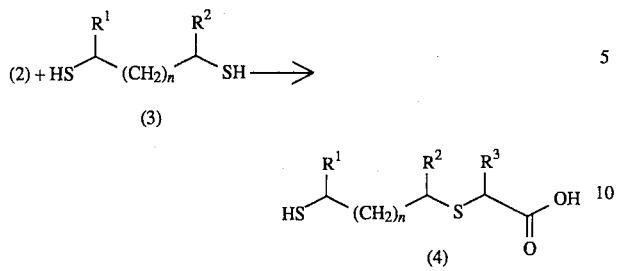

About 14 molar equivalents of an optionally substituted lower-alkyl dimercapto compound (i.e., a compound of Formula 3 where $R^1$ and $R^2$ are the same) is combined with about 2.4 molar equivalents of Na in an alcoholic solvent, such as, ethanol, with stirring at about room temperature under an inert atmosphere. After stirring for about 10 minutes, a solution of 2-halo-optionally substituted carboxylic acid, i.e., compound of Formula 2, in an alcoholic solvent, such as, ethanol, is added. The reaction mixture is stirred at about room temperature for a period of about 12 to 20 hours, preferably about 16 hours. The reaction solution is poured into water, acidified and extracted with a nonpolar organic solvent, e.g., methylene chloride. The organic layer is dried, and the solvent and remaining dimercapto starting material is removed by vacuum. The residue is purified by flash chromatography, e.g., 15% ethyl acetate in hexane, to yield the desired mercapto 2-optionally substituted lower-alkyl sulfide carboxylic acid, i.e., a compound of Formula 4.

Preparation of Formula 5

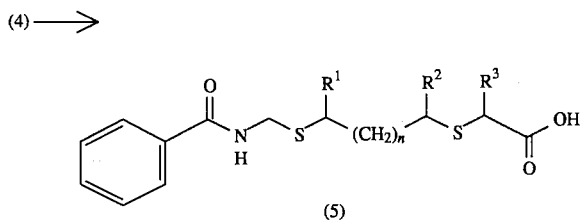

About 1 molar equivalent of a mercapto blocking agent, such as, benzamidomethanol (commercially available from Pfaltz and Bauer Chemical Companies) and a strong acid, such as, trifluoroacetic acid (about 2.3 mL/molar equivalent), is combined with a mercapto lower-alkyl thiocarboxylic acid, i.e., a compound of Formula 4, with stirring at a temperature in the range of about −10° C. to 10° C., preferably about 0° C. After completion of the addition, the mixture is stirred for about 1 hour. The acid and solvent are removed by vacuum, and the residue is purified by chromatography, e.g., silica gel to yield the desired blocked mercapto lower-alkyl thiocarboxylic acid residue, i.e., a compound of Formula 5.

Preparation of Formula 6

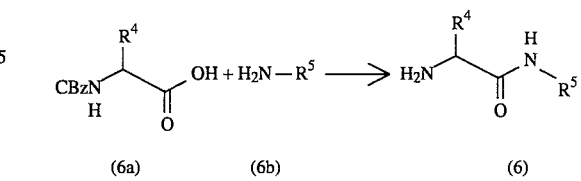

A compound of Formula 6 is formed by the following procedure, which is a modification of procedures reported in Bodanszky, M.; Bodanszky, A. *The Practice of Peptide Synthesis;* Springer-Verlag: New York, 1984; p 129–142. A compound of Formula 6a (where $R^4$ is hydrogen, lower-alkyl, blocked 4-aminobutyl, blocked 3-guanylpropyl, blocked 4-imidazoylmethyl, benzyl, blocked 4-hydroxyphenylmethyl, 3-indolylmethyl, 4-methoxyphenylmethyl or phenethyl) is combined with about 1 to 1.2 molar equivalents of N-hydroxysuccinimide, 1 to 1.2 molar equivalents of 1,3-dicyclohexylcarbodiimide and an anhydrous solvent (at about 1.2 mL/mmolar equivalent) such as tetrahydrofuran at a temperature in the range of about 0° C. to 10° C., preferably about 4° C. under an inert atmosphere for a period of about 13 to 39 hours, preferably about 26 hours. The resulting precipitate is removed by filtration. To the filtrate is added about 1.3 molar equivalents of a compound of Formula 6b dissolved in THF or in water, and if $R^5$ is —CH($R^6$)—CO$_2$H, 1.3 molar equivalents of a strong base such as sodium hydroxide in water is also added. The combined mixture is stirred at about room temperature for a period of about 12 to 24 hours, preferably about 18 hours. The solid residue is removed by filtration and the filtrate is diluted with saturated aqueous NaHCO$_3$ and is extracted with a non-polar solvent (e.g., CHCl$_3$). If $R^5$ is lower-alkyl or aralkyl, the organic layer is evaporated to give the crude protected amino acid amide. If $R^5$ is —CH($R^6$)—CO$_2$H, the aqueous layer is acidified and the resulting precipitate is collected, washed and dried to yield the crude protected dipeptide acid. The crude protected dipeptide acid is subjected again to the above procedure, using excess anhydrous ammonia in an anhydrous solvent such as tetrahydrofuran, to give the crude protected dipeptide amide.

The crude protected amino acid amide or crude protected dipeptide amide from this procedure is subjected to hydrogenolysis in methanol over 10% Pd/C. The product is purified by flash chromatography (e.g., ethyl acetate-methanol, 10:1) to afford a compound of Formula 6.

Preparation of Formula 7

(5) + (6) ⟶

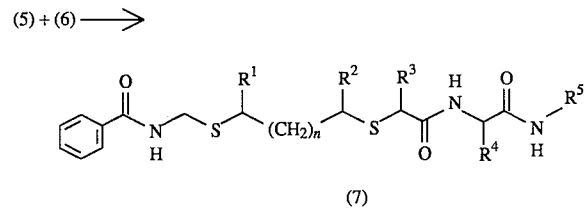

About 1 molar equivalent of an amino acid, modified amino acid or peptide fragment (with a free N-terminus), i.e., a compound of Formula 6, is combined with a blocked mercapto lower-alkyl thiocarboxylic acid, i.e., a compound of Formula 5, in a solvent, such as, 1,2-dimethoxyethane with stirring at a temperature in the range of about 0° C. to 10° C., preferably about 5° C. To this solution is added a peptide coupling reagent, such as, about 1.2 molar equivalents of 1-hydroxybenzotriazole and 1.2 molar equivalents of dicyclohexylcarbodiimide (DCC). The reaction mixture is stirred at a temperature in the range of about 0° C. to 10° C., preferably about 5° C. for a period of about 2 to 6 hours, preferably about 4 hours, and then for a period of about 12 to 24 hours, preferably about 18 hours, at about room temperature. The resulting solid is filtered and washed with a nonpolar organic solvent, e.g., methylene chloride. The filtrate is combined and evaporated. The residue is dissolved in a nonpolar organic solvent, e.g., methylene chloride, washed, dried, evaporated and purified by flash chromatography to yield the desired blocked mercapto lower-alkyl modified thiopeptide, i.e., a compound of Formula 7.

Preparation of Formula I

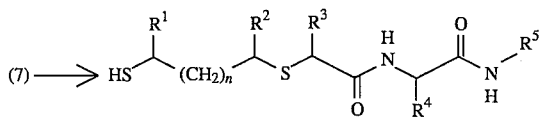

Formula I

To a solution of a blocked mercapto lower-alkyl modified thiopeptide, , i.e., a compound of Formula 7, in a solvent, such a methanol/water (about 7:1 ratio), is added about 1 molar equivalent of a deblocking reagent, such as mercuric acetate. The mixture is stirred at about room temperature for a period of about 30 to 90 minutes, preferably about 60 minutes. $H_2S$ gas is bubbled through the solution for a period of about 15 minutes, water is added and the resulting precipitate is removed by filtration. The filtrate is extracted with a nonpolar organic solvent, e.g., methylene chloride. The extracts are combined, washed with water, and dried with a drying agent, such as $Na_2SO_4$. The solvent is evaporated and the residue is purified by flash chromatography to yield the desired optionally substituted mercapto thiopeptide, i.e., a compound of Formula I.

REACTION SCHEME B

Reaction Scheme B describes the preparation of compounds of Formula I where $R^2$ is hydrogen, n is 0, and $R^1$, $R^3$, and $R^4$ are the same as described in the Summary of the Invention.

Preparation of Formula 9

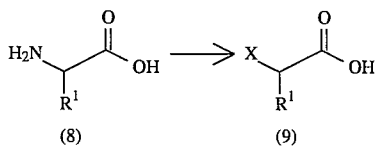

An amino acid or modified amino acid, i.e., a compound of Formula 8, is combined with about 3.5 molar equivalents of a halogen salt, such as, NaBr, KBr, NaCl, KCl, NaI, KI, preferably, KBr, and a strong acid, e.g., concentrated $H_2SO_4$ (about 0.2 mL/molar equivalent) in water at a temperature in the range of about –10° C. to 0° C., preferably about –4° C. To this solution is added about 1.5 molar equivalents of a nitrosating reagent, such as, $NaNO_2$ over a period of about 1 hour. After completion of the addition, the reaction mixture is stirred for an additional 1 hour. The solution is extracted with a non-polar organic solvent, e.g., methylene chloride. The organic layer is washed, dried and evaporated to yield the desired halo carboxylic acid, i.e., a compound of Formula 9.

Preparation of Formula 10

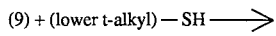

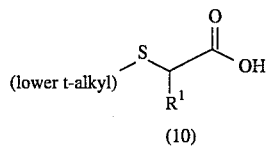

About 2 molar equivalents of a base, such as sodium ethoxide, and 9 molar equivalents of a lower t-alkyl mercaptan, such as, t-butylthiol, are combined in a solvent, such as, ethanol at about room temperature under an inert atmosphere with stirring for about 10 minutes. To this is added a solution of a halo optionally substituted carboxylic acid, i.e., a compound of Formula 9, in a solvent, such as, ethanol. The reaction mixture is stirred for a period of about 2 to 4 hours, preferably about 3 hours at about room temperature. The reaction mixture is poured into water, acidified with a weak acid, such as acetic acid and extracted with a nonpolar organic solvent, e.g., methylene chloride. The organic layer is dried with a drying agent, such as $Na_2SO_4$, and evaporated to yield the desired lower-alkyl substituted thiocarboxylic acid, i.e., a compound of Formula 10.

Preparation of Formula 11

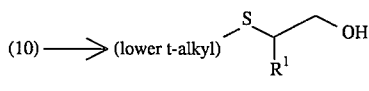

To a solution of a lower-alkyl substituted thiocarboxylic acid in an aprotic solvent, such as THF, at a temperature in the range of about –10° C. to 10° C., preferably about 0° C. is added a reducing agent, such as 1M borane/THF (about 2.5 mL/molar equivalent) in a gradual manner over a period of about 15 minutes with stirring. After completion of the addition, stirring is continued for a period of about 2 to 4 hours, preferably 3 hours. The reaction mixture is quenched by gradual addition of cold water. The mixture is extracted with a nonpolar organic solvent, e.g., methylene chloride, washed with a saturated weak base (such as $NaHCO_3$), washed with an acid (such as HCl), and dried over a drying agent (such as $Na_2SO_4$). The solvent is removed by vacuum and the residue purified by flash chromatography to yield the desired lower-alkyl thioalkylalcohol, i.e., a compound of Formula 11.

Preparation of Formula 12

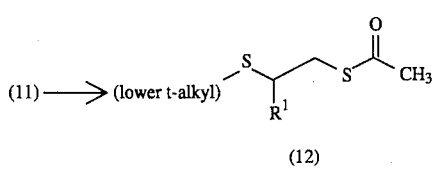

About 2 molar equivalents of triphenylphosphine and 2 molar equivalents of a dialkyl azodicarboxylate, such as diisopropyl azodicarboxylate, are combined with an aprotic solvent, such as THF at a temperature in the range of about −10° C. to 10° C., preferably about 0° C. After the ingredients are combined, the solution is stirred for a period of about 15 to 45 minutes, preferably about 30 minutes. The solution yields a precipitate which is combined with a lower-alkyl thioalcohol, i.e., compound of Formula 11. The solution is stirred for about 10 min, and about 2 molar equivalents of thiolacetic acid is added. The reaction mixture is stirred at about 0° C. for 1 hour, and at about room temperature for about 1 hour. The solvent is removed by vacuum, and the residue purified by flash chromatography to yield the desired lower-alkyl thioalkyl acetylthio compound, i.e., a compound of Formula 12.

Preparation of Formula 14

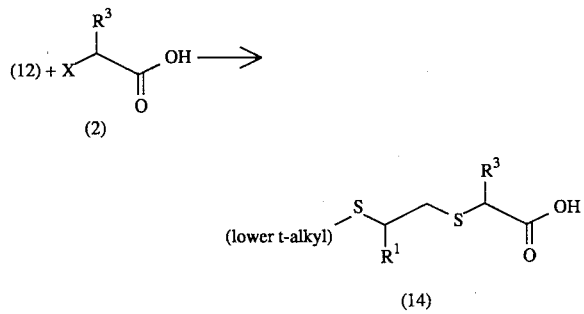

A lower-alkyl thioalkyl acetylthio compound, i.e., a compound of Formula 12 is combined in a solution with about 2 molar equivalents of a base such as sodium ethoxide in a solvent, such as ethanol, with stirring at about room temperature under an inert atmosphere. To this solution is added about 1 molar equivalent of an α-halo amino acid, or modified amino acid, i.e., a compound of Formula 2 with stirring. After completion of the addition, stirring is continued at about room temperature for a period of about 3 to 5 hours, preferably about 4 hours. The reaction mixture is added to water, acidified with a weak acid (such as, acetic acid) and extracted with a nonpolar organic solvent, e.g., methylene chloride. The organic layer is dried over a drying agent (such as Na₂SO₄) and evaporated. The residue is purified by chromatography, such as flash chromatography (15% ethyl acetate in hexane) to yield the desired optionally substituted thioalkylcarboxylic acid, i.e., a compound of Formula 14.

Preparation of Formula 15

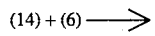

(14) + (6) ⟶

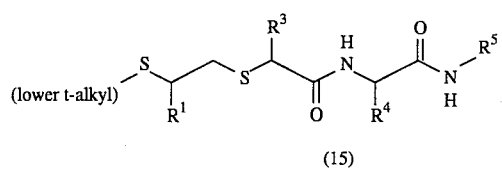

An optionally substituted thioalkylcarboxylic acid, is coupled to an optionally modified amino acid, or peptide fragment, i.e., a compound of Formula 6, by following the procedure described previously for the Preparation of Formula 7 (Reaction Scheme A) yielding the desired blocked mercapto peptide, i.e., a compound of Formula 15.

Preparation of Formula 16

(15) ⟶

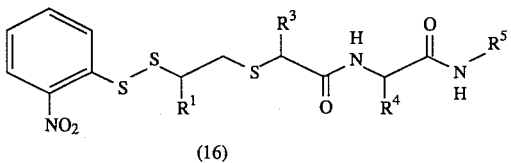

A solution of the blocked mercapto peptide and glacial acetic acid (about 3 mL/mmole) is formed. To this solution is added about 1 molar equivalent of an arylsulfenyl halide, such as 2-nitrophenylsulfenyl chloride. The mixture is stirred at about room temperature for a period of about 1 to 3 hours, preferably about 2 hours. The glacial acetic acid is evaporated under vacuum and the residue purified by chromatography, e.g., flash chromatography (35% ethyl acetate in hexane) to yield the desired aryldisulfide blocked modified peptide, i.e., a compound of Formula 16.

Preparation of Formula I

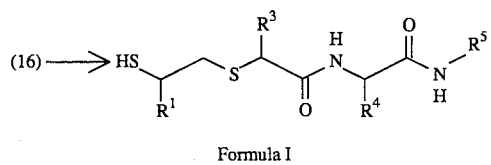

An aryldisulfide blocked modified peptide is dissolved in a solvent(s), such as a combination of methanol and dioxane (4:1 ratio) to this solution is added 2-mercaptoethanol (about 1.5 mL/molar equivalent) and about 100 molar equivalents of a NaOH solution. The mixture is stirred at about room temperature under an inert atmosphere for a period of about 15 to 45 minutes, preferably about 30 minutes. The reaction mixture is poured into water, acidified with a weak acid, and extracted with a nonpolar organic solvent, e.g., methylene chloride. The organic layer is dried over a drying agent (e.g., Na₂SO₄) and evaporated under vacuum. The residue is purified by chromatography, such as flash chromatography (25% ethyl acetate in hexane) to yield the desired optionally substituted mercapto peptide, i.e., a compound of Formula I.

REACTION SCHEME C

Preparation of Formula 17

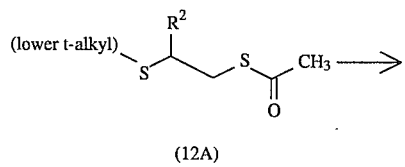

(12A)

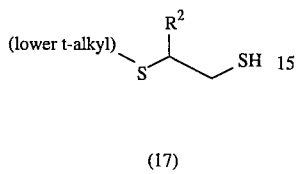

(17)

A lower-alkyl thioalkyl acetylthio compound, i.e., a compound of Formula 12A (prepared e.g., according to the procedures described in Reaction Scheme B for the preparation of a compound of Formula 12), is combined with about 1 molar equivalent of Na in an alcohol solvent, such as ethanol, under an inert atmosphere. The mixture is stirred for about 15 min, poured into water, acidified with a weak acid (e.g., acetic acid) and extracted with a nonpolar organic solvent, e.g., methylene chloride. The organic layer is dried over a drying agent (e.g., $Na_2SO4$), and evaporated to yield the crude desired lower-alkyl thioalkyl mercaptan, i.e., a compound of Formula 17. The compound is taken to the next step without further purification.

Preparation of Formula 18

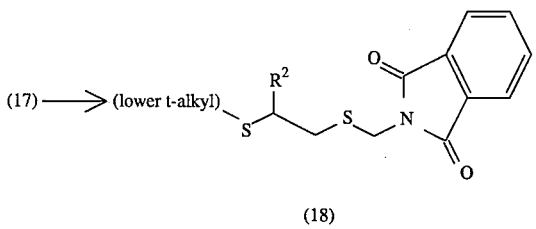

(18)

A lower t-alkyl thioalkyl mercaptan is dissolved in a nonpolar solvent, such as, methylene chloride, THF, diethyl ether, preferably methylene chloride, to this solution is added about 1.5 molar equivalents of a base, such as a lower-alkyl amine, preferably ethyl diisopropylamine, and about 1.2 molar equivalents of N-(bromomethyl)phthalimide with stirring at about room temperature under an inert atmosphere. After completion of the addition, the reaction mixture is stirred at about room temperature for a period of about 12 to 24 hours, preferably about 18 hours. The mixture is diluted with a nonpolar solvent, such as, methylene chloride, THF, diethyl ether, preferably methylene chloride, and extracted with 1M HCl. The organic layer is dried over a drying agent, and evaporated under vacuum. The residue is purified by chromatography, e.g., flash chromatography (10% ethyl acetate in hexane) to yield the desired lower t-alkyl thioalkyl phthalimide substituted compound, i.e., a compound of Formula 18.

Preparation of Formula 19

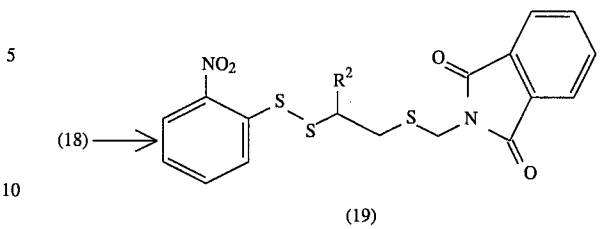

(19)

A lower t-alkyl thioalkyl phthalimide substituted compound is combined with acetic acid (about 2.7 mL/molar equivalent). To this solution is added about 1 molar equivalent of an arylsulfenyl halide, such as 2-nitrobenzenesulfenyl chloride. The reaction mixture is stirred at about room temperature for about 2 hours. The acetic acid is removed by evaporation, and the resulting residue is purified by chromatography, e.g., flash chromatography (10% ethyl acetate in hexane), yielding the desired aryldisulfide phthalimide substituted compound, i.e., a compound of Formula 19.

Preparation of Formula 20

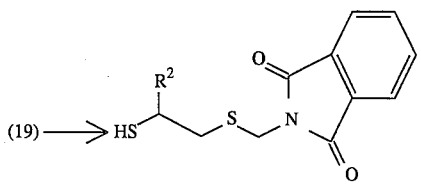

(20)

An aryldisulfide phthalimide substituted compound is dissolved in a solvent or combination of solvents (e.g., methanol/dioxane at about a 2:1 ratio). To this solution is added about 20 molar equivalents of 2-mercaptoethanol and about 1 molar equivalent of NaOH. The reaction mixture is stirred at about room temperature for about 30 minutes under an inert atmosphere. The mixture is poured into water, acidified with a weak acid, and extracted with a nonpolar solvent (e.g., methylene chloride). The organic layer is dried over a drying agent (e.g., $Na_2SO_4$) and evaporated. The residue is purified by chromatography, e.g., flash chromatography (35% ethyl acetate in hexane) to yield the desired phthalimide substituted mercaptan compound, i.e., a compound of Formula 20.

Preparation of Formula 22

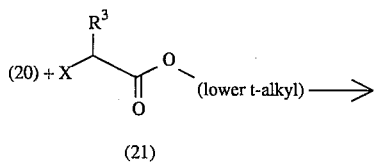

(21)

-continued

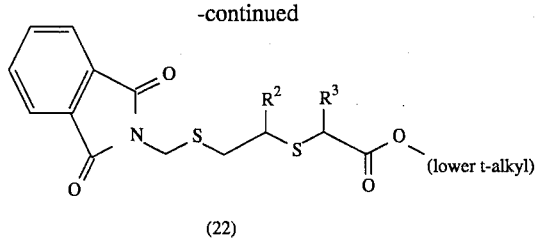

(22)

A phthalimide substituted mercaptan compound is combined with about 1.1 molar equivalents of an optionally substituted lower t-alkyl ester blocked optionally substituted α-halo amino acid (i.e., a compound of Formula 2, prepared as described in Reaction Scheme A that has been blocked at the —OH) in a solvent, such as acetonitrile. To this solution is added about 2 molar equivalents of N,N-diisopropylethylamine. The reaction mixture is stirred at about room temperature for a period of about 24 to 72 hours, preferably about 48 hours, under an inert atmosphere. The solvent is removed by evaporation, the resulting residue dissolved in a nonpolar organic solvent (e.g., methylene chloride), washed, and extracted with 1M HCl. The organic layer is isolated, dried over a drying agent, and evaporated under vacuum. The residue is purified by chromatography, e.g., flash chromatography (5% ethyl acetate in hexane), to yield the desired blocked C- and N-terminus modified peptide, i.e., a compound of Formula 22.

Preparation of Formula 23

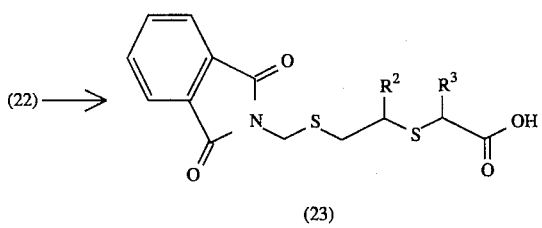

(23)

A blocked C- and N-terminus modified peptide, i.e., a compound of Formula 22, is combined with trifluoroacetic acid (about 1 mL/mmole equivalent) and water (about 38 μL/mmole). The reaction mixture is stirred at about 5° C. for a period of about 12 to 24 hours, preferably about 18 hours. The solvent is removed by vacuum and the residue purified by chromatography, e.g., flash chromatography (45% ethyl acetate in hexane) to yield the desired blocked N-terminus compound, i.e., a compound of Formula 23.

Preparation of Formula 24

(23) + (6) ⟶

-continued

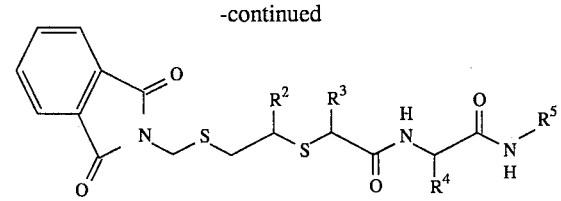

(24)

An blocked N-terminus compound is coupled to an optionally modified amino acid, or peptide fragment, i.e., a compound of Formula 6, by following the procedure described previously for the Preparation of Formula 7 (Reaction Scheme A) yielding the desired correspondingly optionally substituted blocked N-terminus peptide, i.e., a compound of Formula 24.

Preparation of Formula 25

(24) ⟶

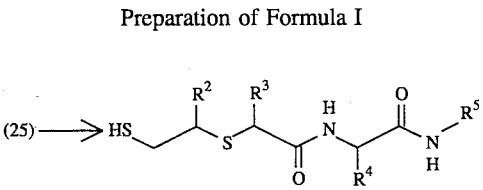

(25)

An optionally substituted blocked N-terminus peptide is combined with acetic acid. To this solution is added about 1.1 molar equivalents of an arylsulfenyl halide, such as 2-nitrobenzenesulfenyl chloride. The reaction mixture is stirred at about room temperature for a period in the range of about 12 to 24 hours, preferably about 18 hours. The acetic acid is removed by vacuum, and the residue purified by chromatography, e.g., flash chromatography (5% ethyl acetate in methylene chloride), yielding the desired correspondingly optionally substituted aryldisulfide peptide, i.e., a compound of Formula 25.

Preparation of Formula I

(25) ⟶ 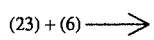

Formula I

An optionally substituted aryldisulfide peptide is deblocked at the N-terminus by following the procedure described previously for the Preparation of Formula I (Reaction Scheme B) to yield the desired optionally substituted modified mercapto thiopeptide, i.e., a compound of Formula I.

PREFERRED COMPOUNDS

Presently preferred is the compound of Formula I where n is 0.

Especially preferred is the compound of Formula I where $R^3$ is 2-methylpropyl.

Also especially preferred is the compound of Formula I where $R^4$ is phenylmethyl.

Also especially preferred is the compound of Formula I where $R^5$ is methyl or benzyl.

Also especially preferred in the compound of Formula I where the carbon to which $R^3$ is attached is in the D-configuration.

Also especially preferred is the compound of Formula I where $R^1$ and $R^2$ are hydrogen.

Also especially preferred is the compound of Formula I where $R^1$ is methyl, amino(n-butyl), PhtN(n-butyl), 2-aminoethyl, 2-PhtN(ethyl) or carbamoylmethyl.

Also especially preferred is the compound of Formula I where $R^2$ is methyl or i-butyl.

Of the compound where n is 0, most preferred is the compound of Formula I where $R^3$ is 2-methylpropyl, $R^4$ is phenylmethyl, $R^5$ is methyl, $R^1$ and $R^2$ are hydrogen, and the carbon to which $R^3$ is attached is in the D-configuration.

Of the compound where n is 0, most preferred is the compound of Formula I where $R^3$ is 2-methylpropyl, $R^4$ is phenylmethyl, $R^5$ is methyl, $R^1$ is methyl, $R^2$ is hydrogen, and the carbon to which $R^3$ is attached is in the D-configuration.

Of the compound where n is 0, most preferred is the compound of Formula I where $R^3$ is 2-methylpropyl, $R^4$ is phenylmethyl, $R^5$ is methyl, $R^1$ is PhtNBu, $R^2$ is hydrogen, and the carbon to which $R^3$ is attached is in the D-configuration.

Of the compound where n is 0, most preferred is the compound of Formula I where $R^3$ is 2-methylpropyl, $R^4$ is phenylmethyl, $R^5$ is methyl, $R^1$ is PhtNEt, $R^2$ is hydrogen, and the carbon to which $R^3$ is attached is in the D-configuration.

Of the compound where n is 0, most preferred is the compound of Formula I where $R^3$ is 2-methylpropyl, $R^4$ is phenylmethyl, $R^5$ is benzyl, $R^1$ and $R^2$ are hydrogen, and the carbon to which $R^3$ is attached is in the D-configuration.

Of the compound where n is 0, most preferred is the compound of Formula I where $R^3$ is 2-methylpropyl, $R^4$ is phenylmethyl, $R^5$ is benzyl, $R^1$ is methyl, $R^2$ is hydrogen, and the carbon to which $R^3$ is attached is in the D-configuration.

Of the compound where n is 0, most preferred is the compound of Formula I where $R^3$ is 2-methylpropyl, $R^4$ is phenylmethyl, $R^5$ is benzyl, $R^1$ is PhtNBu, $R^2$ is hydrogen, and the carbon to which $R^3$ is attached is in the D-configuration.

Of the compound where n is 0, most preferred is the compound of Formula I where $R^3$ is 2-methylpropyl, $R^4$ is phenylmethyl, $R^5$ is benzyl, $R^1$ is PhtNEt, $R^2$ is hydrogen, and the carbon to which $R^3$ is attached is in the D-configuration.

UTILITY, TESTING AND ADMINISTRATION

General Utility

The compounds of this invention, including the pharmaceutically acceptable esters, ethers, or salts thereof, and the compositions containing them are useful for modulating physiological functions or treating diseases and disease conditions associated with the modulation of MMP activity, e.g., arthritic diseases, such as osteoarthritis (OA), rheumatoid arthritis (RA), septic arthritis, soft tissue rheumatism, polychondritis and tendonitis; tumor invasion in certain cancers, periodontal diseases; corneal ulceration, e.g., that induced by alkali or other burns, by radiation, by vitamin E or retinoid deficiency; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; angiogenesis relating to tumor growth on to the neovascularization associated with diabetic retinopathy and macular degeneration; coronary thrombosis associated with atherosclerotic plaque rupture; and pulmonary emphysema.

The compounds of this invention inhibit MMP, thereby providing a means of controlling conditions (normal physiological or disease states) modulated or mediated by MMP, particularly those where elevated levels of MMP have been detected.

All forms of arthritis (i.e., arthritic diseases soft tissue rheumatism, polychondritis and tendonitis) are characterized by the erosion of the articular cartilage of affected joints. Since cartilage consists primarily of proteoglycans and type II collagen, proteinases capable of attacking both macromolecules have been implicated in the progression of the diseases [Harris et al., (1969) *Arthritis Rheum.* 12, 92–102; Harris et al., (1970) *Arthritis Rheum.* 13, 83–95; Woolley et al., (1977) *Arthritis Rheum.* 20, 1231–1239; and Krane, S. M., (1981) *Ann. Rheum. Dis.* 40, 433–448].

The metastasis of tumor cells is a process that is inhibited by the connective tissue barriers of the host. The association of both interstitial collagenases and proteinases capable of degrading type IV collagen found in basement membrane is well documented and is believed to facilitate metastasis [Strauli et al., (1980) *Proteinases and Tumor Invasion*, Raven Press, New York; Liotta et al., (1991) *Tumor Invasion and Metastasis*, pp. 319–333, Martinus Nijhoff, Dordrecht; Blood, C. H. and Zetter, B. R., (1990) *Biochim. Biophys. Acta* 1032, 89–118; Liotta et al., (1983) *Lab. Invest.* 49, 636–649; and Liotta et al., (1980) *Nature* (London) 284, 67–68].

Periodontal disease is an inflammatory disease that is triggered by bacteria that inhabit the gingival cavity. Periodontis is characterized by the progressive loss of the attachment apparatus of teeth. Since the major protein component of gingival tissue and bone is type I collagen, collagenases are believed to participate in the progression of the disease [Robertson, P. B. and simpson, J. (1976) *J. Periodontol.*, 47, 29–33; and Birkedal-Hansen, H., (1980) in *Collagenases in Normal and Pathological Connective Tissue*, (Woolley, D. E. and Evanson, J. M., eds), pp. 127–140, Wiley and Sons, New York].

Corneal ulceration can be brought about by chemical or thermal burns, infections Stevens-Johnson syndrome, Mooren's ulcer, vitamin A deficiency, and many other diseases. The corneal stroma is composed predominantly of type I collagen that is progressively degraded during ulceration [Van Wart, H. E. and Mookhtiar, K. A. (1990) in *Biological Response Modifiers for Tissue Repair* (Grotendorst, G., Jhelmeland, L. M. and Gills, J. P., eds), pp. 23–50, Portfolio, The Woodlands, Tex.; Brown et al., (1969) *Arch. Ophthalmol.* 81, 370– 373; and Berman, M. B. (1980) in *Collagenases in Normal and Pathological Connective Tissue*, (Woolley, D. E. and Evanson, J. M., eds), pp. 141–174, Wiley and Sons, New York].

Glomerular diseases, such as proteinuria, dytrophobic epidermolysis bullosa, which a separation of the dermis and epidermis, are believed to be influenced by collagenases [Eisen, A. Z. (1969) *J. Invest. Dermatol.* 52, 449– 453].

Bone resorption diseases, such as osteoporosis, Paget's disease, hyperparathyroidism and cholesteatoma, are believed to involve the action of collagenases [Vaes, G. (1980) in *Collagenases in Normal and Pathological Connective Tissue*, (Woolley, D. E. and Evanson, J. M., eds), pp. 185–207, Wiley and Sons, New York; Gardner et al., (1971) *Surg. Forum*, 22, 435–437; Abramson, M. (1969) *Ann. Otol. Rhinol. Laryngol.*, 78, 112–124; Sakamoto et al., (1975) *Biochem. Biophys. Res. Commun.* 63, 172–177; Griffith et al., (1965) *J. Am. Med. Assoc.* 193, 91–94; and Eeckhout et al., (1986) *Biochem. J.* 239 793–796].

Certain MMP have been reported as mediating ovulation and implantation, thus inhibition of these MMP would provide a means of birth control [Librach et al., *J. Cell Biol.*, 13, 437–449, 1991; and Brännström et al., *Endocrinology*, 122, 5, 1715–1721, 1988].

Certain MMP have been associated with angiogenesis relating to tumor growth or to the neovascularization associated with diabetic retinopathy and macular degeneration. Inhibition of these MMP would provide a means of slowing or halting the development of such conditions [Moses et al., *Bio/technology*, 9, 630–634, 1991; and Langer et al., *Proc. Natl. Aca. Sci. USA*, 77, 7, 4331–4335, 1980)].

MMP have been linked with coronary thrombosis caused by atherosclerotic plaque rupture [Henney et al., *Proc. Natl. Acad. Sci.*, 88, 8154–8158, 1991]. Inhibition of MMP could alleviate this condition.

Interstitial collagenase has been implicated as a possible etiological agent in the emphysema disease process. Although elastase has been proposed as the primary enzyme responsible for emphysematous lung damage, there is evidence that other extra-ceullular matrix proteases could play a role in emphysema [D'Armiento et al., *Cell*, 71, 955–961 Dec. 11, 1992].

Testing

The potency and selectivity of compounds of the present invention as inhibitors of MMP are determined by assay against MMPs that are associated with the metabolic turnover of interstitial collagens in the extracellular matrix of humans. For example, following the procedures described in Example 21, or modifications thereof.

Five types of MMP are assayed, i.e., fibroblast-type collagenase (HFC), gelatinase (HFG) and stromelysin (HFS) and neutrophil-type collagenase (HNC) and gelatinase (HNG).

The assay method is based on the hydrolysis of DNP-Pro-Leu-Ala-Leu-Trp-Ala-Arg as the substrate (according to Netzel-Arnett, S.; Mallya, S. K.; Nagase, H.; Birkedal-Hansen, H.; Van Wart, H. E. *Anal. Biochem.* 1991, 195, 86–92).

Administration

The compounds of this invention are administered at a therapeutically effective dosage, i.e., that amount which, when administered to a mammal in need thereof, is sufficient to effect treatment, as described above (for example, to reduce or otherwise treat inflammation, pain and/or pyrexia in the mammal). Administration of the active compounds and salts described herein can be via any of the accepted modes of administration for agents that serve similar utilities.

The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably the drug is present at a level of about 10% w to about 70% w.

Generally, an acceptable daily dose is of about 0.001 to 50 mg per kilogram body weight of the recipient per day, preferably about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5mg to 1.75 g per day, and most preferably about 0.7 mg to 0.7 g per day depending upon the individuals and disease state being treated. Such use optimization is well within the ambit of those of ordinary skill in the art.

Administration can be via any accepted systemic or local route, for example, via parenteral, oral (particularly for infant formulations), intravenous, nasal, bronchial inhalation (i.e., aerosol formulation), transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in *"Remington's Pharmaceutical Sciences"* by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula I. The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

Intravenous Administration

Intravenous injection has proven to be an important route of administration for therapeutic agents. The compounds of the present invention can be administered via this route, for example, by dissolving the compound, ester, ether or salt in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

Oral Administration

Oral administration can be used to deliver the compound of Formula I using a convenient daily dosage regimen which can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt % and 99.99 wt/wt % of the compound of Formula I, but preferably such compositions will contain between 25 wt/wt % and about 80 wt/wt %.

Preferably the compositions will take the form of a capsule, pill or tablet and thus the composition will contain, along with the active ingredient, a diluent such as lactose, sucrose, dicalciumphosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

Liposomal Formulations

Pharmaceutical formulations based on liposomes have recently reached human clinical trials. Their benefits are believed related to favorable changes in tissue distribution and pharmacokinetic parameters that result from liposome entrapment of drugs, and may be applied to the compounds of the present invention by those skilled in the art.

The formulations can be designed to either target drug to disease sites [see: Lopez-Berestein et al., *J. Infect. Dis.*, 151:704–710 (1985); Gotfredsen et al., *Biochemical Pharmacology*, 32:3389–3396 (1983)]; or to the reticuloendothelial system [see Eppstein et al., *Int. J. Immunotherapy*, 2: 115–126 (1986)], to increase duration of drug action [see: Gabizon et al., *Cancer Res.*, 42:4734 (1982); Eppstein et al., *Delivery Systems for Peptide Drugs*, Eds. S. S. Davis, L. Illum and E. Tomlinson, Plenum Pub. Corp., New York, pp. 277–283; C. A. Hunt, *Biochemica et Biophysica Acta*, 719:450–463 (1982); and Senior et al., *Biochemica et Biophysica Acta*, 839:1–8 (1985)], or to divert a drug away from organs that are particularly sensitive to its toxic effects [see: Weinstein et al., *Pharmac. Ther.*, 24:207–233 (1983); Olson et al., *Eur. J. Cancer Clin. Oncol.*, 18:167–176 (1982); and Gabzion et al., supra.].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intestine capsules have also been suggested, see U.S. Pat. No. 4,348,384. The foregoing are incorporated herein by reference.

Suppositories

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from about 1 wt/wt % to about 2 wt/wt %.

Liquids

Liquid pharmaceutically administrable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following examples are given to enable those skilled in the art to more clearly understand and to practice the present invention. They should not be considered as limiting the scope of the invention, but merely as being illustrative and representative thereof.

EXAMPLE 1

Preparation of (2R) 2-Bromo-4-Methylpentanoic Acid

1A. Formula 2 Where X Is Bromo and $R^3$ Is 2-Methylpropyl

A solution of 3.00 g of D-Leu, 9.53 g of KBr in 15 mL of water and 4.5 mL of conc. $H_2SO_4$ was formed and stirred at $-4°$ C. To this solution was added 2.09 g of $NaNO_2$ in 10 mL of water over a period of 1 h. Stirring was continued for 1 h at the same temperature, then the reaction mixture was extracted with $CH_2Cl_2$. The organic layer was washed with water, dried over $Na_2SO_4$ and evaporated under vacuum to give 3.72 g of (2R)-2-bromo-4-methylpentanoic acid at 83% yield as a colorless oil. Characteristic analytical data are as follows: $^1$H NMR (300 MHz, $CDCl_3$) d 4.31 (t, J=8 Hz, 1H), 1.94 (t, J=7 Hz, 2H), 1.82 (m, 1H), 0.98 (d, J=7 Hz, 3H), 0.93 (d, J=7 Hz, 3H); $[\alpha]_D^{25}$ +39.0° (c=2.02, MeOH).

1B. Preparation of the Corresponding (2S) Isomer of Formula 2

By following the same procedures described in Example 1A and substituting L-Leu for D-Leu, (2S)-2-bromo-5-methylpentanoic acid was obtained in 83% yield. Characteristic analytical data are as follows: $[\alpha]_D^{25}$ −39.8° (c=2.00, MeOH); $[\alpha]_{546}^{25}$ −47.5° (c=2.00, MeOH).

1C. Formula 2 Varying $R^3$

By following the procedures described in Example 1A and substituting D-Leu with other compounds of Formula 1 and KBr with other halo salts there are obtained the correspondingly substituted compounds of Formula 2 (where $R^3$ is as indicated in the table below).

Formula 2

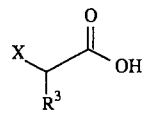

| X | R³ | Name |
|---|----|------|
| Cl | hydrogen | 2-chloroethanoic acid |
| Br | methyl | (2R)-2-bromopropanoic acid |
| Br | 2-propyl | (2R)-2-bromo-3-methylbutanoic acid |
| Cl | 2-butyl | (2R)-2-chloro-3-methylpentanoic acid |
| Br | benzyl | (2R)-2-bromo-3-phenylpropanoic acid |
| Br | blocked 4-hydroxyphenylmethyl | (2R)-2-bromo-3-(4-hydroxyphenyl)propanoic acid |
| Br | blocked 3-indolylmethyl | (2R)-2-bromo-3-(3-indolyl)propanoic acid |
| Br | 4-methoxyphenylmethyl | (2R)-2-bromo-3-(4-methoxyphenyl)propanoic acid |
| Cl | phenylethyl | (2R)-2-chloro-4-phenylbutanoic acid |

1D. Formula 2 Varying R³

By following the procedures described in Example 1A and substituting L-Leu with other compounds of Formula 1 and KBr with other halo salts there are obtained the correspondingly substituted compounds of Formula 2 (where R³ is as indicated in the table below).

Formula 2

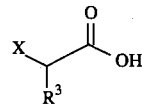

| X | R³ | Name |
|---|----|------|
| Br | methyl | (2S)-2-bromopropanoic acid |
| Br | 2-propyl | (2S)-2-bromo-3-methylbutanoic acid |
| Cl | 2-butyl | (2S)-2-chloro-3-methylpentanoic acid |
| Br | benzyl | (2S)-2-bromo-3-phenylpropanoic acid |
| Br | blocked 4-hydroxyphenylmethyl | (2S)-2-bromo-3-(4-hydroxyphenyl)propanoic acid |
| Br | blocked 3-indolylmethyl | (2S)-2-bromo-3-(3-indolyl)propanoic acid |
| Br | 4-methoxyphenylmethyl | (2S)-2-bromo-3-(4-methoxyphenyl)propanoic acid |

Formula 2 -continued

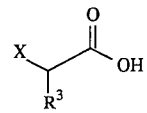

| X | R³ | Name |
|---|----|------|
| Cl | phenylethyl | (2S)-2-chloro-4-phenylbutanoic acid |

EXAMPLE 2

Preparation of $HS(CH_2)_2$—(S-D-Leu)-Oh

2A. Formula 4 Where n is 0, $R^1$ and $R^2$ Are Hydrogen and $R^3$ is 2-Methylpropyl To a solution of 2.4 g of Na in 50 mL of EtOH was added 50 mL of ethanedithiol with stirring at room temperature under nitrogen. After 10 min a solution of 8.1 g of (2S)-2-bromo-4-methylpentanoic acid in 10 mL of EtOH was added. The reaction mixture was stirred at room temperature for 16 h. The mixture was poured into water and was acidified with acetic acid and extracted with $CH_2Cl2$. The organic layer was dried over $Na_2SO_4$ and the solvent and excess ethanedithiol were evaporated under vacuum. Purification of the residue by flash chromatography (15% EtOAc in hexane) afforded 4.63 g of $HS(CH_2)_2$—(S-D-Leu)-OH as a colorless gum at 54% yield. Characteristic analytical data are as follows: $^1H$ NMR (300 MHz, $CDCl_3$) d 3.34 (t, J=7 Hz, 1H), 2.70–3.02 (m, 4H), 1.78 (m, 2H), 1.70 (t, J=8 Hz, 1H, SH), 1.55 (m, 1H), 0.94 (d, J=6 Hz, 3H), 0.93 (d, J=6 Hz, 3H); $[\alpha]_D^{25}$ +76.2° (c=2.04, MeOH).

2B. Preparation of the Corresponding (S-L-Leu) Isomer of Formula 4

By following the procedure described in Example 2A and substituting (2S)-2-bromo-4-methylpentanoic acid with (2R)-2-bromo-4-methylpentanoic acid, $HS(CH_2)_2$—(S-L-Leu)-OH was obtained at 57% yield. Characteristic analytical data are as follows: $[\alpha]_D^{25}$ −71.8° (c=1.78, MeOH).

2C. Formula 4 Varying R³

By following the procedures described in Example 2A and substituting (2S)-2-bromo-4-methylpentanoic acid with other compounds of Formula 2 there are obtained the correspondingly substituted of compounds of Formula 4 (where R³ is as indicated in the table below).

Formula 4

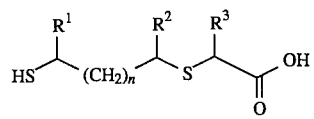

| R³ | Name |
|----|------|
| hydrogen | $HS(CH_2)_2$—(S—Gly)—OH |
| methyl | $HS(CH_2)_2$—(S—D—Ala)—OH |
| 2-propyl | $HS(CH_2)_2$—(S—D—Val)—OH |
| 2-butyl | $HS(CH_2)_2$—(S—D—Ile)—OH |
| benzyl | $HS(CH_2)_2$—(S—D—Phe)—OH |
| blocked 4-hydroxyphenylmethyl | $HS(CH_2)_2$—(S—D—Tyr)—OH |
| blocked 3-indolylmethyl | $HS(CH_2)_2$—(S—D—Trp)—OH |
| 4-methoxyphenylmethyl | $HS(CH_2)_2$—(S—D—Tyr—$OCH_3$)—OH |
| phenylethyl | $HS(CH_2)_2$—(S—D—Phet)—OH |

2D. Formula 4 Varying $R^3$

By following the procedures described in Example 2B and substituting (2R)-2-bromo-4-methylpentanoic acid with other compounds of Formula 2 there are obtained the correspondingly substituted of compounds of Formula 4 (where $R^3$ is as indicated in the table below).

Formula 4

$$\text{HS}\overset{R^1}{-}(CH_2)_n\overset{R^2}{-}S\overset{R^3}{-}\underset{O}{\overset{\|}{C}}-OH$$

| $R^3$ | Name |
|---|---|
| methyl | $HS(CH_2)_2-(S-L-Ala)-OH$ |
| 2-propyl | $HS(CH_2)_2-(S-L-Val)-OH$ |
| 2-butyl | $HS(CH_2)_2-(S-L-Ile)-OH$ |
| benzyl | $HS(CH_2)_2-(S-L-Phe)-OH$ |
| blocked 4-hydroxyphenylmethyl | $HS(CH_2)_2-(S-L-Tyr)-OH$ |
| blocked 3-indolylmethyl | $HS(CH_2)_2-(S-L-Trp)-OH$ |
| 4-methoxyphenylmethyl | $HS(CH_2)_2-(S-L-Tyr-OCH_3)-OH$ |
| phenylethyl | $HS(CH_2)_2-(S-L-Phet)-OH$ |

2E. Formula 4 Varying n, $R^1$, $R^2$ and $R^3$

By following the procedures described in Example 2A and substituting ethanedithiol with other compounds of Formula 3 and (2S)-2-bromo-4-methylpentanoic acid with other compounds of Formula 2 (e.g., compounds with $R^3$ that are prepared according to Example 1A) there are obtained the correspondingly substituted compounds of Formula 4 (where n, $R^1$, $R^2$ and $R^3$ are as indicated in the table below).

Formula 4

$$\text{HS}\overset{R^1}{-}(CH_2)_n\overset{R^2}{-}S\overset{R^3}{-}\underset{O}{\overset{\|}{C}}-OH$$

| n | $R^1$ | $R^2$ | $R^3$ |
|---|---|---|---|
| 0 | | $-CH_2-CH_2-CH_2-$ | hydrogen |
| 0 | | $-CH_2-CH_2-CH_2-$ | methyl |
| 0 | | $-CH_2-CH_2-CH_2-$ | 2-propyl |
| 0 | | $-CH_2-CH_2-CH_2-$ | 2-butyl |
| 0 | | $-CH_2-CH_2-CH_2-$ | 2-methylpropyl |
| 0 | | $-CH_2-CH_2-CH_2-$ | blocked 4-hydroxyphenylmethyl |
| 0 | | $-CH_2-CH_2-CH_2-$ | blocked 3-indolylmethyl |
| 0 | | $-CH_2-CH_2-CH_2-$ | 4-methoxyphenylmethyl |
| 0 | | $-CH_2-CH_2-CH_2-$ | phenylethyl |
| 0 | methyl | methyl | hydrogen |
| 0 | n-butyl | n-butyl | methyl |
| 0 | benzyl | benzyl | 2-propyl |
| 0 | phenylethyl | phenylethyl | 2-butyl |
| 0 | blocked aminomethyl | blocked aminomethyl | benzyl |
| 0 | methyl-carbonylethyl | methyl-carbonylethyl | blocked 4-hydroxyphenylmethyl |
| 0 | PhtN-methyl | PhtN-methyl | blocked 3-indolylmethyl |
| 0 | PhtN-ethyl | PhtN-ethyl | 4-methoxyphenylmethyl |
| 0 | TsNH-methyl | TsNH-methyl | phenylethyl |
| 1 | | $-CH_2-CH_2-CH_2-$ | hydrogen |
| 1 | | $-CH_2-CH_2-CH_2-$ | methyl |
| 1 | | $-CH_2-CH_2-CH_2-$ | 2-propyl |
| 1 | | $-CH_2-CH_2-CH_2-$ | 2-butyl |
| 1 | | $-CH_2-CH_2-CH_2-$ | benzyl |
| 1 | | $-CH_2-CH_2-CH_2-$ | blocked 4-hydroxyphenylmethyl |
| 1 | | $-CH_2-CH_2-CH_2-$ | blocked 3-indolylmethyl |
| 1 | | $-CH_2-CH_2-CH_2-$ | 4-methoxyphenylmethyl |
| 1 | | $-CH_2-CH_2-CH_2-$ | phenylethyl |
| 1 | methyl | methyl | hydrogen |
| 1 | n-butyl | n-butyl | methyl |
| 1 | benzyl | benzyl | 2-propyl |
| 1 | phenylethyl | phenylethyl | 2-butyl |
| 1 | blocked aminomethyl | blocked aminomethyl | benzyl |
| 1 | methyl-carbonylethyl | methyl-carbonylethyl | blocked 4-hydroxyphenylmethyl |
| 1 | PhtN-methyl | PhtN-methyl | blocked 3-indolylmethyl |
| 1 | PhtN-ethyl | PhtN-ethyl | 4-methoxyphenylmethyl |
| 1 | TsNH-methyl | TsNH-methyl | phenylethyl |

EXAMPLE 3

Preparation of $BzNHCH_2S(CH_2)_2-(S-D-Leu)-OH$

3A. Formula 5 Where n Is 0, $R^1$ and $R^2$ Are Hydrogen and $R^3$ Is 2-Methylpropyl To a mixture of 4.63 g of HS $(CH_2)_2$- (S-D-Leu)—OH and 3.53 g of $BzNHCH_{20}H$ was added 50 mL of trifluoroacetic acid with stirring at 0° C. After completion of the addition, the reaction mixture was stirred for an additional hour. The trifluoroacetic acid was evaporated under vacuum and the residue was passed through silica gel (25% EtOAc in hexane) to give 7.21 g of BzNHCH$_2$S(CH$_2$)$_2$—(S-D-Leu)-OH as a colorless gum 95% yield. Characteristic analytical data are as follows: $^1$H NMR (300 MHz, CDCl$_3$) δ7.81 (d, J=8 Hz, 2H), 7.54 (t, J=8 Hz, 1H), 7.45 (t, J=8 Hz, 2H), 6.83 (br t, J= 6 Hz, 1H, NH), 4.63 (dd, J=6, 14 Hz, 1H), 4.58 (dd, J=6, 14 Hz, 1H), 3.42 (dd, J=7, 9 Hz, H), 2.73–3.04 (m, 4H), 1.74 (m, 2H), 1.50 (m, 1H), 0.91 (d, J=6 Hz, 3H), 0.89 (d, J=6 Hz, 3H).

3B. Preparation of the Corresponding (S-L-Leu) Isomer of Formula 5

By following the procedure in Example 3A and substituting HS (CH$_2$)$_2$—(S-L-Leu)—OH for HS(CH$_2$)$_2$—(S-D-Leu)-OH, BzNHCH$_2$S(CH$_2$)$_2$—(S-L-Leu)-OH was obtained as a colorless gum at 92% yield. Characteristic analytical data are as follows: $^1$H NMR (300 MHz, CDCl$_3$) δ7.79 (d, J=7 Hz, 2H), 7.53 (t, J= 7 Hz, 1H), 7.43 (t, J=7 Hz, 2H), 7.06 (br s, 1H, NH), 4.68 (dd, J=7, 14 Hz, 1H), 4.54 (dd, J=6, 14 Hz, 1H), 3.40 (dd, J=7, 9 Hz, 1H), 2.73–3.05 (m, 4H), 1.65–1.82 (m, 2H), 1.50 (m, 1H), 0.90 (d, J=6 Hz, 3H), 0.88 (d, J=6 Hz, 3H).

3C. Formula 5 Varying R$^3$

By following the procedures described in Example 3A and substituting HS(CH$_2$)$_2$—(S-D-Leu)-OH with other compounds of Formula 4 (e.g., compounds that are prepared according to Examples 2A) there are obtained the correspondingly substituted of compounds of Formula 5 (where n, R$^1$, R$^2$ and R$^3$ are as indicated in the table below).

Formula 5

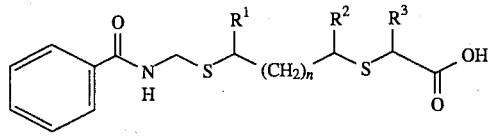

| R$^3$ | Name |
|---|---|
| hydrogen | BzNHCH$_2$S(CH$_2$)$_2$—(S—Gly)—OH |
| methyl | BzNHCH$_2$S(CH$_2$)$_2$—(S—D—Ala)—OH |
| 2-propyl | BzNHCH$_2$S(CH$_2$)$_2$—(S—D—Val)—OH |
| 2-butyl | BzNHCH$_2$S(CH$_2$)$_2$—(S—D—Ile)—OH |
| benzyl | BzNHCH$_2$S(CH$_2$)$_2$—(S—D—Phe)—OH |
| blocked 4-hydroxyphenylmethyl | BzNHCH$_2$S(CH$_2$)$_2$—(S—D—Tyr)—OH |
| blocked 3-indolylmethyl | BzNHCH$_2$S(CH$_2$)$_2$—(S—D—Trp)—OH |
| 4-methoxyphenylmethyl | BzNHCH$_2$S(CH$_2$)$_2$—(S—D—Tyr—OCH$_3$)—OH |
| phenylethyl | BzNHCH$_2$S(CH$_2$)$_2$—(S—D—Phet)—OH |

3D. Formula 5 Varying R$^3$

By following the procedures described in Example 3B and substituting HS(CH$_2$)$_2$—(S-L-Leu)-OH with other compounds of Formula 4 (e.g., compounds that are prepared according to Examples 2B) there are obtained the correspondingly substituted of compounds of Formula 5 (where n, R$^1$, R$^2$ and R$^3$ are as indicated in the table below).

Formula 5

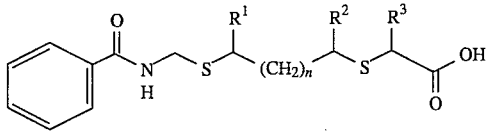

| R³ | Name |
|---|---|
| methyl | BzNHCH₂S(CH₂)₂—(S—L—Ala)—OH |
| 2-propyl | BzNHCH₂S(CH₂)₂—(S—L—Val)—OH |
| 2-butyl | BzNHCH₂S(CH₂)₂—(S—L—Ile)—OH |
| benzyl | BzNHCH₂S(CH₂)₂—(S—L—Phe)—OH |
| blocked 4-hydroxyphenylmethyl | BzNHCH₂S(CH₂)₂—(S—L—Tyr)—OH |
| blocked 3-indolylmethyl | BzNHCH₂S(CH₂)₂—(S—L—Trp)—OH |
| 4-methoxyphenylmethyl | BzNHCH₂S(CH₂)₂—(S—L—Tyr—OCH₃)—OH |
| phenylethyl | BzNHCH₂S(CH₂)₂—(S—L—Phet)—OH |

3E. Formula 5 Varying n, $R^1$, $R^2$ and $R^3$

By following the procedures described in Example 3A and substituting HS(CH₂)₂—(S-D-Leu)-OH with other compounds of Formula 4 (e.g., compounds that are prepared according to Examples 2A–2E) there are obtained the correspondingly substituted of compounds of Formula 5 (where n, $R^1$, $R^2$ and $R^3$ are as indicated in the table below).

Formula 5

| n | $R^1$ | $R^2$ | $R^3$ |
|---|---|---|---|
| 0 | —CH₂—CH₂—CH₂— | | hydrogen |
| 0 | —CH₂—CH₂—CH₂— | | methyl |
| 0 | —CH₂—CH₂—CH₂— | | 2-propyl |
| 0 | —CH₂—CH₂—CH₂— | | 2-butyl |
| 0 | —CH₂—CH₂—CH₂— | | 2-methylpropyl |
| 0 | —CH₂—CH₂—CH₂— | | blocked 4-hydroxyphenylmethyl |
| 0 | —CH₂—CH₂—CH₂— | | blocked 3-indolylmethyl |
| 0 | —CH₂—CH₂—CH₂— | | 4-methoxyphenylmethyl |
| 0 | —CH₂—CH₂—CH₂— | | phenylethyl |
| 0 | methyl | methyl | hydrogen |
| 0 | n-butyl | n-butyl | methyl |
| 0 | benzyl | benzyl | 2-propyl |
| 0 | phenylethyl | phenylethyl | 2-butyl |
| 0 | blocked aminomethyl | blocked aminomethyl | benzyl |
| 0 | methyl-carbonylethyl | methyl-carbonylethyl | blocked 4-hydroxyphenylmethyl |
| 0 | PhtN-methyl | PhtN-methyl | blocked 3-indolylmethyl |
| 0 | PhtN-ethyl | PhtN-ethyl | 4-methoxyphenylmethyl |
| 0 | TsNH-methyl | TsNH-methyl | phenylethyl |
| 1 | —CH₂—CH₂—CH₂— | | hydrogen |
| 1 | —CH₂—CH₂—CH₂— | | methyl |
| 1 | —CH₂—CH₂—CH₂— | | 2-propyl |
| 1 | —CH₂—CH₂—CH₂— | | 2-butyl |
| 1 | —CH₂—CH₂—CH₂— | | benzyl |
| 1 | —CH₂—CH₂—CH₂— | | blocked 4-hydroxyphenylmethyl |
| 1 | —CH₂—CH₂—CH₂— | | blocked 3-indolylmethyl |
| 1 | —CH₂—CH₂—CH₂— | | 4-methoxyphenylmethyl |
| 1 | —CH₂—CH₂—CH₂— | | phenylethyl |
| 1 | methyl | methyl | hydrogen |
| 1 | n-butyl | n-butyl | methyl |
| 1 | benzyl | benzyl | 2-propyl |
| 1 | phenylethyl | phenylethyl | 2-butyl |
| 1 | blocked aminomethyl | blocked aminomethyl | benzyl |
| 1 | methyl-carbonylethyl | methyl-carbonylethyl | blocked 4-hydroxyphenylmethyl |
| 1 | PhtN-methyl | PhtN-methyl | blocked 3-indolylmethyl |
| 1 | PhtN-ethyl | PhtN-ethyl | 4-methoxyphenylmethyl |
| 1 | TsNH-methyl | TsNH-methyl | phenylethyl |

EXAMPLE 4

Preparation of BzNHCH₂S(CH₂)₂—(S-D-Leu)-Phe-NHMe

4A. Formula 7 Where n Is 0, $R^1$ and $R^2$ Are Hydrogen, $R^3$ Is 2-Methylpropyl, $R^4$ Is Benzyl and $R^6$ Is Methyl To a solution of 7.21 g of BzNHCH₂S(CH₂)₂—(S-D-Leu)-OH and 3.96 g of PheNHMe in 270 mL of 1,2-dimethoxyethane stirred at 5° C. was added 3.6 g of 1-hydroxybenzotriazole and 5.50 g of dicyclohexylcarbodiimide. The reaction mixture was stirred at 5° C. for 4 h, then at room temperature overnight. The resulting solid was filtered and washed with CH₂Cl₂. The filtrate was combined and evaporated under vacuum. The residue was dissolved in CH₂Cl₂ and washed with sat. NaHCO₃, 1N HCl, and water. The organic layer was dried over Na₂SO₄ and evaporated under vacuum. The residue was purified by flash chromatography (5% EtOAc in CH₂Cl₂) to give 8.24 g of BzNHCH₂S(CH₂)₂—(S-D-Leu)-Phe-NHMe at 78% yield. Characteristic analytical data are as follows: mp 74°–76° C.; $^1$H NMR (300 MHz, CDCl₃) δ7.99 (d, J=8 Hz, 1H), 7.85 (d, J=7 Hz, 2H), 7.55 (t, J=7 Hz, 1H), 7.46 (t, J=7 Hz, 2H), 7.18–7.31 (m, 6H), 6.28 (m, 1H), 5.03 (dd, J=9, 14 Hz, 1H), 4.68 (dr, J=7, 9 Hz, 1H), 4.28 (dd, J=5, 14 Hz, 1H), 3.37 (dd, J=6, 9 Hz, 1H), 3.14 (dd, J=7, 14 Hz, 1H), 3.00 (dd, J=9, 14 Hz, 1H), 2.82 (m, 2H), 2.74 (d, J=5 Hz, 3H), 2.63 (m, 2H), 1.68 (m, 1H), 1.34 (m, 2H), 0.78 (d, J=7 Hz, 3H), 0.77 (d, J=7 Hz, 3H).

4B. Preparation of the Corresponding (S-L-Leu) Isomer of Formula 7

Using the procedure described for the D-isomer, $BzNHCH_2S(CH_2)_2$—(S-L-Leu)-OH was coupled to PheNHMe to give a 42% yield of $BzNHCH_2S (CH_2)_2$—(S-L-Leu)-Phe-NHMe as a solid: mp 78°–80° C.; $^1$H NMR (300 MHz, $CDCl_3$) δ7.90 (d, J=7 Hz, 2H), 7.70 (br s, 1H, NH), 7.59 (br s, 1H, NH), 7.53 (t, J=7 Hz, 1H), 7.45 (t, J=7 Hz, 2H), 7.18–7.33 (m, 5H), 6.14 (br s, 1H, NH), 4.69 (dd, J=7, 14 Hz, 1H), 4.63 (br t, J=8 Hz, 1H), 4.29 (dd, J=5, 14 Hz, 1H), 3.31 (t, J=7 Hz, 1H), 3.16 (dd, J=7, 14 Hz, 1H), 3.05 (dd, J=8, 14 Hz, 1H), 2.53–2.84 (m, 4H), 2.68 (d, J=5 Hz, 3H), 1.58 (m, 2H), 1.36 (m, 1H), 0.83 (d, J=6 Hz, 3H), 0.79 (d, J=6 Hz, 3H).

4C. Formula 7 Varying $R^5$

By following the procedures described in Example 4A and substituting $BzNHCH_2S(CH_2)_2$—(S-D-Leu)-OH with other compounds of Formula 5 (where the $R^3$ substituents are as indicated in the table below) there are obtained the correspondingly substituted of compounds of Formula 7.

Formula 7

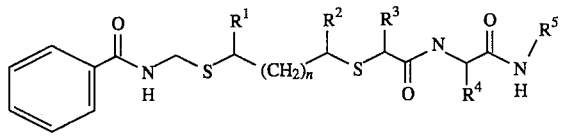

where $R^4$ is phenylmethyl, $R^5$ is $-CH(R^6) -C(O)NH_2$ and $R^6$ is methyl

| $R^3$ | Name |
|---|---|
| hydrogen | $BzNHCH_2S(CH_2)_2$ — (S — Gly) — Phe — NHMe |
| methyl | $BzNHCH_2S(CH_2)_2$ — (S — D — Ala) — Phe — NHMe |
| 2-propyl | $BzNHCH_2S(CH_2)_2$ — (S — D — Val) — Phe — NHMe |
| 2-butyl | $BzNHCH_2S(CH_2)_2$ — (S — D — Ile) — Phe — NHMe |
| benzyl | $BzNHCH_2S(CH_2)_2$ — (S — D — Phe) — Phe — NHMe |
| blocked 4-hydroxyphenylmethyl | $BzNHCH_2S(CH_2)_2$ — (S — D — Tyr) — Phe — NHMe |
| blocked 3-indolylmethyl | $BzNHCH_2S(CH_2)_2$ — (S — D — Trp) — Phe — NHMe |
| 4-methoxyphenylmethyl | $BzNHCH_2S(CH_2)_2$ — (S — D — Tyr — $OCH_3$) — Phe — NHMe |
| phenylethyl | $BzNHCH_2S(CH_2)_2$ — (S — D — Phet) — Phe — NHMe |

4D. Formula 7 Varying $R^3$

By following the procedures described in Example 4B and substituting $BzNHCH_2S(CH_2)_2$—(S-L-Leu)-OH with other compounds of Formula 5 (where the $R^3$ substituents are as indicated in the table below) there are obtained the correspondingly substituted of compounds of Formula 7.

Formula 7

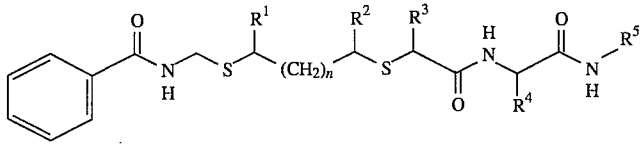

where $R^4$ is phenylmethyl, $R^5$ is $-CH(R^6)-C(O)NH_2$
and $R^6$ is methyl

| $R^3$ | Name |
|---|---|
| methyl | $BzNHCH_2S(CH_2)_2-$(S-L-Ala)$-$Phe$-$NHMe |
| 2-propyl | $BzNHCH_2S(CH_2)_2-$(S-L-Val)$-$Phe$-$NHMe |
| 2-butyl | $BzNHCH_2S(CH_2)_2-$(S-L-Ile)$-$Phe$-$NHMe |
| benzyl | $BzNHCH_2S(CH_2)_2-$(S-L-Phe)$-$Phe$-$NHMe |
| blocked 4-hydroxyphenylmethyl | $BzNHCH_2S(CH_2)_2-$(S-L-Tyr)$-$Phe$-$NHMe |
| blocked 3-indolylmethyl | $BzNHCH_2S(CH_2)_2-$(S-L-Trp)$-$Phe$-$NHMe |
| 4-methoxyphenylmethyl | $BzNHCH_2S(CH_2)_2-$(S-L-Tyr$-$OCH$_3$)$-$Phe$-$NHMe |
| phenylethyl | $BzNHCH_2S(CH_2)_2-$(S-L-Phet)$-$Phe$-$NHMe |

4E. Formula 7 Varying n, $R^1$, $R^2$ and $R^3$

By following the procedures described in Example 4A and substituting $BzNHCH_2S(CH_2)_2$—(S-D-Leu)-OH with other compounds of Formula 5 (e.g., compounds that are prepared according to Examples 3A-3F) there are obtained the correspondingly substituted of compounds of Formula 7 (where n, $R^1$, $R^2$ and $R^3$ are as indicated in the table below).

Formula 7

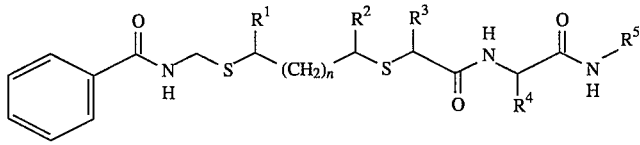

where $R^4$ is phenylmethyl, $R^5$ is $-CH(R^6)-C(O)NH_2$
and $R^6$ is methyl

| n | $R^1$ | $R^2$ | $R^3$ |
|---|---|---|---|
| 0 | | $-CH_2-CH_2-CH_2-$ | hydrogen |
| 0 | | $-CH_2-CH_2-CH_2-$ | methyl |
| 0 | | $-CH_2-CH_2-CH_2-$ | 2-propyl |
| 0 | | $-CH_2-CH_2-CH_2-$ | 2-butyl |
| 0 | | $-CH_2-CH_2-CH_2-$ | 2-methylpropyl |
| 0 | | $-CH_2-CH_2-CH_2-$ | blocked 4-hydroxy-phenylmethyl |
| 0 | | $-CH_2-CH_2-CH_2-$ | blocked 3-indolyl-methyl |
| 0 | | $-CH_2-CH_2-CH_2-$ | 4-methoxyphenylmethyl |
| 0 | | $-CH_2-CH_2-CH_2-$ | phenylethyl |
| 0 | methyl | methyl | hydrogen |
| 0 | n-butyl | n-butyl | methyl |
| 0 | benzyl | benzyl | 2-propyl |
| 0 | phenylethyl | phenylethyl | 2-butyl |
| 0 | blocked aminomethyl | blocked aminomethyl | benzyl |
| 0 | methyl-carbonylethyl | methyl-carbonylethyl | blocked 4-hydroxy-phenylmethyl |
| 0 | PhtN-methyl | PhtN-methyl | blocked 3-indolyl-methyl |
| 0 | PhtN-ethyl | PhtN-ethyl | 4-methoxyphenylmethyl |
| 0 | TsNH-methyl | TsNH-methyl | phenylethyl |
| 1 | | $-CH_2-CH_2-CH_2-$ | hydrogen |
| 1 | | $-CH_2-CH_2-CH_2-$ | methyl |
| 1 | | $-CH_2-CH_2-CH_2-$ | 2-propyl |
| 1 | | $-CH_2-CH_2-CH_2-$ | 2-butyl |
| 1 | | $-CH_2-CH_2-CH_2-$ | benzyl |
| 1 | | $-CH_2-CH_2-CH_2-$ | blocked 4-hydroxy-phenylmethyl |
| 1 | | $-CH_2-CH_2-CH_2-$ | blocked 3-indolyl-methyl |
| 1 | | $-CH_2-CH_2-CH_2-$ | 4-methoxyphenylmethyl |

-continued

Formula 7

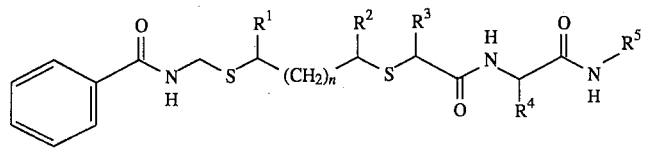

where R⁴ is phenylmethyl, R⁵ is —CH(R⁶)—C(O)NH₂
and R⁶ is methyl

| n | R¹ | R² | R³ |
|---|---|---|---|
| 1 | —CH₂—CH₂—CH₂— | | phenylethyl |
| 1 | methyl | methyl | hydrogen |
| 1 | n-butyl | n-butyl | methyl |
| 1 | benzyl | benzyl | 2-propyl |
| 1 | phenylethyl | phenylethyl | 2-butyl |
| 1 | blocked aminomethyl | blocked aminomethyl | benzyl |
| 1 | methyl-carbonylethyl | methyl-carbonylethyl | blocked 4-hydroxy-phenylmethyl |
| 1 | PhtN-methyl | PhtN-methyl | blocked 3-indolyl-methyl |
| 1 | PhtN-ethyl | PhtN-ethyl | 4-methoxyphenylmethyl |
| 1 | TsNH-methyl | TsNH-methyl | phenylethyl |

4F. Formula 7 Varying n, R¹, R², R³, R⁴, R⁵ and R⁶

By following the procedures described in Example 4A and substituting BzNHCH₂S(CH₂)₂—(S-D-Leu)-OH with other compounds of Formula 5 (e.g., compounds that are prepared according to Examples 3A–3F) and Phe-NHMe with other compounds of Formula 6 there are obtained the correspondingly substituted of compounds of Formula 7 (where n, R¹, R², R³, R⁴, R⁵ and R⁶ are as i the tables below).

Formula 7

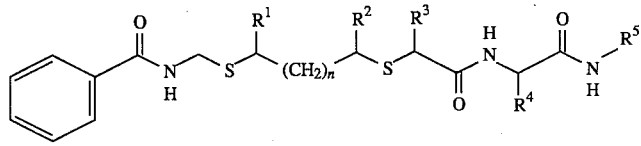

where R⁵ is methyl or benzyl

| n | R¹ | R² | R³ | R⁴ | R⁵ |
|---|---|---|---|---|---|
| 0 | —CH₂—CH₂—CH₂— | | hydrogen | phenylethyl | —CH₃ |
| 0 | —CH₂—CH₂—CH₂— | | methyl | 4-methoxy-phenyl-methyl | —Bn |
| 0 | —CH₂—CH₂—CH₂— | | 2-propyl | blocked 3-indolyl-methyl | —CH₃ |
| | —CH₂—CH₂—CH₂— | | 2-butyl | blocked 4-hydroxy-phenyl-methyl | —Bn |
| 0 | —CH₂—CH₂—CH₂— | | 2-methyl-propyl | benzyl | —CH₃ |
| 0 | —CH₂—CH₂—CH₂— | | blocked 4-hydroxy-phenylmethyl | blocked 4-imidazoyl-methyl | —Bn |
| 0 | —CH₂—CH₂—CH₂— | | blocked 3-indolylmethyl | blocked 3-guanyl-propyl | —CH₃ |
| 0 | —CH₂—CH₂—CH₂— | | 4-methoxy-phenylmethyl | blocked 4-aminobutyl | —Bn |
| 0 | —CH₂—CH₂—CH₂— | | phenylethyl | 2-methyl-propyl | —CH₃ |
| 0 | methyl | methyl | hydrogen | 2-butyl | —Bn |
| 0 | n-butyl | n-butyl | methyl | 2-propyl | —CH₃ |
| 0 | benzyl | benzyl | 2-propyl | methyl | —Bn |
| 0 | phenylethyl | phenylethyl | 2-butyl | hydrogen | —CH₃ |

-continued

Formula 7

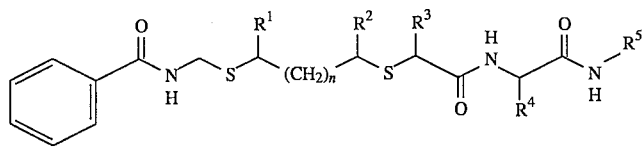

where $R^5$ is methyl or benzyl

| n | $R^1$ | $R^2$ | $R^3$ | $R^4$ | $R^5$ |
|---|---|---|---|---|---|
| 0 | blocked aminomethyl | blocked aminomethyl | benzyl | hydrogen | —Bn |
| 0 | methylcarbonylethyl | methylcarbonylethyl | blocked 4-hydroxyphenylmethyl | methyl | —$CH_3$ |
| 0 | PhtN-methyl | PhtN-methyl | blocked 3-indolylmethyl | 2-propyl | —Bn |
|  |  |  |  |  | —$CH_3$ |
| 0 | PhtN-ethyl | PhtN-ethyl | 4-methoxyphenylmethyl | 2-butyl | —$CH_3$ |
| 0 | TsNH-methyl | TsNH-methyl | phenylethyl | 2-methylpropyl | —Bn |
| 1 | —$CH_2$—$CH_2$—$CH_2$— | | hydrogen | blocked 4-aminobutyl | —$CH_3$ |
| 1 | —$CH_2$—$CH_2$—$CH_2$— | | methyl | blocked 3-guanylpropyl | —Bn |
| 1 | —$CH_2$—$CH_2$—$CH_2$— | | 2-propyl | blocked 4-imidazoylmethyl | —$CH_3$ |
| 1 | —$CH_2$—$CH_2$—$CH_2$— | | 2-butyl | benzyl | —Bn |
| 1 | —$CH_2$—$CH_2$—$CH_2$— | | benzyl | blocked 4-hydroxyphenylmethyl | —$CH_3$ |
| 1 | —$CH_2$—$CH_2$—$CH_2$— | | blocked 4-hydroxyphenylmethyl | blocked 3-indolylmethyl | —Bn |
| 1 | —$CH_2$—$CH_2$—$CH_2$— | | blocked 3-indolylmethyl | 4-methoxyphenylmethyl | —$CH_3$ |
| 1 | —$CH_2$—$CH_2$—$CH_2$— | | 4-methoxyphenylmethyl | phenylethyl | —Bn |
| 1 | —$CH_2$—$CH_2$—$CH_2$— | | phenylethyl | phenylethyl | —$CH_3$ |
| 1 | methyl | methyl | hydrogen | 4-methoxyphenylmethyl | —Bn |
| 1 | n-butyl | n-butyl | methyl | blocked 3-indolylmethyl | —$CH_3$ |
| 1 | benzyl | benzyl | 2-propyl | blocked 4-hydroxyphenylmethyl | —Bn |
| 1 | phenylethyl | phenylethyl | 2-butyl | benzyl | —$CH_3$ |
| 1 | blocked aminomethyl | blocked aminomethyl | benzyl | blocked 4-imidazoylmethyl | —Bn |
| 1 | methylcarbonylethyl | methylcarbonylethyl | blocked 4-hydroxyphenylmethyl | blocked 3-guanylpropyl | —$CH_3$ |
| 1 | PhtN-methyl | PhtN-methyl | blocked 3-indolylmethyl | blocked 4-aminobutyl | —Bn |
| 1 | PhtN-ethyl | PhtN-ethyl | 4-methoxyphenylmethyl | 2-methylpropyl | —$CH_3$ |
| 1 | TsNH-methyl | TsNH-methyl | phenylethyl | 2-butyl | —Bn |

Formula 7

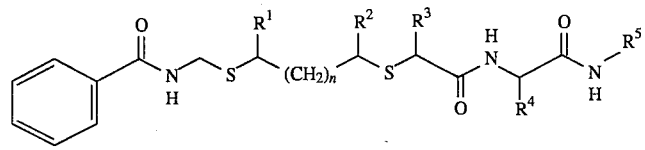

where $R^5$ is $-CH(R^6)-C(O)NH_2$

| n | $R^1$ | $R^2$ | $R^3$ | $R^4$ | $R^6$ |
|---|---|---|---|---|---|
| 0 | $-CH_2-CH_2-CH_2-$ | | hydrogen | phenylethyl | hydrogen |
| 0 | $-CH_2-CH_2-CH_2-$ | | methyl | 4-methoxy-phenylmethyl | 2-propyl |
| 0 | $-CH_2-CH_2-CH_2-$ | | 2-propyl | blocked 3-indolyl-methyl | methyl |
| 0 | $-CH_2-CH_2-CH_2-$ | | 2-butyl | blocked 4-hydroxy-phenylmethyl | 2-butyl |
| 0 | $-CH_2-CH_2-CH_2-$ | | 2-methyl-propyl | benzyl | 2-methyl-propyl |
| 0 | $-CH_2-CH_2-CH_2-$ | | blocked 4-hydroxy-phenylmethyl | blocked 4-imidazoyl-methyl | blocked 4-aminobutyl |
| 0 | $-CH_2-CH_2-CH_2-$ | | blocked 3-indolyl-methyl | blocked 3-guanylpropyl | blocked 3-guanylpropyl |
| 0 | $-CH_2-CH_2-CH_2-$ | | 4-methoxy-phenylmethyl | blocked 4-aminobutyl | 2-imidazoyl-methyl |
| 0 | $-CH_2-CH_2-CH_2-$ | | phenylethyl | 2-methyl-propyl | hydroxy-methyl |
| 0 | methyl | methyl | hydrogen | 2-butyl | 1-hydroxy-ethyl |
| 0 | n-butyl | n-butyl | methyl | 2-propyl | thiolmethyl |
| 0 | benzyl | benzyl | 2-propyl | methyl | methylthio-ethyl |
| 0 | phenylethyl | phenylethyl | 2-butyl | hydrogen | methylthio-ethyl |
| 0 | blocked aminomethyl | blocked aminomethyl | benzyl | hydrogen | thiolmethyl |
| 0 | methyl-carbonyl-ethyl | methyl-carbonyl-ethyl | blocked 4-hydroxy-phenylmethyl | methyl | 1-hydroxy-ethyl |
| 0 | PhtN-methyl | PhtN-methyl | blocked 3-indolyl-methyl | 2-propyl | hydroxy-methyl |
| 0 | PhtN-ethyl | PhtN-ethyl | 4-methoxy-phenylmethyl | 2-butyl | 2-imidazoyl-methyl |
| 0 | TsNH-methyl | TsNH-methyl | phenylethyl | 2-methyl-propyl | blocked 3-guanylpropyl |
| 1 | $-CH_2-CH_2-CH_2-$ | | hydrogen | blocked 4-aminobutyl | blocked 4-aminobutyl |
| 1 | $-CH_2-CH_2-CH_2-$ | | methyl | blocked 3-guanylpropyl | 2-methyl-propyl |
| 1 | $-CH_2-CH_2-CH_2-$ | | 2-propyl | blocked 4-imidazoyl-methyl | 2-butyl |
| 1 | $-CH_2-CH_2-CH_2-$ | | 2-butyl | benzyl | methyl |
| 1 | $-CH_2-CH_2-CH_2-$ | | benzyl | blocked 4-hydroxy-phenylmethyl | 2-propyl |
| 1 | $-CH_2-CH_2-CH_2-$ | | blocked 4-hydroxy-phenylmethyl | blocked 3-indolylmethy | hydrogen |
| 1 | $-CH_2-CH_2-CH_2-$ | | blocked 3-indolyl-methyl | 4-methoxy-phenylmethyl | methylthio-ethyl |
| 1 | $-CH_22-CH_2-CH_2-$ | | 4-methoxy-phenylmethyl | phenylethyl | thiolmethyl |
| 1 | $-CH_2-CH_2-CH_2-$ | | phenylethyl | phenylethyl | 1-hydroxy-ethyl |
| 1 | methyl | methyl | hydrogen | 4-methoxy-phenylmethyl | hydroxy-methyl |
| 1 | n-butyl | n-butyl | methyl | blocked 3-indolylmethyl | 2-imidazoyl-methyl |
| 1 | benzyl | benzyl | 2-propyl | blocked 4-hydroxy- | blocked 3-guanylpropyl |

-continued

Formula 7

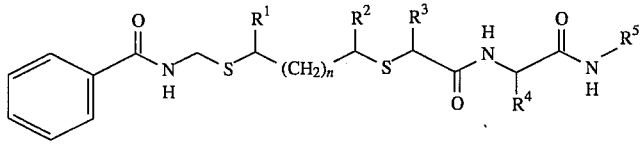

where $R^5$ is $-CH(R^6)-C(O)NH_2$

| n | $R^1$ | $R^2$ | $R^3$ | $R^4$ | $R^6$ |
|---|---|---|---|---|---|
| 1 | phenylethyl | phenylethyl | 2-butyl | phenylmethyl benzyl | blocked 4-aminobutyl |
| 1 | blocked aminomethyl | blocked aminomethyl | benzyl | blocked 4-imidazoyl-methyl | 2-methyl-propyl |
| 1 | methyl-carbonyl-ethyl | methyl-carbonyl-ethyl | blocked 4-hydroxy-phenylmethyl | blocked 3-guanylpropyl | 2-butyl |
| 1 | PhtN-methyl | PhtN-methyl | blocked 3-indolyl-methyl | blocked 4-aminobutyl | methyl |
| 1 | PhtN-ethyl | PhtN-ethyl | 4-methoxy-phenylmethyl | 2-methyl-propyl | 2-propyl |
| 1 | TsNH-methyl | TsNH-methyl | phenylethyl | 2-butyl | hydrogen |

EXAMPLE 5

Preparation of $HS(CH_2)_2$—(S-D-Leu)-Phe-NHMe

5A. Formula I Where n Is 0, $R^1$ and $R^2$ Are Hydrogen, $R^3$ Is 2-Methylpropyl and $R^4$ Is Phe-NHMe To a solution of 4.14 g of $BzNHCH_2S(CH_2)_2$—(S-D-Leu)-Phe-NHMe in 150 mL of MeOH and 20 mL of water was added 2.63 g of $Hg(OAc)_2$. The mixture was stirred at room temperature for 1 h, then $H_2S$ gas was bubbled through the mixture for 15 min. Water was added and the precipitate was removed by filtration. The filtrate was extracted thoroughly with EtOAc and the combined extract was washed with water and dried over $Na_2SO_4$. The solvent was evaporated under vacuum and the residue was purified by flash chromatography (5% EtOAc in $CH_2Cl_2$) to give 2.18 g of $HS(CH_2)_2$—(S-D-Leu)-Phe-NHMe as a solid at 72% yield. Characteristic analytical data are as follows: mp 169°–171° C. (hexane-EtOAc); $^1H$ NMR (300 MHz, $CDCl_3$) δ7.20–7.34 (m, 5H), 7.00 (br d, J=8 Hz, 1H, NH), 5.90 (br s, 1H, NH), 4.60 (q, J=8 Hz, 1H), 3.27 (dd, J=7, 8 Hz, 1H), 3.15 (dd, J=7, 14 Hz, 1H), 3.07 (dd, J=8, 14 Hz, 1H), 2.75 (d, J=5 Hz, 3H), 2.55 (m, 2H), 2.43 (m, 2H), 1.62–1.73 (m, 2H), 1.59 (t, J=8 Hz, 1H, S 1.40–1.52 (m, 1H), 0.89 (d, J=7 Hz, 3H), 0.88 (d, J=7 Hz, 3H); $^{13}C$ NMR (75 MHz, $CDCl_3$) δ172.9 (C), 171.6 (C), 136.9 (C), 129.4 (CH), 128.9 (CH), 127.2 (CH), 54.5 (CH), 47.9 (CH), 41.2 ($CH_2$), 37.8 ($CH_2$), 35.0 ($CH_2$), 26.0 ($CH_3$), 25.8 ($CH_3$), 24.2 ($CH_2$), 22.3 ($CH_3$), 21.7 ($CH_3$); $[\alpha]_D^{25}$ +39.7° (c=0.32, MeOH). Anal. Calcd for $C_{18}H_{28}N_2O_2S_2$: C, 58.66; H, 7.66; N, 7.60; S, 17.40. Found: C, 58.76; H, 7.69; N, 7.54; S, 17.46.

5B. Preparation of the Corresponding (S-L-Leu) Isomer of Formula I

The $BzNHCH_2S(CH_2)_2$—(S-L-Leu)-Phe-NHMe was deblocked as described above for the D-isomer to afford $HS(CH_2)_2$—(S-L-Leu)-Phe-NHMe as a solid (48% yield): mp 156°–158° C.; $^1H$ NMR (300 MHz, $CDCl_3$) δ7.19–7.32 (m, 6H), 6.19 (br m, 1H, NH), 4.64 (q, J=8 Hz, 1H), 3.32 (t, J=8 Hz, 1H), 3.11 (dd, J=7, 14 Hz, 1H), 3.05 (dd, J=8, 14 Hz, 1H), 2.75 (d, J=5 Hz, 3H), 2.60–2.70 (m, 4H), 1.47– 1.68 (m, 3H), 1.32–1.44 (m, 1H), 0.87 (d, J=6 Hz, 3H), 0.83 (d, J=6 Hz, 3H $[\alpha]_D^{25}$ -61° (c=0.10, MeOH).

5C. Formula I Varying $R^3$

By following the procedures described in Example 5A and substituting $BzNHCH_2S(CH_2)_2$—(S-D-Leu)-Phe-NHMe with other compounds of Formula 7 (where the $R^5$ substituents are as indicated in the table below) there are obtained the correspondingly substituted of compounds of Formula I.

Formula I

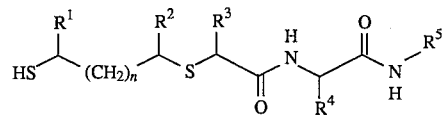

where $R^4$ is phenylmethyl and $R^5$ is methyl

| $R^3$ | Name |
|---|---|
| hydrogen | $HS(CH_2)_2$—(S—Gly)—Phe—NHMe |
| methyl | $HS(CH_2)_2$—(S-D-Ala)—Phe—NHMe |
| 2-propyl | $HS(CH_2)_2$—(S-D-Val)—Phe—NHMe |
| 2-butyl | $HS(CH_2)_2$—(S-D-Ile)—Phe—NHMe |
| benzyl | $HS(CH_2)_2$—(S-D-Phe)—Phe—NHMe |
| 4-hydroxy-phenylmethyl | $HS(CH_2)_2$—(S-D-Tyr)—Phe—NHMe |
| 3-indolyl-methyl | $HS(CH_2)_2$—(S-D-Trp)—Phe—NHMe |
| 4-methoxy-phenylmethyl | $HS(CH_2)_2$—(S-D-Tyr—$OCH_3$)—Phe—NHMe |
| phenylethyl | $HS(CH_2)_2$—(S-D-Phet)—Phe—NHMe |

5D. Formula I Varying $R^3$

By following the procedures described in Example 5B and substituting $BzNHCH_2S(CH_2)_2$—(S-L-Leu)-Phe-NHMe with other compounds of Formula 7 (where the substituents are as indicated in the table below) there are obtained the correspondingly substituted of compounds of Formula I.

Formula I

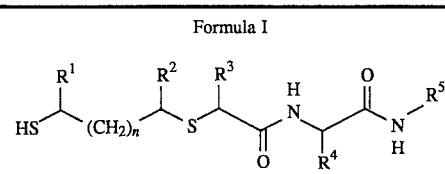

where $R^4$ is phenylmethyl and $R^5$ is methyl

| $R^3$ | Name |
|---|---|
| methyl | $HS(CH_2)_2$—(S-L-Ala)—Phe—NHMe |
| 2-propyl | $HS(CH_2)_2$—(S-L-Val)—phe—NHMe |
| 2-butyl | $HS(CH_2)_2$—(S-L-Ile)—Phe—NHMe |
| benzyl | $HS(CH_2)_2$—(S-L-Phe)—Phe—NHMe |
| 4-hydroxyphenylmethyl | $HS(CH_2)_2$—(S-L-Tyr)—Phe—NHMe |
| 3-indolylmethyl | $HS(CH_2)_2$—(S-L-Trp)—Phe—NHMe |
| 4-methoxyphenylmethyl | $HS(CH_2)_2$—(S-L-Tyr—$OCH_3$)—Phe—NHMe |
| phenylethyl | $HS(CH_2)_2$—(S-L-Phet)—Phe—NHMe |

5E. Formula I Varying n, $R^1$, $R^2$ and $R^3$

By following the procedures described in Example 5A and substituting $BzNHCH_2S(CH_2)_2$—(S-D-Leu)-Phe-NHMe with other compounds of Formula 7 (e.g., compounds that are prepared according to Examples 4A–4F) there are obtained the correspondingly substituted of compounds of Formula I (where n, $R^1$, $R^2$, $R^3$, $R^4$, $R^5$, and $R^6$ are as indicated in the tables below).

Formula I

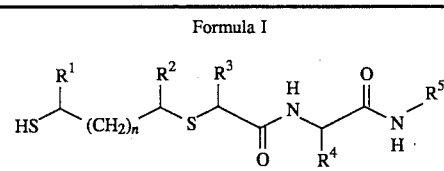

where $R^4$ is phenylmethyl and $R^5$ is methyl

| n | $R^1$ | $R^2$ | $R^3$ |
|---|---|---|---|
| 0 | | —$CH_2$—$CH_2$—$CH_2$— | hydrogen |
| 0 | | —$CH_2$—$CH_2$—$CH_2$— | methyl |
| 0 | | —$CH_2$—$CH_2$—$CH_2$— | 2-propyl |
| 0 | | —$CH_2$—$CH_2$—$CH_2$— | 2-butyl |
| 0 | | —$CH_2$—$CH_2$—$CH_2$— | 2-methylpropyl |
| 0 | | —$CH_2$—$CH_2$—$CH_2$— | 4-hydroxyphenylmethyl |
| 0 | | —$CH_2$—$CH_2$—$CH_2$— | 3-indolylmethyl |
| 0 | | —$CH_2$—$CH_2$—$CH_2$— | 4-methoxyphenylmethyl |
| 0 | | —$CH_2$—$CH_2$—$CH_2$— | phenylethyl |
| 0 | methyl | methyl | hydrogen |
| 0 | n-butyl | n-butyl | methyl |
| 0 | benzyl | benzyl | 2-propyl |
| 0 | phenylethyl | phenylethyl | 2-butyl |
| 0 | aminomethyl | aminomethyl | benzyl |
| 0 | methyl-carbonylethyl | methyl-carbonylethyl | 4-hydroxyphenylmethyl |
| 0 | PhtN-methyl | PhtN-methyl | 3-indolylmethyl |
| 0 | PhtN-ethyl | PhtN-ethyl | 4-methoxyphenylmethyl |
| 0 | TsNH-methyl | TsNH-methyl | phenylethyl |
| 1 | | —$CH_2$—$CH_2$—$CH_2$— | hydrogen |
| 1 | | —$CH_2$—$CH_2$—$CH_2$— | methyl |
| 1 | | —$CH_2$—$CH_2$—$CH_2$— | 2-propyl |
| 1 | | —$CH_2$—$CH_2$—$CH_2$— | 2-butyl |
| 1 | | —$CH_2$—$CH_2$—$CH_2$— | benzyl |
| 1 | | —$CH_2$—$CH_2$—$CH_2$— | 4-hydroxyphenylmethyl |
| 1 | | —$CH_2$—$CH_2$—$CH_2$— | 3-indolylmethyl |
| 1 | | —$CH_2$—$CH_2$—$CH_2$— | 4-methoxyphenylmethyl |
| 1 | | —$CH_2$—$CH_2$—$CH_2$— | phenylethyl |
| 1 | methyl | methyl | hydrogen |
| 1 | n-butyl | n-butyl | methyl |
| 1 | benzyl | benzyl | 2-propyl |

-continued

Formula I

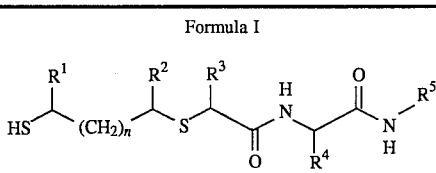

where $R^4$ is phenylmethyl and $R^5$ is methyl

| n | $R^1$ | $R^2$ | $R^3$ |
|---|---|---|---|
| 1 | phenylethyl | phenylethyl | 2-butyl |
| 1 | aminomethyl | aminomethyl | benzyl |
| 1 | methyl-carbonylethyl | methyl-carbonylethyl | 4-hydroxyphenylmethyl |
| 1 | PhtN-methyl | PhtN-methyl | 3-indolylmethyl |
| 1 | PhtN-ethyl | PhtN-ethyl | 4-methoxyphenylmethyl |
| 1 | TsNH-methyl | TsNH-methyl | phenylethyl |

5F. Formula I Varying n, $R^1$, $R^2$, $R^3$, $R^4$, $R^5$ and $R^6$

By following the procedures described in Example 5A and substituting $BzNHCH_2S(CH_2)_2$-(S-D-Leu)-Phe-NHMe with other compounds of Formula 7 (e.g., compounds that are prepared according to Examples 4A–4F) there are obtained the correspondingly substituted compounds of Formula I (where n, $R^1$, $R^2$, $R^3$, $R^4$, $R^5$ and $R^6$ are as indicated in the tables below).

Formula I

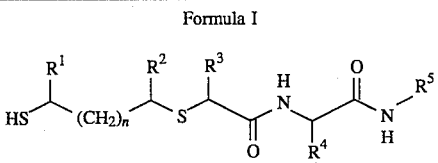

where $R^5$ is methyl or phenylmethyl

| n | $R^1$ | $R^2$ | $R^3$ | $R^4$ | $R^5$ |
|---|---|---|---|---|---|
| 0 | —$CH_2$—$CH_2$—$CH_2$— | | hydrogen | phenylethyl | —$CH_3$ |
| 0 | —$CH_2$—$CH_2$—$CH_2$— | | methyl | 4-methoxyphenylmethyl | —Bn |
| 0 | —$CH_2$—$CH_2$—$CH_2$— | | 2-propyl | 3-indolylmethyl | —$CH_3$ |
| 0 | —$CH_2$—$CH_2$—$CH_2$— | | 2-butyl | 4-hydroxyphenylmethyl | —Bn |
| 0 | —$CH_2$—$CH_2$—$CH_2$— | | 2-methylpropyl | benzyl | —$CH_3$ |
| 0 | —$CH_2$—$CH_2$—$CH_2$— | | 4-hydroxyphenylmethyl | 4-imidazoylmethyl | —Bn |
| 0 | —$CH_2$—$CH_2$—$CH_2$— | | 3-indolylmethyl | 3-guanylpropyl | —$CH_3$ |
| 0 | —$CH_2$—$CH_2$—$CH_2$— | | 4-methoxyphenylmethyl | 4-aminobutyl | —Bn |
| 0 | —$CH_2$—$CH_2$—$CH_2$— | | phenylethyl | 2-methylpropyl | —$CH_3$ |
| 0 | methyl | methyl | hydrogen | 2-butyl | —Bn |

Formula I

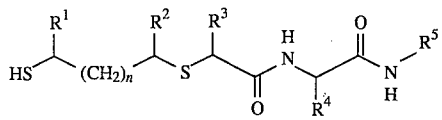

where R⁵ is methyl or phenylmethyl

| n | R¹ | R² | R³ | R⁴ | R⁵ |
|---|---|---|---|---|---|
| 0 | n-butyl | n-butyl | methyl | 2-propyl | —CH₃ |
| 0 | benzyl | benzyl | 2-propyl | methyl | —Bn |
| 0 | phenylethyl | phenylethyl | 2-butyl | hydrogen | —CH₃ |
| 0 | aminomethyl | aminomethyl | benzyl | hydrogen | —Bn |
| 0 | methyl-carbonylethyl | methyl-carbonylethyl | 4-hydroxy-phenylmethyl | methyl | —CH₃ |
| 0 | PhtN-methyl | PhtN-methyl | 3-indolylmethyl | 2-propyl | —Bn |
| 0 | PhtN-ethyl | PhtN-ethyl | 4-methoxy-phenylmethyl | 2-butyl | —CH₃ |
| 0 | TsNH-methyl | TsNH-methyl | phenylethyl | 2-methyl-propyl | —Bn |
| 1 | —CH₂—CH₂—CH₂— | | hydrogen | 4-aminobutyl | —CH₃ |
| 1 | —CH₂—CH₂—CH₂— | | methyl | 3-guanyl-propyl | —Bn |
| 1 | —CH₂—CH₂—CH₂— | | 2-propyl | 4-imidazoyl-methyl | —CH₃ |
| 1 | —CH₂—CH₂—CH₂— | | 2-butyl | benzyl | —Bn |
| 1 | —CH₂—CH₂—CH₂— | | benzyl | 4-hydroxy-phenylmethyl | —CH₃ |
| 1 | —CH₂—CH₂—CH₂— | | 4-hydroxy-phenylmethyl | 3-indolyl-methyl | —Bn |
| 1 | —CH₂—CH₂—CH₂— | | 3-indolylmethyl | 4-methoxy-phenylmethyl | —CH₃ |
| 1 | —CH₂—CH₂—CH₂— | | 4-methoxy-phenylmethyl | phenylethyl | —Bn |
| 1 | —CH₂—CH₂—CH₂— | | phenylethyl | phenylethyl | —CH₃ |
| 1 | methyl | methyl | hydrogen | 4-methoxy-phenylmethyl | —Bn |
| 1 | n-butyl | n-butyl | methyl | 3-indolyl-methyl | —CH₃ |
| 1 | benzyl | benzyl | 2-propyl | 4-hydroxy-phenylmethyl | —Bn |
| 1 | phenylethyl | phenylethyl | 2-butyl | benzyl | —CH₃ |
| 1 | aminomethyl | aminomethyl | benzyl | 4-imidazoyl-methyl | —Bn |
| 1 | methyl-carbonylethyl | methyl-carbonylethyl | 4-hydroxy-phenylmethyl | 3-guanyl-propyl | —CH₃ |
| 1 | PhtN-methyl | PhtN-methyl | 3-indolylmethyl | 4-aminobutyl | —Bn |
| 1 | PhtN-ethyl | PhtN-ethyl | 4-methoxy-phenylmethyl | 2-methyl-propyl | —CH₃ |
| 1 | TsNH-methyl | TsNH-methyl | phenylethyl | 2-butyl | —Bn |

Formula I

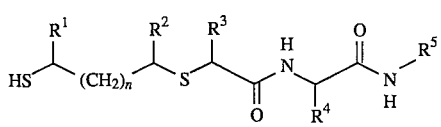

where R⁵ is —CH(R⁶)—C(O)NH₂

| n | R¹ | R² | R³ | R⁴ | R⁶ |
|---|---|---|---|---|---|
| 0 | —CH₂—CH₂—CH₂— | | hydrogen | phenylethyl | hydrogen |
| 0 | —CH₂—CH₂—CH₂— | | methyl | 4-methoxy-phenylmethyl | 2-propyl |
| | —CH₂—CH₂—CH₂— | | 2-propyl | 3-indolyl-methyl | methyl |
| 0 | —CH₂—CH₂—CH₂— | | 2-butyl | 4-hydroxy-phenylmethyl | 2-butyl |
| 0 | —CH₂—CH₂—CH₂— | | 2-methyl- | benzyl | 2-methyl- |

-continued

Formula I

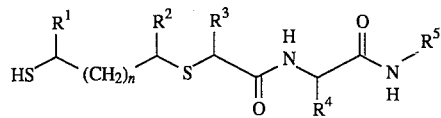

where $R^5$ is $-CH(R^6)-C(O)NH_2$

| n | $R^1$ | $R^2$ | $R^3$ | $R^4$ | $R^6$ |
|---|---|---|---|---|---|
| 0 | $-CH_2-CH_2-CH_2-$ | | 4-hydroxy-phenylmethyl | 4-imidazoyl-methyl | propyl 4-aminobutyl |
| 0 | $-CH_2-CH_2-CH_2-$ | | 3-indolyl-methyl | 3-guanyl-propyl | 3-guanyl-propyl |
| 0 | $-CH_2-CH_2-CH_2-$ | | 4-methoxy-phenylmethyl | 4-aminobutyl | 2-imidazoyl-methyl |
| 0 | $-CH_2-CH_2-CH_2-$ | | phenylethyl | 2-methyl-propyl | hydroxy-methyl |
| 0 | methyl | methyl | hydrogen | 2-butyl | 1-hydroxy-ethyl |
| 0 | n-butyl | n-butyl | methyl | 2-propyl | thiolmethyl |
| 0 | benzyl | benzyl | 2-propyl | methyl | methylthio-ethyl |
| 0 | phenylethyl | phenylethyl | 2-butyl | hydrogen | methylthio-ethyl |
| 0 | aminomethyl | aminomethyl | benzyl | hydrogen | thiolmethyl |
| 0 | methyl-carbonyl-ethyl | methyl-carbonyl-ethyl | 4-hydroxy-phenylmethyl | methyl | 1-hydroxy-ethyl |
| 0 | PhtN-methyl | PhtN-methyl | 3-indolyl-methyl | 2-propyl | hydroxy-methyl |
| 0 | PhtN-ethyl | PhtN-ethyl | 4-methoxy-phenylmethyl | 2-butyl | 2-imidazoyl-methyl |
| 0 | TsNH-methyl | TsNH-methyl | phenylethyl | 2-methyl-propyl | 3-guanyl-propyl |
| 1 | $-CH_2-CH_2-CH_2-$ | | hydrogen | 4-aminobutyl | 4-aminobutyl |
| 1 | $-CH_2-CH_2-CH_2-$ | | methyl | 3-guanyl-propyl | 2-methyl-propyl |
| 1 | $-CH_2-CH_2-CH_2-$ | | 2-propyl | 4-imidazoyl-methyl | 2-butyl |
| 1 | $-CH_2-CH_2-CH_2-$ | | 2-butyl | benzyl | methyl |
| 1 | $-CH_2-CH_2-CH_2-$ | | benzyl | 4-hydroxy-phenylmethyl | 2-propyl |
| 1 | $-CH_2-CH_2-CH_2-$ | | 4-hydroxy-phenylmethyl | 3-indolyl-methyl | hydrogen |
| 1 | $-CH_2-CH_2-CH_2-$ | | 3-indolyl-methyl | 4-methoxy-phenylmethyl | methylthio-ethyl |
| 1 | $-CH_2-CH_2-CH_2-$ | | 4-methoxy-phenylmethyl | phenylethyl | thiolmethyl |
| 1 | $-CH_2-CH_2-CH_2-$ | | phenylethyl | phenylethyl | 1-hydroxy-ethyl |
| 1 | methyl | methyl | hydrogen | 4-methoxy-phenylmethyl | hydroxy-methyl |
| 1 | n-butyl | n-butyl | methyl | 3-indolyl-methyl | 2-imidazoyl-methyl |
| 1 | benzyl | benzyl | 2-propyl | 4-hydroxy-phenylmethyl | 3-guanyl-propyl |
| 1 | phenylethyl | phenylethyl | 2-butyl | benzyl | 4-aminobutyl |
| 1 | aminomethyl | aminomethyl | benzyl | 4-imidazoyl-methyl | 2-methyl-propyl |
| 1 | methyl-carbonyl-ethyl | methyl-carbonyl-ethyl | 4-hydroxy-phenylmethyl | 3-guanyl-propyl | 2-butyl |
| 1 | PhtN-methyl | PhtN-methyl | 3-indolyl-methyl | 4-aminobutyl | methyl |
| 1 | PhtN-ethyl | PhtN-ethyl | 4-methoxy-phenylmethyl | 2-methyl-propyl | 2-propyl |
| 1 | TsNH-methyl | TsNH-methyl | phenylethyl | 2-butyl | hydrogen |

EXAMPLE 6

Preparation of (2R)-2-Bromopropanoic Acid

6A. Formula 9 Where $R^1$ Is Methyl and X Is Bromo

To a stirred solution of 5.00 g of D-Ala, 23.4 g of KBr in 37 mL of water and 11 mL of conc. sulfuric acid at −8° C. was added a solution of 5.14 g of NaNO$_2$ in 2 mL of water over a period of 1 h. Stirring was continued for 1 h at the same temperature, the reaction mixture was then extracted with CH$_2$Cl$_2$. The organic layer was washed with water, dried over Na$_2$SO$_4$ and evaporated under vacuum to give 3.16 g of (2R)-2-bromopropanoic acid as an oil at 41% yield. Characteristic analytical data are as follows: $^1$H NMR (300 MHz, CDCl$_3$) δ4.41 (q, J=7 Hz, 1H), 1.86 (d, J=7 Hz, 3H); $[\alpha]_D^{25}$ +32.6° (c= 2.10, MeOH).

6B. Preparation of the Corresponding (S) Isomer of Formula 9

By following the procedure described in Example 6A and substituting L-Ala for D-Ala, (2S)-2-Bromopropanoic acid was obtained in 43% yield. Characteristic analytical data are as follows: $[\alpha]_D^{25}$ −31.8° (c=2.10, MeOH).

6C. Formula 9 Varying $R^1$

By following the procedures described in Example 6A and substituting D-Ala with other compounds of Formula 8 and KBr with other halo salts there are obtained the correspondingly substituted compounds of Formula 9 (where $R^1$ is as indicated in the table below).

Formula 9

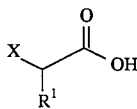

| X | $R^1$ | Name |
|---|---|---|
| Cl | hydrogen | 2-chloroethanoic acid |
| I | 2-propyl | (2R)-2-iodo-3-methylbutanoic acid |
| Br | 2-methylpropyl | (2R)-2-bromo-4-methylpentanoic acid |
| Cl | 2-butyl | (2R)-2-chloro-3-methylpentanoic acid |
| Br | blocked aminobutyl | (2R)-6-amino-2-bromohexanoic acid |
| Cl | carbamoylmethyl | (2R)-3-carbamoyl-2-chloropropanoic acid |

6D. Formula 9 Varying $R^1$

By following the procedures described in Example 6A and substituting L-Ala with other compounds of Formula 8 and KBr with other halo salts there are obtained the correspondingly substituted compounds of Formula 9 (where $R^1$ is as indicated in the table below).

Formula 9

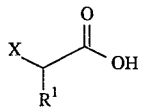

| X | $R^1$ | Name |
|---|---|---|
| I | 2-propyl | (2S)-2-iodo-3-methylbutanoic acid |
| Br | 2-methylpropyl | (2S)-2-bromo-4-methylpentanoic acid |
| Cl | 2-butyl | (2S)-2-chloro-3-methylpentanoic acid |
| Br | blocked aminobutyl | (2S)-6-amino-2-bromohexanoic acid |

-continued

Formula 9

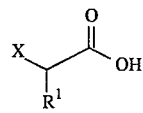

| X | $R^1$ | Name |
|---|---|---|
| Cl | carbamoylmethyl | (2S)-3-carbamoyl-2-chloropropanoic acid |

EXAMPLE 7

Preparation of (2S)-2-(Tert-Butylthio)Propanoic Acid

7A. Formula 10 Where $R^1$ Is Methyl

To a solution of 483 mg of Na in 10 mL of EtOH was added 10 mL of tert-butylthiol with stirring at room temperature under nitrogen. After 10 min a solution of 1.53 g of (2R)-2-bromopropanoic acid in 3 mL of EtOH was added and the stirring was continued at room temperature for 3 h. The reaction mixture was poured into water and was acidified with acetic acid and extracted with CH$_2$Cl$_2$. The organic layer was dried over Na$_2$SO$_4$ and was evaporated under water aspirator vacuum using a trap containing bleach to give 1.48 g of (2S)-2-(tert-butylthio)propanoic acid as an oil at 92% yield. Characteristic analytical data are as follows: $^1$H NMR (300 MHz, CDCl$_3$) δ3.44 (q, J=7 Hz, 1H), 1.49 (d, J=7 Hz, 3H), 1.37 (s, 9H).

7B. Preparation of the Corresponding (R) Isomer of Formula 10

By the following procedure described in Example 7A and substituting (2R)-2-bromopropanoic acid with (2S)-2-bromopropanoic acid, (2R)-2-(tert-butylthio)propanoic acid was obtained at 93% yield.

7C. Formula 10 Varying $R^1$

By following the procedures described in Example 7A and substituting (2R)-2-bromopropanoic acid with other compounds of Formula 9 there are obtained the correspondingly substituted compounds of Formula 10 (where $R^1$ is as indicated in the table below).

Formula 10

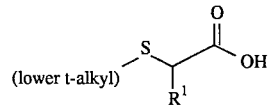

| $R^1$ | Name |
|---|---|
| hydrogen | 2-(t-butylthio)ethanoic acid |
| 2-propyl | (2S)-2-(t-butylthio)-3-methylbutanoic acid |
| 2-methylpropyl | (2S)-2-(t-butylthio)-4-methylpentanoic acid |
| 2-butyl | (2S)-2-(t-butylthio)-3-methylpentanoic acid |
| blocked aminobutyl | (2S)-6-amino-2-(t-butylthio)hexanoic acid |
| carbamoylmethyl | (2S)-3-carbamoyl-2-(t-butylthio)propanoic acid |

7D. Formula 10 Varying $R^1$

By following the procedures described in Example 7B and substituting (2S)-2-bromopropanoic acid with other compounds of Formula 9 there are obtained the correspondingly substituted compounds of Formula 10 (where $R^1$ is as indicated in the table below).

Formula 10

(lower t-alkyl)—S—CH(R¹)—C(=O)—OH

| R¹ | Name |
|---|---|
| 2-propyl | (2R)-2-(t-butylthio)-3-methylbutanoic acid |
| 2-methylpropyl | (2R)-2-(t-butylthio)-4-methylpentanoic acid |
| 2-butyl | (2R)-2-(t-butylthio)-3-methylpentanoic acid |
| blocked aminobutyl | (2R)-6-amino-2-(t-butylthio)hexanoic acid |
| carbamoylmethyl | (2R)-3-carbamoyl-2-(t-butylthio)propanoic acid |

EXAMPLE 8

Preparation of (2S)-2-(t-Butylthio)-1-Propanol

8A. Formula 11 Where R¹ Is Methyl

To a stirred solution of 1.47 g of the (2S)-2-(t-butylthio)propanoic acid in 22 mL of THF at 0° C. was added dropwise 22 mL of 1M borane/THF over a period of 15 min. Stirring was continued at room temperature for 3 h. The reaction was quenched by dropwise addition of cold water. The mixture was extracted with ether. The organic layer was washed with saturated NaHCO₃, saturated NaCl solution and dried over Na₂SO₄. The solvent was evaporated under vacuum and the residue was purified by flash chromatography (10% EtOAc in hexane) to give 1.10 g of (2S)-2-(tert-butylthio)-1-propanol as an oil at 82% yield. Characteristic analytical data are as follows: $^1$H NMR (300 MHz, CDCl₃) δ3.61 (ddd, J=5, 9, 11 Hz, 1H), 3.33 (ddd, J=4, 8, 11 Hz, 1H), 2.89 (m, 1H), 2.31 (dd, J=4, 9 Hz, 1H, OH), 1.36 (s, 9H), 1.30 (d, J=7 Hz, 3H); $[\alpha]_D^{25}$ −10.3° (c=2.04, MeOH).

8B. Preparation of the Corresponding (2R) Isomer of Formula 11

By following the procedure described in Example 8A and substituting (2S)-2-(t-butylthio)propanoic acid with (2R)-2-(t-butylthio)propanoic acid, (2R)-2-(t-butylthio)-1-propanol was obtained at 89% yield. Characteristic analytical data are as follows: $[\alpha]_D^{25}$ +9.8° (c=2.02, MeOH).

8C. Formula 11 Varying R¹

By following the procedures described in Example 8A and substituting (2S)-2-(t-butylthio)propanoic acid with other compounds of Formula 10 there are obtained the correspondingly substituted of compounds of Formula 11 (where R¹ is as indicated in the table below).

Formula 11

(lower t-alkyl)—S—CH(R¹)—CH₂—OH

| R¹ | Name |
|---|---|
| hydrogen | 2-(t-butylthio)ethanol |
| 2-propyl | (2S)-2-(t-butylthio)-3-methylbutanol |
| 2-methylpropyl | (2S)-2-(t-butylthio)-4-methylpentanol |
| 2-butyl | (2S)-2-(t-butylthio)-3-methylpentanol |
| blocked aminoethyl | (2S)-4-amino-2-(t-butylthio)butanol |
| blocked aminobutyl | (2S)-6-amino-2-(t-butylthio)hexanol |
| carbamoylmethyl | (2S)-3-carbamoyl-2-(t-butylthio)propanol |

8D. Formula 11 Varying R¹

By following the procedures described in Example 8B and substituting (2R)-2-(t-butylthio)propanoic acid with other compounds of Formula 10 there are obtained the correspondingly substituted of compounds of Formula 11 (where R¹ is as indicated in the table below).

Formula 11

(lower t-alkyl)—S—CH(R¹)—CH₂—OH

| R¹ | Name |
|---|---|
| 2-propyl | (2R)-2-(t-butylthio)-3-methylbutanol |
| 2-methylpropyl | (2R)-2-(t-butylthio)-4-methylpentanol |
| 2-butyl | (2R)-2-(t-butylthio)-3-methylpentanol |
| blocked aminoethyl | (2R)-4-amino-2-(t-butylthio)butanol |
| blocked aminobutyl | (2R)-6-amino-2-(t-butylthio)hexanol |
| carbamoylmethyl | (2R)-3-carbamoyl-2-(t-butylthio)propanol |

EXAMPLE 9

Preparation of (2S)-1-(Acetylthio)-2-(t-Butylthio)Propane

9A. Formula 12 Where R¹ Is Methyl

To a stirred solution of 3.54 g of triphenylphosphine in 50 mL of THF at 0° C. was added 2.66 mL of diisopropyl azodicarboxylate. The mixture was stirred for an additional 30 min. To the resulting white precipitate was added 1.00 g of (2S)-2-(t-butylthio)-1-propanol in 5 mL of THF. The reaction mixture was stirred for 10 min, then 0.966 mL of thiolacetic acid was added and stirring was continued at 0° C. for 1 h and at room temperature for 1 h. The solvent was evaporated under vacuum and the residue was purified by flash chromatography (5% CH₂Cl₂ in hexane) to give 1.16 g of (2S)-1-(acetylthio)-2 -(t-butylthio)propane as an oil at 83% yield. Characteristic analytical data are as follows: $^1$H NMR (300 MHz, CDCl₃) δ3.32 (m, 1H), 2.8–2.94 (m, 2H), 2.35 (s, 3H), 1.38 (s, 9H), 1.33 (d, J=7 Hz, 3H).

9B. Preparation of the Corresponding (2R) Isomer of Formula 12

By following the procedure described in Example 9A and substituting (2S)-2-(t-butylthio)-1-propanol with (2R)-2-(t-butylthio)-1-propanol, (2R)-1 -(acetylthio)-2-(t-butylthio)propane was obtained as an oil at 70% yield.

9C. Formula 12 Varying R¹

By following the procedures described in Example 9A and substituting (2S)-2-(t-butylthio)-1-propanol with other compounds of Formula 11 there are obtained the correspondingly substituted of compounds of Formula 12 (where R¹ is as indicated in the table below).

Formula 12

(lower t-alkyl)-S-CH(R¹)-CH₂-S-C(=O)-CH₃

| R¹ | Name |
|---|---|
| hydrogen | 1-(acetylthio)-2-(t-butylthio)ethane |
| 2-propyl | (2S)-1-(acetylthio)-2-(t-butylthio)-3-methylbutane |
| 2-methylpropyl | (2S)-1-(acetylthio)-2-(t-butylthio)-4-methylpentane |
| 2-butyl | (2S)-1-(acetylthio)-2-(t-butylthio)-3-methylpentane |
| blocked aminoethyl | (2S)-1-(acetylthio)-4-amino-2-(t-butylthio)butane |
| blocked aminobutyl | (2S)-1-(acetylthio)-6-amino-2-(t-butylthio)hexane |
| carbamoylmethyl | (2S)-1-(acetylthio)-3-carbamoyl-2-(t-butylthio)propane |

9D. Formula 12 Varying R¹

By following the procedures described in Example 9B and substituting (2R)-2-(t-butylthio)-1-propanol with other compounds of Formula 11 there are obtained the correspondingly substituted of compounds of Formula 12 (where R¹ is as indicated in the table below).

Formula 12

(lower t-alkyl)-S-CH(R¹)-CH₂-S-C(=O)-CH₃

| R¹ | Name |
|---|---|
| 2-propyl | (2R)-1-(acetylthio)-2-(t-butylthio)-3-methylbutane |
| 2-methylpropyl | (2R)-1-(acetylthio)-2-(t-butylthio)-4-methylpentane |
| 2-butyl | (2R)-1-(acetylthio)-2-(t-butylthio)-3-methylpentane |
| blocked aminoethyl | (2R)-1-(acetylthio)-4-amino-2-(t-butylthio)butane |
| blocked aminobutyl | (2R)-1-(acetylthio)-6-amino-2-(t-butylthio)hexane |
| carbamoylmethyl | (2R)-1-(acetylthio)-3-carbamoyl-2-(t-butylthio)propane |

EXAMPLE 10

Preparation of t-BuS(S)CHMeCH₂—(S-D-Leu)-OH

10A. Formula 14 Where R¹ Is Methyl and R³ Is 2-Methylpropyl

To a solution of 46 mg of Na in 2 mL of EtOH was added a solution of mg of (2S)-1-(acetylthio)-2-(t-butylthio)propane in 1 mL of EtOH with stirring at room temperature under nitrogen. After 5 min a solution of 170 mg of (2S)-2-bromo-4-methylpentanoic acid in 1 mL of EtOH was added and stirring was continued at room temperature for 4 h. The reaction mixture was poured into water, acidified with acetic acid and extracted with CH₂Cl₂. The organic layer was dried over Na₂SO₄ and evaporated under vacuum. Purification of the residue by flash chromatography (15% EtOAc in hexane) afforded 146 mg of t-BuS(S)CHMeCH₂—(S-D-Leu)-OH as a colorless gum at 60% yield. Characteristic analytical data are as follows: ¹H NMR (300 MHz, CDCl₃) δ3.72 (t, J=7 Hz, 1H), 3.01 (dd, J=5, 12 Hz, 1H), 2.88–2.98 (m, 1H), 2.76 (dd, J=8, 12 Hz, 1H), 1.73–1.85 (m, 2H), 1.55 (m, 1H), 1.39 (d, J=7 Hz, 3H), 1.35 (s 9H), 0.95 (d, J=7 Hz, 3H), 0.93 (d, J=7 Hz, 3H); [α]$_D^{25}$ +2.3° (c=0.86, MeOH).

10B. Preparation of the Corresponding (2R) Isomer of Formula 14

By following the procedure described in Example 10A and substituting (2S) -1- (acetylthio) -2- (t-butylthio)propane with (2R) -1-(acetylthio)-2-(t-butylthio)propane, t-BuS(R)CHMeCH₂—(S-D-Leu)-OH was obtained as a colorless gum at 51% yield. Characteristic analytical data are as follows: ¹H NMR (300 MHz, CDCl₃) δ3.36 (t, J=7 Hz, 1H), 3.08 (dd, J=5, 13 Hz, 1H), 2.87–2.96 (m, 1H), 2.66 (dd, J=9, 13 Hz, 1H), 1.72–1.85 (m, 2H), 1.55 (m, 1H), 1.39 (d, J=7 Hz, 3H), 1.35 (s, 9H), 0.95 (d, J=6 Hz, 3H), 0.93 (d, J=6 Hz, 3H); [α]$_D^{25}$ +121° (c=0.88, MeOH).

10C. Formula 14 Varying R¹

By following the procedures described in Example 10A and substituting (2S)-1-(acetylthio)-2-(t-butylthio)propane with other compounds of Formula 12 there are obtained the correspondingly substituted of compounds of Formula 14 (where R¹ is as indicated in the table below).

Formula 14

(lower t-alkyl)-S-CH(R¹)-CH₂-S-CH(R³)-C(=O)-OH where R³ is 2-methylpropyl

| R¹ | Name |
|---|---|
| hydrogen | t-BuSCH₂CH₂—(S-D-Leu)—OH |
| 2-propyl | t-BuS(S)CH(2-propyl)CH₂—(S-D-Leu)—OH |
| 2-methylpropyl | t-BuS(S)CH(2-methylpropyl)CH₂—(S-D-Leu)—OH |
| 2-butyl | t-BuS(S)CH(2-butyl)CH₂—(S-D-Leu)—OH |
| blocked aminoethyl | t-BuS(S)CH(aminoethyl)CH₂—(S-D-Leu)—OH |
| blocked aminobutyl | t-BuS(S)CH(aminobutyl)CH₂—(S-D-Leu)—OH |
| carbamoylmethyl | t-BuS(S)CH(carbamoylmethyl)CH₂—(S-D-Leu)—OH |

10D. Formula 14 Varying R¹

By following the procedures described in Example 10B and substituting (2R)-1-(acetylthio)-2-(t-butylthio)propane with other compounds of Formula 12 there are obtained the correspondingly substituted of compounds of Formula 14 (where R¹ is as indicated in the table below).

Formula 14

(lower t-alkyl)-S-CH(R¹)-CH₂-S-CH(R³)-C(=O)-OH where R³ is 2-methylpropyl

| R¹ | Name |
|---|---|
| 2-propyl | t-BuS(R)CH(2-propyl)CH₂—(S-D-Leu)—OH |
| 2-methylpropyl | t-BuS(R)CH(2-methylpropyl)CH₂—(S-D-Leu)—OH |
| 2-butyl | t-BuS(R)CH(2-butyl)CH₂—(S-D-Leu)—OH |
| aminoethyl | t-BuS(R)CH(aminoethyl)CH₂—(S-D-Leu)—OH |
| aminobutyl | t-BuS(R)CH(aminobutyl)CH₂—(S-D-Leu) |

-continued

Formula 14

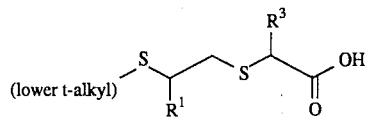

where R³ is 2-methylpropyl

| R¹ | Name |
|---|---|
| carbamoylmethyl | t-BuS(R)CH(carbamoylmethyl)CH₂—(S-D-Leu)—OH |

10E. Formula 14 Varying $R^1$ and $R^3$

By following the procedures described in Example 10A and substituting (2S)-2-bromo-4-methylpentanoic acid with other compounds of Formula 2 and (2S)-1-(acetylthio)-2-(t-butylthio)propane with other compounds of Formula 12 (e.g., compounds with $R^1$ that are prepared according to Examples 9A and 9B) there are obtained the correspondingly substituted compounds of Formula 14 (where $R^1$ and $R^3$ are as indicated in the table below).

Formula 14

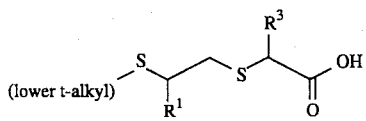

| R¹ | R³ |
|---|---|
| hydrogen | hydrogen |
| 2-propyl | methyl |
| 2-methylpropyl | 2-propyl |
| 2-butyl | 2-butyl |
| blocked aminoethyl | 2-methylpropyl |
| blocked aminobutyl | blocked 4-hydroxyphenylmethyl |
| carbamoylmethyl | blocked 3-indolylmethyl |
| hydrogen | 4-methoxyphenylmethyl |
| 2-propyl | phenylethyl |
| 2-methylpropyl | phenylethyl |
| 2-butyl | 4-methoxyphenylmethyl |
| blocked aminoethyl | blocked 3-indolylmethyl |
| blocked aminobutyl | blocked 4-hydroxyphenylmethyl |
| carbamoylmethyl | 2-methylpropyl |
| hydrogen | 2-butyl |
| 2-propyl | 2-propyl |
| 2-methylpropyl | methyl |
| 2-butyl | hydrogen |
| blocked aminoethyl | hydrogen |
| blocked aminobutyl | methyl |
| carbamoylmethyl | 2-propyl |
| hydrogen | 2-butyl |
| 2-propyl | 2-methylpropyl |
| 2-methylpropyl | blocked 4-hydroxyphenylmethyl |
| 2-butyl | blocked 3-indolylmethyl |
| blocked aminoethyl | 4-methoxyphenylmethyl |
| blocked aminobutyl | phenylethyl |
| carbamoylmethyl | phenylethyl |

EXAMPLE 11

Preparation of t-Bus(S)CHMeCH₂—(S-D-Leu)-Phe-NHMe

11A. Formula 15 Where $R^1$ Is Methyl, $R^3$ Is 2-Methylpropyl, $R^4$ Is Phenylmethyl, $R^5$ Is Methyl To a solution of 98 mg of the t-BuS(S) CHMeCH₂-(S-D-Leu)-OH and 63 mg of Phe-NHMe in 2 mL of 1,2-dimethoxyethane were added 57 mg of 1-hydroxybenzotriazole and 87 mg of dicyclohexylcarbodiimide with stirring at 0°–5° C. The reaction mixture was allowed to warm to room temperature and stirring was continued overnight. The solvent was evaporated and the residue was triturated several times with 10% CH₂Cl₂ in hexane. The filtrate was dried over Na₂SO₄ and evaporated under vacuum. Purification of the residue by flash chromatography (25% EtOAc in hexane) afforded 150 mg of t-BuS(S)CHMeCH₂—(S-D-Leu)-Phe-NHMe as a solid at 97% yield. Characteristic analytical data are as follows: mp 130°–131° C.; ¹H NMR (300 MHz, CDCl₃) δ7.20–7.34 (m, 5H), 7.12 (d, J=8 Hz, 1H), 6.02 (br s, 1H), 4.62 (q, J=8 Hz, 1H), 3.31 (t, J=7 Hz, 1H), 3.13 (dd, J=7, 14 Hz, 1H), 3.07 (dd, J=8, 14 Hz, 1H), 2.82 (m, 1H), 2.72 (d, J=5 Hz, 3H), 2.61 (dd, J=6, 13 Hz, 1H), 2.41 (dd, J=8, 13 Hz, 1H), 1.63–1.75 (m, 2H), 1.50 (m, 1H), 1.33 (s, 9H), 1.32 (d, J=5 Hz, 3H), 0.86 (d, J=6 Hz, 3H), 0.88 (d, J=6 Hz, 3H).

11B. Preparation of the Corresponding (2R) Isomer of Formula 15

By following the procedure described in Example 11A and substituting t-BuS(S)CHMeCH₂—(S-D-Leu)-OH with t-BuS(R)CHMeCH₂—(S-D-Leu)-OH, 27 mg t-BuS(R)CHMeCH₂—(S-D-Leu)-Phe-NHMe was obtained as a solid. Characteristic analytical data are as follows: mp 135°–136° C.; ¹H NMR (300 MHz, CDCl₃) δ7.20– 7.34 (m, 5H), 7.15 (d, J=8 Hz, 1H), 6.05 (br s, 1H), 4.61 (q, J=8 Hz, 1H), 3.30 (dd, J=7, 8 Hz, 1H), 3.14 (dd, J=7, 14 Hz, 1H), 3.07 (dd, J=8, 14 Hz, 1H), 2.75–2.83 (m, 1H), 2.73 (d, J=5 Hz, 3H), 2.58 (dd, J=5, 13 Hz, 1H), 2.34 (dd, J=9, 13 Hz, 1H), 1.63–1.75 (m, 2H), 1.46 (m, 1H), 1.31 (d, J=7 Hz, 3H), 1.30 (s, 9H), 0.89 (d, J=6 Hz, 3H), 0.88 (d, J=6 Hz, 3H).

11C. Formula 15 Varying $R^1$

By following the procedures described in Example 11A and substituting t-BuS(S)CHMeCH₂—(S-D-Leu)-OH with other compounds of Formula 14 there are obtained the correspondingly substituted of compounds of Formula 15 (where $R^1$, $R^3$, $R^4$, $R^5$, and $R^6$ are as indicated in the table below).

Formula 15

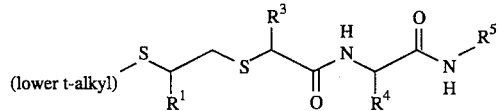

where R³ is 2-Methylpropyl, R⁴ is phenylmethyl, R⁵ is methyl

| R¹ | Name |
|---|---|
| hydrogen | t-BuSCH₂CH₂—(S-D-Leu)—Phe—NHMe |
| 2-propyl | t-BuS(S)CH(2-propyl)CH₂—(S-D-Leu)—Phe—NHMe |
| 2-methylpropyl | t-BuS(S)CH(2-methylpropyl)CH₂—(S-D-Leu)—Phe—NHMe |
| 2-butyl | t-BuS(S)CH(2-butyl)CH₂—(S-D-Leu)—Phe—NHMe |
| blocked aminoethyl | t-BuS(S)CH(aminoethyl)CH₂—(S-D-Leu)—Phe—NHMe |
| blocked aminobutyl | t-BuS(S)CH(aminobutyl)CH₂—(S-D-Leu)—Phe—NHMe |
| carbamoylmethyl | t-BuS(S)CH(carbamoylmethyl)CH₂—(S-D-Leu)—Phe—NHMe |

11D. Formula 15 Varying $R^1$

By following the procedures described in Example 11B and substituting t-BuS(R)CHMeCH₂—(S-D-Leu)-OH with other compounds of Formula 14 there are obtained the correspondingly substituted compounds of Formula 15

(where $R^1$, $R^3$, $R^4$ $R^5$, $R^6$ and $R^7$ are as indicated in the table below).

Formula 15

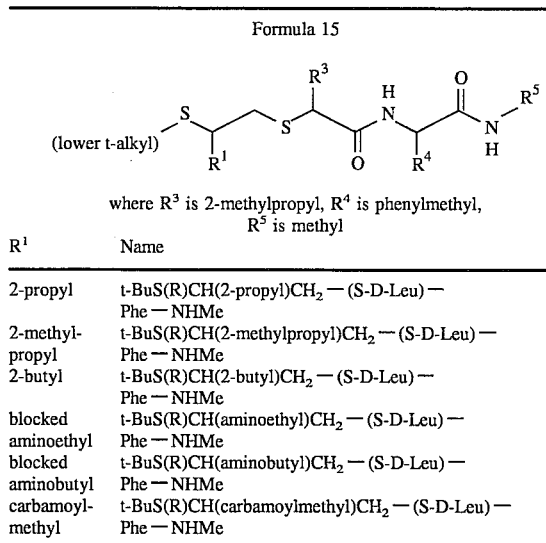

where $R^3$ is 2-methylpropyl, $R^4$ is phenylmethyl, $R^5$ is methyl

| $R^1$ | Name |
|---|---|
| 2-propyl | t-BuS(R)CH(2-propyl)CH$_2$ — (S-D-Leu) — Phe — NHMe |
| 2-methyl-propyl | t-BuS(R)CH(2-methylpropyl)CH$_2$ — (S-D-Leu) — Phe — NHMe |
| 2-butyl | t-BuS(R)CH(2-butyl)CH$_2$ — (S-D-Leu) — Phe — NHMe |
| blocked aminoethyl | t-BuS(R)CH(aminoethyl)CH$_2$ — (S-D-Leu) — Phe — NHMe |
| blocked aminobutyl | t-BuS(R)CH(aminobutyl)CH$_2$ — (S-D-Leu) — Phe — NHMe |
| carbamoyl-methyl | t-BuS(R)CH(carbamoylmethyl)CH$_2$ — (S-D-Leu) — Phe — NHMe |

11E. Formula 15 Varying $R^1$, $R^3$, $R^4$, $R^5$, and $R^6$

By following the procedures described in Example 11A and substituting Phe-NHMe with other compounds of Formula 6 and t-BuS(S)CHMeCH$_2$—(S-D-Leu)-OH with other compounds of Formula 14 (e.g., compounds with $R^1$ and $R^3$ that are prepared according to Example 10A) there are obtained the correspondingly substituted compounds of Formula 15 (where $R^1$, $R^3$, $R^4$, $R^5$ and $R^6$ are as indicated in the tables below).

Formula 15

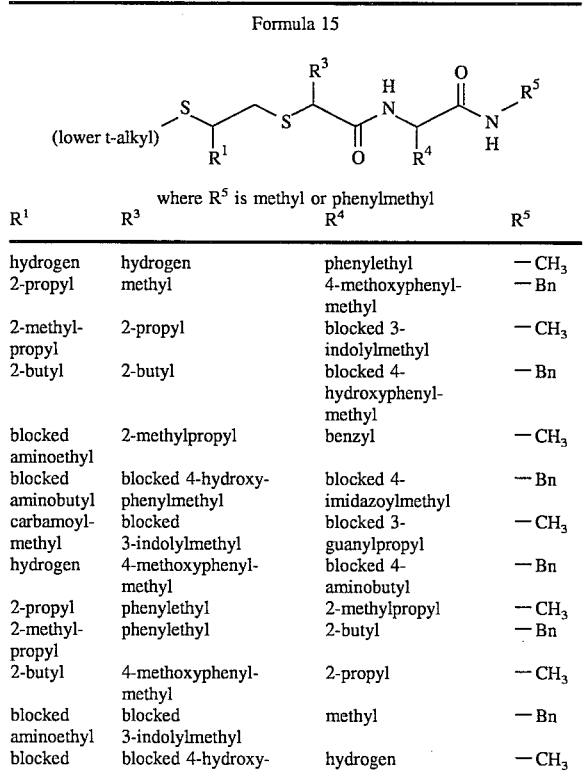

where $R^5$ is methyl or phenylmethyl

| $R^1$ | $R^3$ | $R^4$ | $R^5$ |
|---|---|---|---|
| hydrogen | hydrogen | phenylethyl | —CH$_3$ |
| 2-propyl | methyl | 4-methoxyphenyl-methyl | —Bn |
| 2-methyl-propyl | 2-propyl | blocked 3-indolylmethyl | —CH$_3$ |
| 2-butyl | 2-butyl | blocked 4-hydroxyphenyl-methyl | —Bn |
| blocked aminoethyl | 2-methylpropyl | benzyl | —CH$_3$ |
| blocked aminobutyl | blocked 4-hydroxy-phenylmethyl | blocked 4-imidazoylmethyl | —Bn |
| carbamoyl-methyl | blocked 3-indolylmethyl | blocked 3-guanylpropyl | —CH$_3$ |
| hydrogen | 4-methoxyphenyl-methyl | blocked 4-aminobutyl | —Bn |
| 2-propyl | phenylethyl | 2-methylpropyl | —CH$_3$ |
| 2-methyl-propyl | phenylethyl | 2-butyl | —Bn |
| 2-butyl | 4-methoxyphenyl-methyl | 2-propyl | —CH$_3$ |
| blocked aminoethyl | blocked 3-indolylmethyl | methyl | —Bn |
| blocked | blocked 4-hydroxy- | hydrogen | —CH$_3$ |

Formula 15

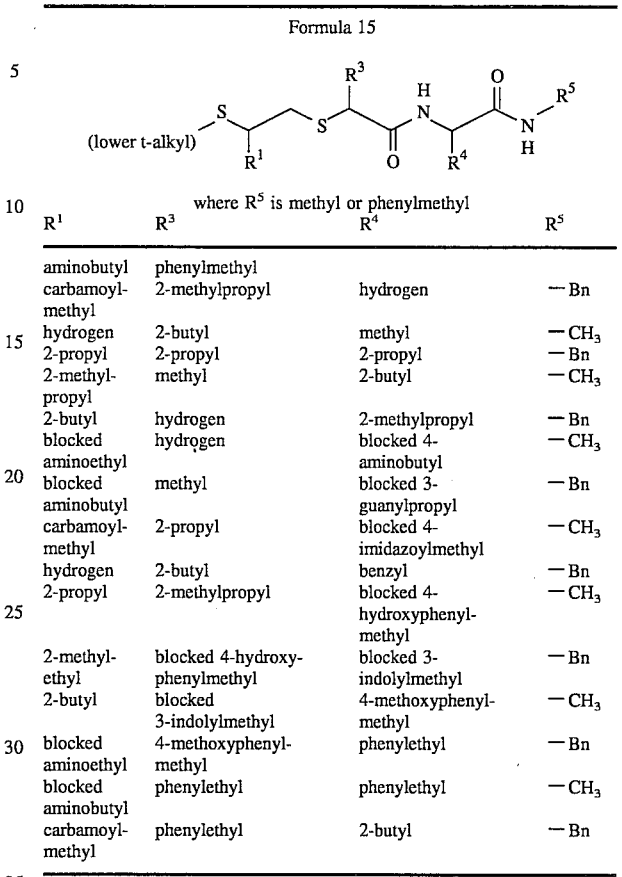

where $R^5$ is methyl or phenylmethyl

| $R^1$ | $R^3$ | $R^4$ | $R^5$ |
|---|---|---|---|
| aminobutyl | phenylmethyl | | |
| carbamoyl-methyl | 2-methylpropyl | hydrogen | —Bn |
| hydrogen | 2-butyl | methyl | —CH$_3$ |
| 2-propyl | 2-propyl | 2-propyl | —Bn |
| 2-methyl-propyl | methyl | 2-butyl | —CH$_3$ |
| 2-butyl | hydrogen | 2-methylpropyl | —Bn |
| blocked aminoethyl | hydrogen | blocked 4-aminobutyl | —CH$_3$ |
| blocked aminobutyl | methyl | blocked 3-guanylpropyl | —Bn |
| carbamoyl-methyl | 2-propyl | blocked 4-imidazoylmethyl | —CH$_3$ |
| hydrogen | 2-butyl | benzyl | —Bn |
| 2-propyl | 2-methylpropyl | blocked 4-hydroxyphenyl-methyl | —CH$_3$ |
| 2-methyl-ethyl | blocked 4-hydroxy-phenylmethyl | blocked 3-indolylmethyl | —Bn |
| 2-butyl | blocked 3-indolylmethyl | 4-methoxyphenyl-methyl | —CH$_3$ |
| blocked aminoethyl | 4-methoxyphenyl-methyl | phenylethyl | —Bn |
| blocked aminobutyl | phenylethyl | phenylethyl | —CH$_3$ |
| carbamoyl-methyl | phenylethyl | 2-butyl | —Bn |

Formula 15

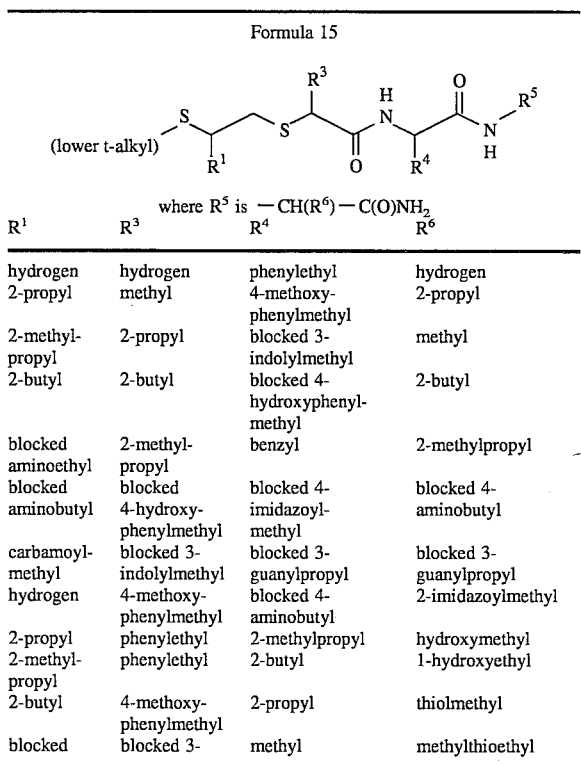

where $R^5$ is —CH($R^6$)—C(O)NH$_2$

| $R^1$ | $R^3$ | $R^4$ | $R^6$ |
|---|---|---|---|
| hydrogen | hydrogen | phenylethyl | hydrogen |
| 2-propyl | methyl | 4-methoxy-phenylmethyl | 2-propyl |
| 2-methyl-propyl | 2-propyl | blocked 3-indolylmethyl | methyl |
| 2-butyl | 2-butyl | blocked 4-hydroxyphenyl-methyl | 2-butyl |
| blocked aminoethyl | 2-methyl-propyl | benzyl | 2-methylpropyl |
| blocked aminobutyl | blocked 4-hydroxy-phenylmethyl | blocked 4-imidazoyl-methyl | blocked 4-aminobutyl |
| carbamoyl-methyl | blocked 3-indolylmethyl | blocked 3-guanylpropyl | blocked 3-guanylpropyl |
| hydrogen | 4-methoxy-phenylmethyl | blocked 4-aminobutyl | 2-imidazoylmethyl |
| 2-propyl | phenylethyl | 2-methylpropyl | hydroxymethyl |
| 2-methyl-propyl | phenylethyl | 2-butyl | 1-hydroxyethyl |
| 2-butyl | 4-methoxy-phenylmethyl | 2-propyl | thiolmethyl |
| blocked | blocked 3- | methyl | methylthioethyl |

Formula 15

where $R^5$ is $-CH(R^6)-C(O)NH_2$

| $R^1$ | $R^3$ | $R^4$ | $R^6$ |
|---|---|---|---|
| aminoethyl | indolylmethyl | | |
| blocked aminobutyl | blocked 4-hydroxyphenylmethyl | hydrogen | methylthioethyl |
| carbamoylmethyl | 2-methylpropyl | hydrogen | thiolmethyl |
| hydrogen | 2-butyl | methyl | 1-hydroxyethyl |
| 2-propyl | 2-propyl | 2-propyl | hydroxymethyl |
| 2-methylpropyl | methyl | 2-butyl | 2-imidazoylmethyl |
| 2-butyl | hydrogen | 2-methylpropyl | blocked 3-guanylpropyl |
| blocked aminoethyl | hydrogen | blocked 4-aminobutyl | blocked 4-aminobutyl |
| blocked aminobutyl | methyl | blocked 3-guanylpropyl | 2-methylpropyl |
| carbamoylmethyl | 2-propyl | blocked 4-imidazoylmethyl | 2-butyl |
| hydrogen | 2-butyl | benzyl | methyl |
| 2-propyl | 2-methylpropyl | blocked 4-hydroxyphenylmethyl | 2-propyl |
| 2-methylpropyl | blocked 4-hydroxyphenylmethyl | blocked 3-indolylmethyl | hydrogen |
| 2-butyl | blocked 3-indolylmethyl | 4-methoxyphenylmethyl | methylthioethyl |
| blocked aminoethyl | 4-methoxyphenylmethyl | phenylethyl | thiolmethyl |
| blocked aminobutyl | phenylethyl | phenylethyl | 1-hydroxyethyl |
| carbamoylmethyl | phenylethyl | 2-butyl | hydrogen |

EXAMPLE 12

Preparation of 2-NO$_2$C$_6$H$_4$SS(S)CHMeCH$_2$—(S-D-Leu)-Phe-NHMe

12A. Formula 16 Where $R^1$ Is Methyl, $R^3$ Is 2-Methylpropyl, $R^4$ Is Phenylmethyl, $R^5$ Methyl To a solution of 150 mg of t-BuS(S) CHMeCH$_2$- (S-D-Leu)-Phe-NHMe in 1 mL of glacial acetic acid was added 71 mg of 2-NO$_2$C$_6$H$_4$SCl. The mixture was stirred at room temperature for 2 h. The acetic acid was evaporated under vacuum and the residue was purified by flash chromatography (35% EtOAc in hexane) to give 177 mg of 2-NO$_2$C$_6$H$_4$SS(S)CHMeCH$_2$—(S-D-Leu)-Phe-NHMe at 97% yield. Characteristic analytical data are as follows: mp 138°–140° C.; $^1$H NMR (300 MHz, CDCl$_3$) δ8.26 (dt, J=2, 8 Hz, 2H), 7.67 (dt, J=1, 8 Hz, 1H), 7.17– 7.38 (m, 6H), 6.94 (br d, J=8 Hz, 1H, NH), 5.80 (br s, 1H, NH), 4.55 (q, J=8 Hz, 1H), 3.24 (t, J=7 Hz, 1H), 3.04 (d, J=8 Hz, 2H), 2.93 (m, 1H), 2.73 (d, J=5 Hz, 3H, NMe), 2.63 (dd, J=7, 14 Hz, 1H), 2.41 (dd, J=8, 14 Hz, 1H), 1.59– 1.71 (m, 2H), 1.39–1.50 (m, 1H), 1.30 (d, J=7 Hz, 3H), 0.86 (d, J=7 Hz, 3H 0.85 (d, J=7 Hz, 3H).

12B. Preparation of the Corresponding (2R) Isomer of Formula 16

By following the procedure described in Example 12A and substituting the (S)-isomer with t-BuS(R)CHMeCH$_2$—(S-D-Leu)-Phe-NHMe, 2-NO$_2$C$_6$H$_4$SS(R)CHMeCH$_2$—(S-D-Leu)-Phe-NHMe was obtained at 95% yield. Characteristic analytical data are as follows: mp 170°–172° C.; $^1$H NMR (300 MHz, CDCl$_3$) δ8.27 (dd, J=1, 3 Hz, 1H), 8.24 (dd, J=1, 3 Hz, 1H), 7.67 (dt, J=1, 7 Hz, 1H), 7.20–7.38 (m, 6H), 6.92 (d, J=7 Hz, 1H), 5.98 (m, 1H), 4.55 (q, J=8 Hz, 1H), 3.15 (t, J=7 Hz, 1H), 3.00–3.12 (m, 2H), 2.80–2.90 (m, 1H), 2.74 (d, J=5 Hz, 3H), 2.55 (dd, J=5, 13 Hz, 1H), 2.27 (dd, J=9, 13 Hz, 1H), 1.52–1.64 (m, 2H), 1.40 (m, 1H), 1.30 (d, J=7 Hz, 3H), 0.84 (d, J=6 Hz, 3H), 0.81 (d, J=6 Hz, 3H).

12C. Formula 16 Varying $R^1$

By following the procedures described in Example 12A and substituting t-BuS(S)CHMeCH$_2$—(S-D-Leu)-Phe-NHMe with other compounds of Formula 15 there are obtained the correspondingly substituted of compounds of Formula 16 (where the $R^1$, $R^3$, $R^4$, $R^5$ and $R^6$ substituents are as indicated in the table below).

Formula 16

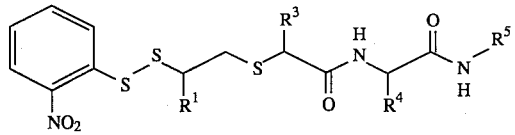

where $R^3$ is 2-methylpropyl, $R^4$ is phenylmethyl, $R^5$ is methyl

| $R^1$ | Name |
|---|---|
| hydrogen | 2-NO$_2$C$_6$H$_4$SSCH$_2$CH$_2$ — (S — D — Leu) — Phe — NHMe |
| 2-propyl | 2-NO$_2$C$_6$H$_4$SS(S)CH(2-propyl)CH$_2$ — (S — D — Leu) — Phe — NHMe |
| 2-methylpropyl | 2-NO$_2$C$_6$H$_4$SS(S)CH(2-methylpropyl)CH$_2$ — (S — D — Leu) — Phe — NHMe |
| 2-butyl | 2-NO$_2$C$_6$H$_4$SS(S)CH(2-butyl)CH$_2$ — (S — D — Leu) — Phe — NHMe |
| blocked aminoethyl | 2-NO$_2$C$_6$H$_4$SS(S)CH(aminoethyl)CH$_2$(S — D — Leu) — Phe — NHMe |
| blocked aminobutyl | 2-NO$_2$C$_6$H$_4$SS(S)CH(aminobutyl)CH$_2$ — (S — D — Leu) — Phe — NHMe |
| carbamoylmethyl | 2-NO$_2$C$_6$H$_4$SS(S)CH(carbamoylmethyl)CH$_2$ — (S — D — Leu) — Phe — NHMe |
| 2-PhtN-ethyl | 2-NO$_2$C$_6$H$_4$SS(S)CH(2-PhtN-ethyl)CH$_2$ — (S — (S — D — Leu) — Phe — NHMe |
| 4-PhtN-butyl | 2-NO$_2$C$_6$H$_4$SS(S)CH(4-PhtN-butyl)CH$_2$ — (S — (S — D — Leu) — Phe — NHMe |

12D. Formula 16 Varying $R^1$

By following the procedures described in Example 12B and substituting t-BuS(R)CHMeCH$_2$—(S-D-Leu)-Phe-NHMe with other compounds of Formula 15 there are obtained the correspondingly substituted of compounds of Formula 16 (where the $R^1$, $R^3$, $R^4$, $R^5$, and $R^6$ substituents are as indicated in the table below).

pounds that are prepared according to Examples 11A–11E) there are obtained the correspondingly substituted compounds Formula 16 (where the $R^1$, $R^3$, $R^4$, $R^5$, and $R^6$ substituents are as indicated in the tables below).

Formula 16

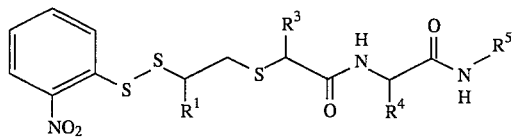

where $R^3$ is 2-methylpropyl, $R^4$ is phenylmethyl, $R^5$ is methyl

| $R^1$ | Name |
|---|---|
| 2-propyl | 2-NO$_2$C$_6$H$_4$SS(R)CH(2-propyl)CH$_2$—(S—D—Leu)—Phe—NHMe |
| 2-methylpropyl | 2-NO$_2$C$_6$H$_4$SS(R)CH(2-methylpropyl)CH$_2$—(S—D—Leu)—Phe—NHMe |
| 2-butyl | 2-NO$_2$C$_6$H$_4$SS(R)CH(2-butyl)CH$_2$—(S—D—Leu)—Phe—NHMe |
| blocked aminoethyl | 2-NO$_2$C$_6$H$_4$SS(R)CH(aminoethyl)CH$_2$—(S—D—Leu)—Phe—NHMe |
| blocked aminobutyl | 2-NO$_2$C$_6$H$_4$SS(R)CH(aminobutyl)CH$_2$—(S—D—Leu)—Phe—NHMe |
| carbamoylmethyl | 2-NO$_2$C$_6$H$_4$SS(R)CH(carbamoylmethyl)CH$_2$—(S—D—Leu)—Phe—NHMe |
| 2-PhtN-ethyl | 2-NO$_2$C$_6$H$_4$SS(R)CH(2-PhtN-ethyl)CH$_2$—(S—D—Leu)—Phe—NHMe |
| 2-PhtN-butyl | 2-NO$_2$C$_6$H$_4$SS(R)CH(4-PhtN-butyl)CH$_2$—(S—D—Leu)—Phe—NHMe |

12E. Formula 16 Varying $R^1$, $R^3$, $R^4$, $R^5$ and $R^6$

By following the procedures described in Example 12A and substituting t-BuS(S)CHMeCH$_2$—(S-D-Leu)-Phe-NHMe with other compounds of Formula 15 (e.g., com- Formula 16

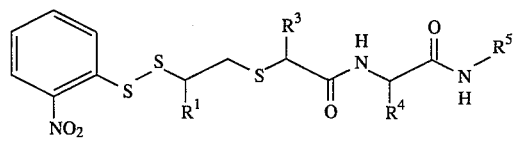

where $R^5$ is methyl or phenylmethyl

| $R^1$ | $R^3$ | $R^4$ | $R^5$ |
|---|---|---|---|
| hydrogen | hydrogen | phenylethyl | —CH$_3$ |
| 2-propyl | methyl | 4-methoxyphenylmethyl | —Bn |
| 2-methylpropyl | 2-propyl | blocked 3-indolylmethyl | —CH$_3$ |
| 2-butyl | 2-butyl | blocked 4-hydroxyphenylmethyl | —Bn |
| blocked aminoethyl | 2-methylpropyl | benzyl | —CH$_3$ |
| blocked aminobutyl | blocked 4-hydroxyphenylmethyl | blocked 4-imidazoylmethyl | —Bn |
| carbamoylmethyl | blocked 3-indolylmethyl | blocked 3-guanylpropyl | —CH$_3$ |
| hydrogen | 4-methoxyphenylmethyl | blocked 4-aminobutyl | —Bn |
| 2-propyl | phenylethyl | 2-methylpropyl | —CH$_3$ |
| 2-methylpropyl | phenylethyl | 2-butyl | —Bn |
| 2-butyl | 4-methoxyphenylmethyl | 2-propyl | —CH$_3$ |
| blocked aminoethyl | blocked 3-indolylmethyl | methyl | —Bn |
| blocked aminobutyl | blocked 4-hydroxyphenylmethyl | hydrogen | —CH$_3$ |
| carbamoylmethyl | 2-methylpropyl | hydrogen | —Bn |
| hydrogen | 2-butyl | methyl | —CH$_3$ |
| 2-propyl | 2-propyl | 2-propyl | —Bn |
| 2-methylpropyl | methyl | 2-butyl | —CH$_3$ |
| 2-butyl | hydrogen | 2-methylpropyl | —Bn |
| blocked aminoethyl | hydrogen | blocked 4-aminobutyl | —CH$_3$ |
| blocked aminobutyl | methyl | blocked 3-guanylpropyl | —Bn |

-continued

Formula 16

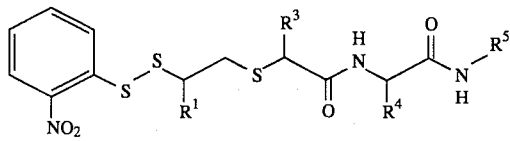

where R⁵ is methyl or phenylmethyl

| R¹ | R³ | R⁴ | R⁵ |
|---|---|---|---|
| carbamoylmethyl | 2-propyl | blocked 4-imidazoylmethyl | —CH₃ |
| hydrogen | 2-butyl | benzyl | —Bn |
| 2-propyl | 2-methylpropyl | blocked 4-hydroxyphenylmethyl | —CH₃ |
| 2-methylpropyl | blocked 4-hydroxyphenylmethyl | blocked 3-indolylmethyl | —Bn |
| 2-butyl | blocked 3-indolylmethyl | 4-methoxyphenylmethyl | —CH₃ |
| blocked aminoethyl | 4-methoxyphenylmethyl | phenylethyl | —Bn |
| blocked aminobutyl | phenylethyl | phenylethyl | —CH₃ |
| carbamoylmethyl | phenylethyl | 2-butyl | —Bn |

Formula 16

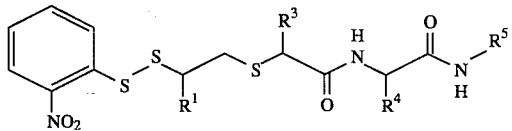

where R⁵ is —CH(R⁶)—C(O)NH₂

| R¹ | R³ | R⁴ | R⁶ |
|---|---|---|---|
| hydrogen | hydrogen | phenylethyl | hydrogen |
| 2-propyl | methyl | 4-methoxyphenylmethyl | 2-propyl |
| 2-methylpropyl | 2-propyl | blocked 3-indolylmethyl | methyl |
| 2-butyl | 2-butyl | blocked 4-hydroxyphenylmethyl | 2-butyl |
| blocked aminoethyl | 2-methylpropyl | benzyl | 2-methylpropyl |
| blocked aminobutyl | blocked 4-hydroxyphenylmethyl | blocked 4-imidazoylmethyl | blocked 4-aminobutyl |
| carbamoylmethyl | blocked 3-indolylmethyl | blocked 3-guanylpropyl | blocked 3-guanylpropyl |
| hydrogen | 4-methoxyphenylmethyl | blocked 4-aminobutyl | 2-imidazoylmethyl |
| 2-propyl | phenylethyl | 2-methylpropyl | hydroxymethyl |
| 2-methylpropyl | phenylethyl | 2-butyl | 1-hydroxyethyl |
| 2-butyl | 4-methoxyphenylmethyl | 2-propyl | thiolmethyl |
| blocked aminoethyl | blocked 3-indolylmethyl | methyl | methylthioethyl |
| blocked aminobutyl | blocked 4-hydroxyphenylmethyl | hydrogen | methylthioethyl |
| carbamoylmethyl | 2-methylpropyl | hydrogen | thiolmethyl |
| hydrogen | 2-butyl | methyl | 1-hydroxyethyl |
| 2-propyl | 2-propyl | 2-propyl | hydroxymethyl |
| 2-methylpropyl | methyl | 2-butyl | 2-imidazoylmethyl |
| 2-butyl | hydrogen | 2-methylpropyl | blocked 3-guanylpropyl |
| blocked aminoethyl | hydrogen | blocked 4-aminobutyl | blocked 4-aminobutyl |
| blocked aminobutyl | methyl | blocked 3-guanylpropyl | 2-methylpropyl |

Formula 16

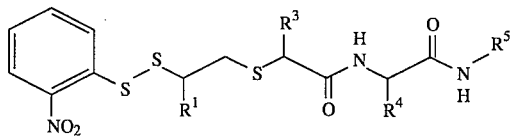

where $R^5$ is $-CH(R^6)-C(O)NH_2$

| $R^1$ | $R^3$ | $R^4$ | $R^6$ |
|---|---|---|---|
| carbamoylmethyl | 2-propyl | blocked 4-imidazoyl-methyl | 2-butyl |
| hydrogen | 2-butyl | benzyl | methyl |
| 2-propyl | 2-methylpropyl | blocked 4-hydroxyphenyl-methyl | 2-propyl |
| 2-methylpropyl | blocked 4-hydroxy-phenylmethyl | blocked 3-indolylmethyl | hydrogen |
| 2-butyl | blocked 3-indolyl-methyl | 4-methoxy-phenylmethyl | methylthioethyl |
| blocked aminoethyl | 4-methoxyphenyl-methyl | phenylethyl | thiolmethyl |
| blocked aminobutyl | phenylethyl | phenylethyl | 1-hydroxyethyl |
| carbamoylmethyl | phenylethyl | 2-butyl | hydrogen |

EXAMPLE 13

Preparation of HS(S)CHMeCH$_2$—(S-D-Leu)-Phe-NHMe

13A. Formula I Where $R^1$ Is Methyl, $R^3$ Is 2-Methylpropyl $R^4$ Is Phenylmethyl, $R^5$ Is Methyl To a solution of 167 mg of 2-NO$_2$C$_6$H$_4$SS(S)CHMeCH$_2$—(S-D-Leu)-Phe-NHMe in 2 mL of MeOH and 0.5 mL of dioxane were added 0.5 mL of 2-mercaptoethanol and 0.78 mL of 0.4M NaOH solution. The mixture was stirred at room temperature under nitrogen for 30 min. The reaction mixture was then poured into water, acidified with acetic acid and extracted with CH$_2$Cl$_2$. The organic layer was dried over Na$_2$SO$_4$ and evaporated under vacuum. Purification of the residue by flash chromatography (25% EtOAc in hexane) afforded 89 mg of HS(S-)CHMeCH$_2$—(S-D-Leu)-Phe-NHMe as a solid at 74% yield. Characteristic analytical data are as follows: mp 157°–158° C.; $^1$H NMR (300 MHz, CDCl$_3$) δ7.20–7.35 (m, 5H), 6.98 (br d, J=8 Hz, 1H, NH), 5.85 (br s, 1H, NH), 4.60 (q, J=8 Hz, 1H), 3.27 (dd, J=7, 8 Hz, 1H), 3.15 (dd, J=7, 14 Hz, 1H), 3.07 (dd, J=8, 14 Hz, 1H), 2.91– 3.03 (m, 1H), 2.75 (d, J=5 Hz, 3H, NMe), 2.41 (dd, J=6, 13 Hz, 1H), 2.35 (dd, J=8, 13 Hz, 1H), 1.88 (d, J=6 Hz, 1H, SH), 1.62–1.72 (m, 2H), 1.50 (m, 1H), 1.28 (d, J=7 Hz, 3H), 0.90 (d, J=6 Hz, 3H), 0.89 (d, J=6 Hz, 3H); $^{13}$C NMR (75 MHz, CDCl$_3$) δ172.92, 171.54, 136.96, 129.35, 128.96, 127.27, 54.52, 48.36 (CH), 42.0 (CH$_2$), 41.24 (CH$_2$), 37.78 (CH), 34.85, 26.01 (CH), 25.87 (CH), 23.64 (CH$_3$), 22.32 (CH$_3$), 21.73 (CH$_3$); [α]$_D^{25}$ +47° (c=0.40, MeOH). Anal. Calcd for C$_{19}$H$_{30}$N$_2$O$_2$S$_2$: C, 59.65; H, 7.90; N, 7.32; S, 16.76. Found: C, 59.72; H, 7.96; N, 7.37; S, 16.83.

13B. Preparation of the Corresponding (2R) Isomer of Formula I

By following the procedure described in Example 13A and substituting the (S)-isomer with 2-NO$_2$C$_6$H$_4$SS(R)CHMeCH$_2$—(S-D-Leu)-Phe-NHMe gave HS(R)CHMeCH$_2$— (S-D-Leu)-Phe-NHMe as a solid at 70% yield. Characteristic analytical data are as follows: mp 155°–157° C.; $^1$H NMR (300 MHz, CDCl$_3$) δ7.20–7.34 (m, 5H), 7.07 (d, J=8 Hz, 1H), 6.04 (br s, 1H), 4.64 (q, J=8 Hz, 1H), 3.30 (dd, J=7, 8 Hz, 1H), 3.15 (dd, J=7, 14 Hz, 1H), 3.07 (dd, J=8, 14 Hz, 1H), 2.96 (m, 1H), 2.75 (d, J=5 Hz, 3H), 2.42 (d, J=7 Hz, 2H), 1.78 (d, J=6 Hz, 1H, SH), 1.60–1.72 (m, 2H), 1.46 (m, 1H), 1.31 (d, J=7 Hz, 3H), 0.89 (d, J=6 Hz, 3H), 0.88 (d, J=6 Hz, 3H).

13C. Formula I Varying $R^1$

By following the procedures described in Example 13A and substituting 2-NO$_2$C$_6$H$_4$SS(S)CHMeCH$_2$—(S-D-Leu)-Phe-NHMe with other compounds of Formula 16 there are obtained the correspondingly substituted of compounds of Formula I (where the $R^1$, $R^3$, $R^4$, $R^5$, and $R^6$ substituents are as indicated in the table below).

Formula I

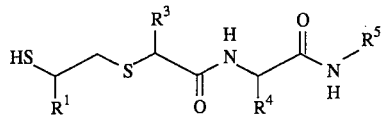

where $R^3$ is 2-methylpropyl, $R^4$ is phenylmethyl, $R^5$ is methyl

| $R^1$ | Name |
|---|---|
| hydrogen | HSCH$_2$CH$_2$—(S—D—Leu)—Phe—NHMe |
| 2-propyl | HS(S)CH(2-propyl)CH$_2$—(S—D—Leu)—Phe—NHMe |
| 2-methylpropyl | HS(S)CH(2-methylpropyl)CH$_2$—(S—D—Leu)—Phe—NHMe |
| 2-butyl | HS(S)CH(2-butyl)CH$_2$—(S—D—Leu)—Phe—NHMe |
| 2-aminoethyl | HS(S)CH(2-aminoethyl)CH$_2$—(S—D—Leu)—Phe—NHMe |
| 2-aminobutyl | HS(S)CH(4-aminobutyl)CH$_2$—(S—D—Leu)—Phe—NHMe |
| carbamoylmethyl | HS(S)CH(carbamoylmethyl)CH$_2$—(S—D—Leu)—Phe—NHMe |
| 2-PhtN-ethyl | HS(S)CH(2-PhtN-ethyl)CH$_2$—(S—D—Leu)—Phe—NHMe |
| 2-PhtN-butyl | HS(S)CH(4-PhtN-butyl)CH$_2$—(S—D—Leu)—Phe—NHMe |

13D. Formula I Varying $R^1$

By following the procedures described in Example 13B and substituting 2-NO$_2$C$_6$H$_4$SS(R)CHMeCH$_2$—(S-D-Leu)-Phe-NHMe with other compounds of Formula 16 there are obtained the correspondingly substituted compounds of Formula I (where the $R^1$, $R^3$, $R^4$, $R^5$ and $R^6$ substituents are as indicated in the table below).

Formula I

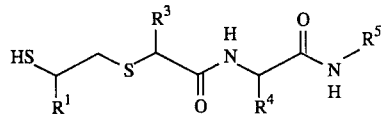

where $R^3$ is 2-methylpropyl, $R^4$ is phenylmethyl, $R^5$ is methyl

| $R^1$ | Name |
|---|---|
| 2-propyl | HS(R)CH(2-propyl)CH$_2$—(S—(S—D—Leu)—Phe—NHMe |
| 2-methylpropyl | HS(R)CH(2-methylpropyl)CH$_2$—(S—D—Leu)—Phe—NHMe |
| 2-butyl | HS(R)CH(2-butyl)CH$_2$—(S—D—Leu)—Phe—NHMe |
| aminoethyl | HS(R)CH(aminoethyl)CH$_2$—(S—D—Leu)—Phe—NHMe |
| aminobutyl | HS(R)CH(aminobutyl)CH$_2$—(S—D—Leu)—Phe—NHMe |
| carbamoylmethyl | HS(R)CH(carbamoylmethyl)CH$_2$—(S—D—Leu)—Phe—NHMe |
| carbamoylpentyl | HS(R)CH(carbamoylpentyl)CH$_2$—(S—D—Leu)—Phe—NHMe |
| 2-PhtN-ethyl | HS(R)CH(2-PhtN-ethyl)CH$_2$—(S—D—Leu)—Phe—NHMe |
| 4-PhtN-butyl | HS(R)CH(4-PhtN-butyl)CH$_2$—(S—D—Leu)—Phe—NHMe |

13E. Formula I Varying $R^1$, $R^3$, $R^4$, $R^5$ and $R^6$

By following the procedures described in Example 13A and substituting 2-NO$_2$C$_6$H$_4$SS(S)CHMeCH$_2$—(S-D-Leu)-Phe-NHMe with other compounds of Formula 16 (e.g., compounds that are prepared according to Examples 12A–12E) there are obtained the correspondingly substituted compounds of Formula I (where the $R^1$, $R^3$, $R^4$, $R^5$ and $R^6$ substituents are as indicated in the tables below).

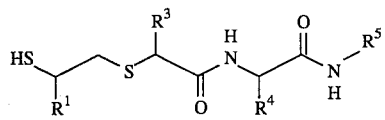

where $R^5$ is methyl or phenylmethyl

| $R^1$ | $R^3$ | $R^4$ | $R^5$ |
|---|---|---|---|
| hydrogen | hydrogen | phenylethyl | —CH$_3$ |
| 2-propyl | methyl | 4-methoxyphenyl-methyl | —Bn |
| 2-methylpropyl | 2-propyl | 3-indolylmethyl | —CH$_3$ |
| 2-butyl | 2-butyl | 4-hydroxyphenyl-methyl | —Bn |
| aminoethyl | 2-methylpropyl | benzyl | —CH$_3$ |
| aminobutyl | 4-hydroxyphenyl-methyl | 4-imidazoylmethyl | —Bn |
| carbamoylmethyl | 3-indolylmethyl | 3-guanylpropyl | —CH$_3$ |

| | | | |
|---|---|---|---|
| hydrogen | 4-methoxyphenyl-methyl | 4-aminobutyl | —Bn |
| 2-propyl | phenylethyl | 2-methylpropyl | —CH₃ |
| 2-methylpropyl | phenylethyl | 2-butyl | —Bn |
| 2-butyl | 4-methoxyphenyl- | 2-propyl | —CH₃ |
| 2-butyl | 3-indolylmethyl | 4-methoxyphenyl-methyl | —CH₃ |
| aminoethyl | 4-methoxyphenyl-methyl | phenylethyl | —Bn |
| aminobutyl | phenylethyl | phenylethyl | —CH₃ |
| carbamoylmethyl | phenylethyl | 2-butyl | —Bn |

Formula I

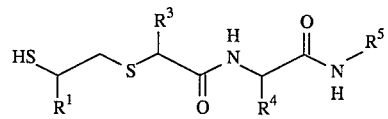

where R⁵ is —CH(R⁶)—C(O)NH₂

| R¹ | R³ | R⁴ | R⁶ |
|---|---|---|---|
| hydrogen | hydrogen | phenylethyl | hydrogen |
| 2-propyl | methyl | 4-methoxy-phenylmethyl | 2-propyl |
| 2-methylpropyl | 2-propyl | 3-indolyl-methyl | methyl |
| 2-butyl | 2-butyl | 4-hydroxy-phenylmethyl | 2-butyl |
| aminoethyl | 2-methylpropyl | benzyl | 2-methylpropyl |
| aminobutyl | 4-hydroxy-phenylmethyl | 4-imidazoyl-methyl | 4-aminobutyl |
| carbamoylmethyl | 3-indolylmethyl | 3-guanylpropyl | 3-guanylpropyl |
| hydrogen | 4-methoxyphenyl-methyl | 4-aminobutyl | 2-imidazoylmethyl |
| 2-propyl | phenylethyl | 2-methylpropyl | hydroxymethyl |
| 2-methylpropyl | phenylethyl | 2-butyl | 1-hydroxyethyl |
| 2-butyl | 4-methoxyphenyl-methyl | 2-propyl | thiolmethyl |
| aminoethyl | 3-indolylmethyl | methyl | methylthioethyl |
| aminobutyl | 4-hydroxy-phenylmethyl | hydrogen | methylthioethyl |
| carbamoylmethyl | 2-methylpropyl | hydrogen | thiolmethyl |
| hydrogen | 2-butyl | methyl | 1-hydroxyethyl |
| 2-propyl | 2-propyl | 2-propyl | hydroxymethyl |
| 2-methylpropyl | methyl | 2-butyl | 2-imidazoylmethyl |
| 2-butyl | hydrogen | 2-methylpropyl | 3-guanylpropyl |
| aminoethyl | hydrogen | blocked 4-aminobutyl | 4-aminobutyl |
| aminobutyl | methyl | 3-guanylpropyl | 2-methylpropyl |
| carbamoylmethyl | 2-propyl | 4-imidazoyl-methyl | 2-butyl |
| hydrogen | 2-butyl | benzyl | methyl |
| 2-propyl | 2-methylpropyl | 4-hydroxy-phenylmethyl | 2-propyl |
| 2-methylpropyl | 4-hydroxy-phenylmethyl | 3-indolyl-methyl | hydrogen |
| 2-butyl | 3-indolylmethyl | 4-methoxy-phenylmethyl | methylthioethyl |
| aminoethyl | 4-methoxyphenyl-methyl | phenylethyl | thiolmethyl |
| aminobutyl | phenylethyl | phenylethyl | 1-hydroxyethyl |
| carbamoylmethyl | phenylethyl | 2-butyl | hydrogen |

| | | | |
|---|---|---|---|
| aminoethyl | methyl 3-indolylmethyl | methyl | —Bn |
| aminobutyl | 4-hydroxyphenyl-methyl | hydrogen | —CH₃ |
| carbamoylmethyl | 2-methylpropyl | hydrogen | —Bn |
| hydrogen | 2-butyl | methyl | —CH₃ |
| 2-propyl | 2-propyl | 2-propyl | —Bn |
| 2-methylpropyl | methyl | 2-butyl | —CH₃ |
| 2-butyl | hydrogen | 2-methylpropyl | —Bn |
| aminoethyl | hydrogen | 4-aminobutyl | —CH₃ |
| aminobutyl | methyl | 3-guanylpropyl | —Bn |
| carbamoylmethyl | 2-propyl | 4-imidazoylmethyl | —CH₃ |
| hydrogen | 2-butyl | benzyl | —Bn |
| 2-propyl | 2-methylpropyl | 4-hydroxyphenyl-methyl | —CH₃ |
| 2-methylpropyl | 4-hydroxyphenyl- | 3-indolylmethyl | —Bn |

EXAMPLE 14

Preparation of t-BuS(R)CHMeCH₂SCH₂NPht

14A. Formula 18 Where R² Is Methyl

To a solution of 83 mg of Na in 3 mL of EtOH was added 671 mg of t-BuS(R)CHMeCH₂SAc in 2 mL of EtOH. The mixture was stirred at room temperature for 15 min under nitrogen, poured into water, acidified with acetic acid and extracted with CH₂Cl₂. The organic layer was dried over Na₂SO₄ and evaporated under vacuum to give 480 mg of t-BuS(R)CHMeCH₂SH (i.e., Formula 17 where R² is methyl) at 90% yield. To a solution of the crude mercaptan in 8 mL of CH₂Cl₂ was added 0.78 mL of diisopropylethylamine and 843 mg of N-(bromomethyl)phthalimide with stirring at room temperature under nitrogen. Stirring was continued at room temperature for 18 h. The mixture was diluted with 75 mL of $CH_2Cl_2$ and extracted with 1M HCl. The organic layer was dried over $Na_2SO_4$ and evaporated under vacuum. The residue was purified by flash chromatography (10% EtOAc in hexane) to give 846 mg of t-BuS(R)CHMeCH$_2$SCH$_2$NPht as a solid at 81% yield. Characteristic analytical data are as follows: mp 63°–64° C.; $^1$H NMR (300 MHz, CDCl$_3$) δ7.88 (d, J=5 Hz, 1H), 7.87 (d, J=5 Hz, 1H), 7.75 (d, J=6 Hz, 1H), 7.74 (d, J=6 Hz, 1H), 4.81 (dd, J=14, 17 Hz, 2H), 3.11 (dd, J=5, 12 Hz, 1H), 2.93 (m, 1H), 2.84 (dd, J=8, 12 Hz, 1H), 1.37 (d, J=7 Hz, 3H), 1.32 (s, 9H).

14B. Preparation of the Corresponding (S) Isomer of Formula 18

By following the procedure described in Example 14A and substituting the (R)-isomer with t-BuS(S)CHMeCH$_2$SAc there is obtained t-BuS(S)CHMeCH$_2$SCH$_2$NPht.

14C. Formula 18 Varying $R^2$

By following the procedures described in Example 14A and substituting t-BuS(R)CHMeCH$_2$SAc with other compounds of Formula 12A there are obtained the correspondingly substituted of compounds of Formula 18 (where $R^2$ is as indicated in the table below).

Formula 18

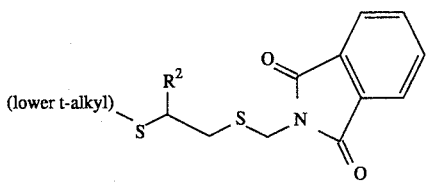

| $R^2$ | Name |
|---|---|
| hydrogen | t-BuSCH$_2$CH$_2$SCH$_2$NPht |
| 2-propyl | t-BuS(R)CH(2-propyl)CH$_2$SCH$_2$NPht |
| 2-methylpropyl | t-BuS(R)CH(2-methylpropyl)CH$_2$SCH$_2$NPht |
| 2-butyl | t-BuS(R)CH(2-butyl)CH$_2$SCH$_2$NPht |
| blocked aminoethyl | t-BuS(R)CH(aminoethyl)CH$_2$SCH$_2$NPht |
| blocked aminobutyl | t-BuS(R)CH(aminobutyl)CH$_2$SCH$_2$NPht |
| carbamoylmethyl | t-BuS(R)CH(carbamoylmethyl)CH$_2$SCH$_2$NPht |

14D. Formula 18 Varying $R^2$

By following the procedures described in Example 14B and substituting t-BuS(S)CHMeCH$_2$SAc with other compounds of Formula 12A there are obtained the correspondingly substituted compounds of Formula 18 (where $R^2$ is as indicated in the table below).

Formula 18

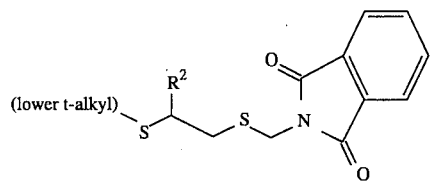

| $R^2$ | Name |
|---|---|
| 2-propyl | t-BuS(S)CH(2-propyl)CH$_2$SCH$_2$NPht |
| 2-methylpropyl | t-BuS(S)CH(2-methylpropyl)CH$_2$SCH$_2$NPht |
| 2-butyl | t-BuS(S)CH(2-butyl)CH$_2$SCH$_2$NPht |
| blocked aminoethyl | t-BuS(S)CH(aminoethyl)CH$_2$SCH$_2$NPht |
| blocked aminobutyl | t-BuS(S)CH(aminobutyl)CH$_2$SCH$_2$NPht |
| carbamoylmethyl | t-BuS(S)CH(carbamoylmethyl)CH$_2$SCH$_2$NPht |

EXAMPLE 15

Preparation of 2-NO$_2$C$_6$H$_4$SS(R)CHMeCH$_2$SCH$_2$NPht

15A. Formula 19 Where $R^2$ Is Methyl

To a solution of 423 mg of t-BuS(R)CHMeCH$_2$SCH$_2$NPht in 3.5 mL of acetic acid was added 250 mg of 2-nitrobenzenesulfenyl chloride. The mixture was stirred at room temperature for 2 h. The acetic acid was evaporated under vacuum and the residue was purified by flash chromatography (10% EtOAc in hexane) to give 500 mg of 2-NO$_2$C$_6$H$_4$SS(R)CHMeCH$_2$SCH$_2$NPht as a gum at 92% yield. Characteristic analytical data are as follows: $^1$H NMR (300 MHz, CDCl$_3$) δ8.34 (d, J=8 Hz, 1H), 8.24 (d, J=8 Hz, 1H), 7.88 (d, J=5 Hz, 1H), 7.87 (d, J=5 Hz, 1H), 7.75 (d, J=6 Hz, 1H), 7.74 (d, J=6 Hz, 1H), 7.66 (t, J=7 Hz, 1H), 7.31 (t, J=7 Hz, 1H), 4.68 (dd, J=14, 19 Hz, 2H), 3.12 (m, 2H), 2.78 (dd, J=7, 13 Hz, 1H), 1.41 (d, J=7 Hz, 3H).

15B. Preparation of the Corresponding (S) Isomer Of Formula 19

By following the procedure described in Example 15A and substituting the (R)-isomer with t-BuS(S)CHMeCH$_2$SCH$_2$NPht there is obtained 2-NO$_2$C$_6$H$_4$SS(S)CHMeCH$_2$SCH$_2$NPht.

15C. Formula 19 Varying $R^2$

By following the procedures described in Example 15A and substituting t-BuS(R)CHMeCH$_2$SCH$_2$NPht with other compounds of Formula 18 there are obtained the correspondingly substituted compounds of Formula 19 (where $R^2$ is as indicated in the table below).

Formula 19

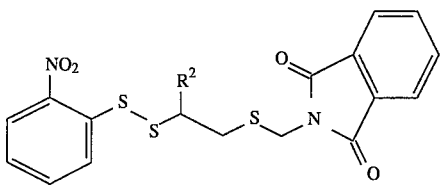

| R² | Name |
| --- | --- |
| hydrogen | 2-NO₂C₆H₄SSCH₂CH₂SCH₂NPht |
| 2-propyl | 2-NO₂C₆H₄SS(R)CH(2-propyl)CH₂SCH₂NPht |
| 2-methylpropyl | 2-NO₂C₆H₄SS(R)CH(2-methylpropyl)CH₂SCH₂NPht |
| 2-butyl | 2-NO₂C₆H₄SS(R)CH(2-butyl)CH₂SCH₂NPht |
| blocked aminoethyl | 2-NO₂C₆H₄SS(R)CH(aminoethyl)CH₂SCH₂NPht |
| blocked aminobutyl | 2-NO₂C₆H₄SS(R)CH(aminobutyl)CH₂SCH₂NPht |
| carbamoylmethyl | 2-NO₂C₆H₄SS(R)CH(carbamoylmethyl)CH₂SCH₂NPht |

15D. Formula 19 Varying R²

By following the procedures described in Example 15B and substituting t-BuS(S)CHMeCH₂SCH₂NPht with other compounds of Formula 18 there are obtained the correspondingly substituted compounds of Formula 19 (where R² is as indicated in the table below).

Formula 19

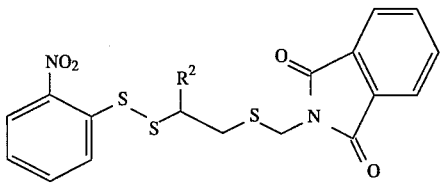

| R² | Name |
| --- | --- |
| 2-propyl | 2-NO₂C₆H₄SS(S)CH(2-propyl)CH₂SCH₂NPht |
| 2-methylpropyl | 2-NO₂C₆H₄SS(S)CH(2-methylpropyl)CH₂SCH₂NPht |
| 2-butyl | 2-NO₂C₆H₄SS(S)CH(2-butyl)CH₂SCH₂NPht |
| blocked aminoethyl | 2-NO₂C₆H₄SS(S)CH(aminoethyl)CH₂SCH₂NPht |
| blocked aminobutyl | 2-NO₂C₆H₄SS(S)CH(aminobutyl)CH₂SCH₂NPht |
| carbamoylmethyl | 2-NO₂C₆H₄SS(S)CH(carbamoylmethyl)CH₂SCH₂NPht |

EXAMPLE 16

Preparation of PhtNCH₂SCH₂(R)CHMeSH

16A. Formula 20 Where R² Is Methyl

To a solution of 500 mg of 2-NO₂C₆H₄SS(R)CHMeCH₂SCH₂NPht in 3 mL of MeOH and 1.5 mL of dioxane was added 1.65 mL of 2-mercaptoethanol and 2.94 mL of 0.4M NaOH. The mixture was stirred at room temperature under nitrogen for 30 min. The reaction mixture was poured into water, acidified with acetic acid and extracted with CH₂Cl₂. The organic layer was dried over Na₂SO₄ and evaporated under vacuum. The residue was purified by flash chromatography (35% CH₂Cl₂ in hexane) to give 147 mg of HS(R)CHMeCH₂SCH₂NPht as a gum at 46% yield. Characteristic analytical data are as follows: ¹H NMR (300 MHz, CDCl₃) δ7.88 (d, J=5 Hz, 1H), 7.87 (d, J=5 Hz, 1H), 7.75 (d, J=6 Hz, 1H), 7.74 (d, J=6 Hz, 1H), 4.80 (s, 2H), 3.20 (2dd, J=5, 9 Hz, 1H), 2.94 (d, J=7 Hz, 2H), 1.93 (d, J=6 Hz, 1H, SH), 1.39 (d, J=7 Hz, 3H).

16B. Preparation of the Corresponding (S) Isomer of Formula 20

By following the procedure described in Example 16A and substituting the (R)-isomer with 2-NO₂C₆H₄SS(S)CHMeCH₂SCH₂NPht there is obtained HS(S)CHMeCH₂SCH₂NPht.

16C. Formula 20 Varying R²

By following the procedures described in Example 16A and substituting 2-NO₂C₆H₄SS(R)CHMeCH₂SCH₂NPht with other compounds of Formula 19 there are obtained the correspondingly substituted compounds of Formula 20 (where R² is as indicated in the table below).

Formula 20

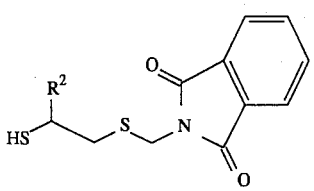

| $R^2$ | Name |
|---|---|
| hydrogen | HSCH$_2$CH$_2$SCH$_2$NPht |
| 2-propyl | HS(R)CH(2-propyl)CH$_2$SCH$_2$NPht |
| 2-methylpropyl | HS(R)CH(2-methylpropyl)CH$_2$SCH$_2$NPht |
| 2-butyl | HS(R)CH(2-butyl)CH$_2$SCH$_2$NPht |
| blocked aminoethyl | HS(R)CH(aminoethyl)CH$_2$SCH$_2$NPht |
| blocked aminobutyl | HS(R)CH(aminobutyl)CH$_2$SCH$_2$NPht |
| carbamoylmethyl | HS(R)CH(carbamoylmethyl)CH$_2$SCH$_2$NPht |

16D. Formula 20 Varying $R^2$

By following the procedures described in Example 16B and substituting 2-NO$_2$C$_6$H$_4$SS(S)CHMeCH$_2$SCH$_2$NPht with other compounds of Formula 19 there are obtained the correspondingly substituted compounds of Formula 20 (where $R^2$ is as indicated in the table below).

Formula 20

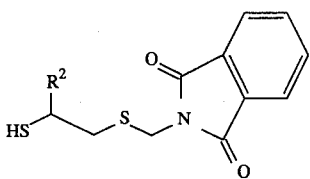

| $R^2$ | Name |
|---|---|
| 2-propyl | HS(S)CH(2-propyl)CH$_2$SCH$_2$NPht |
| 2-methylpropyl | HS(S)CH(2-methylpropyl)CH$_2$SCH$_2$NPht |
| 2-butyl | HS(S)CH(2-butyl)CH$_2$SCH$_2$NPht |
| blocked aminoethyl | HS(S)CH(aminoethyl)CH$_2$SCH$_2$NPht |
| blocked aminobutyl | HS(S)CH(aminobutyl)CH$_2$SCH$_2$NPht |
| carbamoylmethyl | HS(S)CH(carbamoylmethyl)CH$_2$SCH$_2$NPht |

EXAMPLE 17

Preparation of PhtNCH$_2$SCH$_2$(R)CHMe—(S-D-Leu)-O t-Butyl Ester

17A. Formula 22 Where $R^2$ Is Methyl and $R^5$ Is 2-Methylpropyl

To a solution of 147 mg of PhtNCH$_2$SCH$_2$(R)CHMeSH and 152 mg of (2S)-2-bromo-4-methylpentanoic acid tert-butyl ester in 0.4 mL of acetonitrile was added 0.2 mL of N,N-diisopropylethylamine. The mixture was stirred at room temperature under nitrogen for 2 days. The solvent was removed under vacuum, the residue dissolved in CH$_2$Cl$_2$ and washed extracted with 1M HCl. The organic layer was dried over Na$_2$SO$_4$, evaporated under vacuum, and the residue was purified by flash chromatography (5% EtOAc in hexane) to give 172 mg of PhtNCH$_2$SCH$_2$(R)CHMe-(S-D-Leu)-O t-Bu at 72% yield. Characteristic analytical data are as follows: $^1$H NMR (300 MHz, CDCl$_3$) δ7.88 (d, J=5 Hz, 1H), 7.87 (d, J=5 Hz, 1H), 7.75 (d, J=6 Hz, 1H), 7.74 (d, J=6 Hz, 1H), 4.81 (s, 2H), 3.43 (dd, J=6, 9 Hz, 1H), 3.17 (m, 2H), 2.82 (m, 1H), 1.71 (m, 2H), 1.46 (s, 9H), 1.40 (m, 1H), 1.37 (d, J=7 Hz, 3H), 0.94 (d, J=7 Hz, 3H), 0.92 (d, J=7 Hz, 3H).

17B. Preparation of the Corresponding (S) Isomer of Formula 22

By following the procedure described in Example 17A and substituting the (R)-isomer with PhtNCH$_2$SCH$_2$(S)CHMeSH there is obtained PhtNCH$_2$SCH$_2$(S)CHMe-(S-D-Leu)-O t-Bu.

17C. Formula 22 Varying $R^2$

By following the procedures described in Example 17A and substituting PhtNCH$_2$SCH$_2$(R)CHMeSH with other compounds of Formula 20 there are obtained the correspondingly substituted compounds of Formula 22 (where $R^2$ is as indicated in the table below).

Formula 22

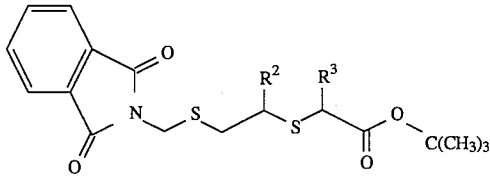

where $R^3$ is 2-methylpropyl

| $R^2$ | Name |
|---|---|
| hydrogen | PhtNCH$_2$SCH$_2$CH$_2$—(S—D—Leu)—O(t-Bu) |
| 2-propyl | PhtNCH$_2$SCH$_2$(R)CH(2-propyl)-(S—D—Leu)—O(t-Bu) |
| 2-methylpropyl | PhtNCH$_2$SCH$_2$(R)CH(2-methylpropyl)-(S—D—Leu)—O(t-Bu) |
| 2-butyl | PhtNCH$_2$SCH$_2$(R)CH(2-butyl)-(S—D—Leu)—O(t-Bu) |

-continued

Formula 22

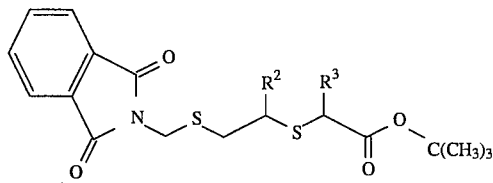

where R³ is 2-methylpropyl

| R² | Name |
|---|---|
| blocked aminoethyl | PhtNCH₂SCH₂(R)CH(aminoethyl)-(S—D—Leu)—O(t-Bu) |
| blocked aminobutyl | PhtNCH₂SCH₂(R)CH(aminobutyl)-(S—D—Leu)—O(t-Bu) |
| carbamoylmethyl | PhtNCH₂SCH₂(R)CH(carbamoylmethyl)-(S—D—Leu)—O(t-Bu) |

17D. Formula 22 Varying R²

By following the procedures described in Example 17B and substituting PhtNCH₂SCH₂(S)CHMeSH with other compounds of Formula 20 there are obtained the correspondingly substituted compounds of Formula 22 (where R² and R³ are as indicated in the table below).

Formula 22

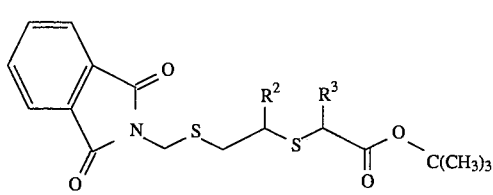

where R³ is 2-methylpropyl

| R² | Name |
|---|---|
| 2-propyl | PhtNCH₂SCH₂(S)CH(2-propyl)-(S—D—Leu)—O(t-Bu) |
| 2-methylpropyl | PhtNCH₂SCH₂(S)CH(2-methylpropyl)-(S—D—Leu)—O(t-Bu) |
| 2-butyl | PhtNCH₂SCH₂(S)CH(2-butyl)-(S—D—Leu)—O(t-Bu) |
| blocked aminoethyl | PhtNCH₂SCH₂(S)CH(aminoethyl)-(S—D—Leu)—O(t-Bu) |
| blocked aminobutyl | PhtNCH₂SCH₂(S)CH(aminobutyl)-(S—D—Leu)—O(t-Bu) |
| carbamoylmethyl | PhtNCH₂SCH₂(S)CH(carbamoylmethyl)-(S—D—Leu)—O(t-Bu) |

17E. Formula 22 Varying R² and R³

By following the procedures described in Example 17A and substituting (2S)-2-bromo-4-methylpentanoic acid tert-butyl ester with other compounds of Formula 21 (where R³ is hydrogen, lower alkyl, aralkyl or heteroaralkyl) and PhtNCH₂SCH₂(R)CHMeSH with other compounds of Formula 20 (e.g., compounds with R² that are prepared according to Example 16A and further exemplified in Example 16B) there are obtained the correspondingly substituted compounds of Formula 22 (where n, R² and R³ are as indicated in the table below).

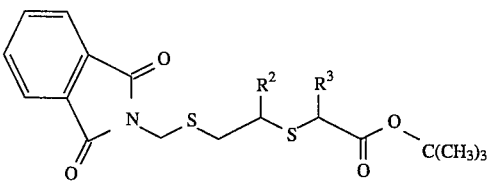

| R² | R³ |
|---|---|
| hydrogen | hydrogen |
| 2-propyl | methyl |
| 2-methylpropyl | 2-propyl |
| 2-butyl | 2-butyl |
| blocked aminoethyl | 2-methylpropyl |
| blocked aminobutyl | blocked 4-hydroxyphenylmethyl |
| carbamoylmethyl | blocked 3-indolylmethyl |
| hydrogen | 4-methoxyphenylmethyl |
| 2-propyl | phenylethyl |
| 2-methylpropyl | phenylethyl |
| 2-butyl | 4-methoxyphenylmethyl |
| blocked aminoethyl | blocked 3-indolylmethyl |
| blocked aminobutyl | blocked 4-hydroxyphenylmethyl |
| carbamoylmethyl | 2-methylpropyl |

| | |
|---|---|
| hydrogen | 2-butyl |
| 2-propyl | 2-propyl |
| 2-methylpropyl | methyl |
| 2-butyl | hydrogen |
| blocked aminoethyl | hydrogen |
| blocked aminobutyl | methyl |
| carbamoylmethyl | 2-propyl | the correspondingly substituted compounds of Formula 23 (where $R^2$ and $R^3$ are as indicated in the table below).

EXAMPLE 18

Preparation of PhtNCH$_2$SCH$_2$(R)CHMe-(S-D-Leu)-OH

18A. Formula 23 Where $R^2$ Is Methyl and $R^3$ Is 2-Methylpropyl

To 172 mg of PhtNCH$_2$SCH$_2$(R)CHMe-(S-D-Leu)-O(t-Bu) was added 0.3 mL of trifluoroacetic acid and 15 mL of water. The reaction mixture was left at 5° C. overnight. The solvent was removed under vacuum and the residue was purified by flash chromatography (45% EtOAc in hexane) to give 67 mg of PhtNCH$_2$SCH$_2$(R)CHMe-(S-D-Leu)-OH as a gum at 45% yield. Characteristic analytical data are as follows: $^1$H NMR (300 MHz, CDCl$_3$) δ7.88 (d, J=5 Hz, 1H), 7.87 (d, J=5 Hz, 1H), 7.75 (d, J=6 Hz, 1H), 7.74 (d, J=6 Hz, 1H), 4.80 (dd14, J=21 Hz, 2H), 3.61 (t, J=7 Hz, 1H), 3.20 (m, 2H), 2.78 (m, 1H), 1.78 (m, 2H), 1.50 (m, 1H), 1.33 (d, J=7 Hz, 3H), 0.97 (d, J=6 Hz, 3H), 0.94 (d, J=6 Hz, 3H); $[\alpha]_D^{25}$ +126° (c=1.34, MeOH).

18B. Preparation of the Corresponding (S) Isomer of Formula 23

By following the procedure described in Example 18A and substituting the (R)-isomer with PhtNCH$_2$SCH$_2$(S)CHMe-(S-D-Leu)-Ot-Bu there is obtained PhtNCH$_2$SCH$_2$(S)CHMe-(S-D-Leu)-OH.

18C. Formula 23 Varying $R^2$

By following the procedures described in Example 18A and substituting PhtNCH$_2$SCH$_2$(R)CHMe-(S-D-Leu)-O(t-Bu) with other compounds of Formula 22 there are obtained the correspondingly substituted compounds of Formula 23 (where $R^2$ and $R^3$ are as indicated in the table below).

Formula 23

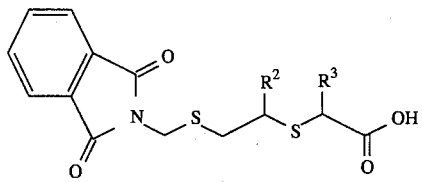

where $R^3$ is 2-methylpropyl

| $R^2$ | Name |
|---|---|
| hydrogen | PhtNCH$_2$SCH$_2$CH$_2$—(S—D—Leu)—OH |
| 2-propyl | PhtNCH$_2$SCH$_2$(R)CH(2-propyl)-(S—D—Leu)—OH |
| 2-methylpropyl | PhtNCH$_2$SCH$_2$(R)CH(2-methylpropyl)-(S—D—Leu)—OH |
| 2-butyl | PhtNCH$_2$SCH$_2$(R)CH(2-butyl)-(S—D—Leu)—OH |
| blocked aminoethyl | PhtNCH$_2$SCH$_2$(R)CH(aminoethyl)-(S—D—Leu)—OH |
| blocked aminobutyl | PhtNCH$_2$SCH$_2$(R)CH(aminobutyl)-(S—D—Leu)—OH |
| carbamoylmethyl | PhtNCH$_2$SCH$_2$(R)CH(carbamoylmethyl)-(S—D—Leu)—OH |

18D. Formula 23 Varying $R^2$

By following the procedures described in Example 18B and substituting PhtNCH$_2$SCH$_2$(S)CHMe-(S-D-Leu)-O(t-Bu) with other compounds of Formula 22 there are obtained Formula 23

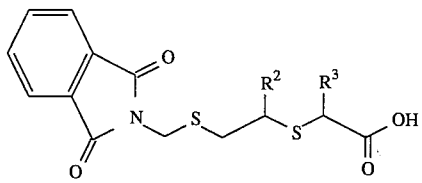

where R³ is 2-methylpropyl

| R² | Name |
|---|---|
| 2-propyl | PhtNCH₂SCH₂(S)CH(2-propyl)-(S—D—Leu)—OH |
| 2-methylpropyl | PhtNCH₂SCH₂(S)CH(2-methylpropyl)-(S—D—Leu)—OH |
| 2-butyl | PhtNCH₂SCH₂(S)CH(2-butyl)-(S—D—Leu)—OH |
| blocked aminoethyl | PhtNCH₂SCH₂(S)CH(aminoethyl)-(S—D—Leu)—OH |
| blocked aminobutyl | PhtNCH₂SCH₂(S)CH(aminobutyl)-(S—D—Leu)—OH |
| carbamoylmethyl | PhtNCH₂SCH₂(S)CH(carbamoylmethyl)-(S—D—Leu)—OH |

18E. Formula 23 Varying R² and R³

By following the procedures described in Example 18A and substituting PhtNCH₂SCH₂(S)CHMe-(S-D-Leu)-O(t-Bu) with other compounds of Formula 22 (e.g., compound prepared according to Examples 17A–17E) there are obtained the correspondingly substituted compounds of Formula 23 (where n, R² and R³ are as indicated in the table below).

Formula 23

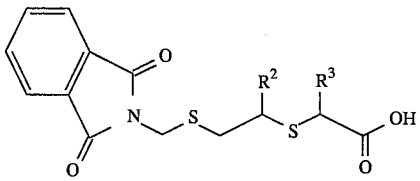

| R² | R³ |
|---|---|
| hydrogen | hydrogen |
| 2-propyl | methyl |
| 2-methylpropyl | 2-propyl |
| 2-butyl | 2-butyl |
| blocked aminoethyl | 2-methylpropyl |
| blocked aminobutyl | blocked 4-hydroxyphenylmethyl |
| carbamoylmethyl | blocked 3-indolylmethyl |
| hydrogen | 4-methoxyphenylmethyl |
| 2-propyl | phenylethyl |
| 2-methylpropyl | phenylethyl |
| 2-butyl | 4-methoxyphenylmethyl |
| blocked aminoethyl | blocked 3-indolylmethyl |
| blocked aminobutyl | blocked 4-hydroxyphenylmethyl |
| carbamoylmethyl | 2-methylpropyl |
| hydrogen | 2-butyl |
| 2-propyl | 2-propyl |
| 2-methylpropyl | methyl |
| 2-butyl | hydrogen |
| blocked aminoethyl | hydrogen |
| blocked aminobutyl | methyl |
| carbamoylmethyl | 2-propyl |

EXAMPLE 19

Preparation of PhtNCH₂SCH₂(R)CHMe-(S-D-Leu)-Phe-NHMe

19A. Formula 24 Where R² Is Methyl, R³ Is 2-Methylpropyl, R⁴ Is Phenylmethyl, R⁵ Is Methyl To a stirred solution of 67 mg of PhtNCH₂SCH₂(R)CHMe-(S-D-Leu)-OH and 32 mg of PheNHMe in 2 mL of 1,2-dimethoxyethane were added 28 mg of 1-hydroxybenzotriazole and 43 mg of dicyclohexylcarbodiimideat 0°–5° C. The reaction mixture was allowed to warm to room temperature and was stirred overnight. The solvent was evaporated and the residue was triturated with 15% $CH_2Cl_2$ in hexane. The filtrate was dried over $Na_2SO_4$ and evaporated under vacuum. Purification of the residue by flash chromatography (35% EtOAc in hexane) afforded 87 mg of PhtNCH₂SCH₂(R)CHMe-(S-D-Leu)-Phe-NHMe as a solid: mp 86°–88° C.; $^1$H NMR (300 MHz, $CDCl_3$) δ7.86 (d, J=6 Hz, 1 H), 7.85 (d, J=6 Hz, 1H), 7.75 (d, J=6 Hz, 1H), 7.74 (d, J=6 Hz, 1H), 7.67 (d, J=8 Hz, 1H), 6.10 (m, 1H), 4.98 (d, J=15 Hz, 1H), 4.71 (q, J=8 Hz, 1H), 4.63 (d, J=15 Hz, 1H), 3.54 (dd, J=6, 9 Hz, 1H), 2.88–3.18 (m, 4H), 2.74 (d, J=5 Hz, 3H), 2.42 (dd, J=11, 14 Hz, 1H), 1.66–1.78 (m, 1H), 1.45–1.53 (m, 1H), 1.26–1.38 (m, 1H 1.24 (d, J=7 Hz, 3H), 0.87 (d, J=7 Hz, 3H), 0.84 (d, J=6 Hz, 3H).

19B. Preparation of the Corresponding (S) Isomer of Formula 24

By following the procedure described in Example 1A and substituting the (R)-isomer with PhtNCH₂SCH₂(S)CHMe-(S-D-Leu)-OH there is obtained PhtNCH₂SCH₂(S) CHMe-(S-D-Leu)-Phe-NHMe.

19C. Formula 24 Varying R²

By following the procedures described in Example 19A and substituting PhtNCH₂SCH₂(R)CHMe-(S-D-Leu)-OH with other compounds of Formula 23 there are obtained the correspondingly substituted compounds of Formula 24 (where R², R³ R⁴, R⁵ and R⁶ are as indicated in the table below).

Formula 24

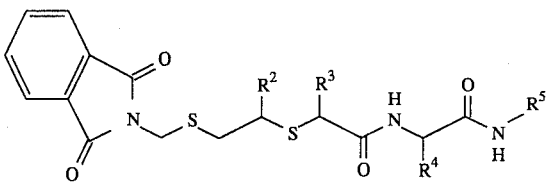

where R³ is 2-methylpropyl, R⁴ is phenylmethyl,
R⁵ is methyl

| R² | Name |
|---|---|
| hydrogen | PhtNCH₂SCH₂CH₂ — (S — D — Leu) — Phe — NHMe |
| 2-propyl | PhtNCH₂SCH₂(R)CH(2-propyl)-(S — D — Leu) — Phe — NHMe |
| 2-methylpropyl | PhtNCH₂SCH₂(R)CH(2-methylpropyl)-(S — D — Leu) — Phe — NHMe |
| 2-butyl | PhtNCH₂SCH₂(R)CH(2-butyl)-(S — D — Leu) — Phe — NHMe |
| blocked aminoethyl | PhtNCH₂SCH₂(R)CH(aminoethyl)-(S — D — Leu) — Phe — NHMe |
| blocked aminobutyl | PhtNCH₂SCH₂(R)CH(aminobutyl)-(S — D — Leu) — Phe — NHMe |
| carbamoylmethyl | PhtNCH₂SCH₂(R)CH(carbamoylmethyl)-(S — D — Leu) — Phe — NHMe |

19D. Formula 24 Varying $R^2$

By following the procedures described in Example 19B and substituting PhtNCH₂SCH₂(S)CHMe-(S-D-Leu)-OH with other compounds of Formula 23 there are obtained the correspondingly substituted compounds of Formula 24 (where $R^2$, $R^3$, $R^4$, $R^5$ and $R^6$ are as indicated in the table below).

Formula 24

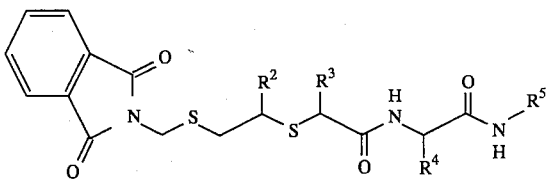

where R³ is 2-methylpropyl, R⁴ is phenylmethyl,
R⁵ is methyl

| R² | Name |
|---|---|
| 2-propyl | PhtNCH₂SCH₂(S)CH(2-propyl)-(S — D — Leu) — Phe — NHMe |
| 2-methylpropyl | PhtNCH₂SCH₂(S)CH(2-methylpropyl)-(S — D — Leu) — Phe — NHMe |
| 2-butyl | PhtNCH₂SCH₂(S)CH(2-butyl)-(S — D — Leu) — Phe — NHMe |
| blocked aminoethyl | PhtNCH₂SCH₂(S)CH(aminoethyl)-(S — D — Leu) — Phe — NHMe |
| blocked aminobutyl | PhtNCH₂SCH₂(S)CH(aminobutyl)-(S — D — Leu) — Phe — NHMe |
| carbamoylmethyl | PhtNCH₂SCH₂(S)CH(carbamoylmethyl)-(S — D — Leu) — Phe — NHMe |

19E. Formula 24 Varying n, $R^2$, $R^3$, $R^4$, $R^5$ and $R^6$

By following the procedures described in Example 19A and substituting PhtNCH₂SCH₂(R)CHMe-(S-D-Leu)-OH with other compounds of Formula 23 (e.g., compounds with $R^2$ and $R^3$) and PheNHMe with other compounds of Formula 6 (e.g., compounds with $R^4$, $R^5$ and $R^6$) there are obtained the correspondingly substituted compounds of Formula 24 (where n, $R^2$, $R^3$, $R^4$, $R^5$ and $R^6$ are as indicated in the table below).

Formula 24

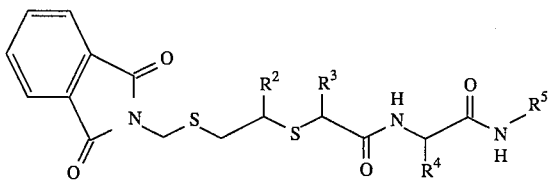

where $R^5$ is methyl or phenylmethyl

| $R^2$ | $R^3$ | $R^4$ | $R^5$ |
|---|---|---|---|
| hydrogen | hydrogen | phenylethyl | —CH₃ |
| 2-propyl | methyl | 4-methoxyphenyl-methyl | —Bn |
| 2-methylpropyl | 2-propyl | blocked 3-indolylmethyl | —CH₃ |
| 2-butyl | 2-butyl | blocked 4-hydroxy-phenylmethyl | —Bn |
| blocked aminoethyl | 2-methylpropyl | benzyl | —CH₃ |
| blocked aminobutyl | blocked 4-hydroxy-phenylmethyl | blocked 4-imidazoylmethyl | —Bn |
| carbamoylmethyl | blocked 3-indolylmethyl | blocked 3-guanylpropyl | —CH₃ |
| hydrogen | 4-methoxyphenylmethyl | blocked 4-aminobutyl | —Bn |
| 2-propyl | phenylethyl | 2-methylpropyl | —CH₃ |
| 2-methylpropyl | phenylethyl | 2-butyl | —Bn |
| 2-butyl | 4-methoxyphenylmethyl | 2-propyl | —CH₃ |
| blocked aminoethyl | blocked 3-indolylmethyl | methyl | —Bn |
| blocked aminobutyl | blocked 4-hydroxy-phenylmethyl | hydrogen | —CH₃ |
| carbamoylmethyl | 2-methylpropyl | hydrogen | —Bn |
| hydrogen | 2-butyl | methyl | —CH₃ |
| 2-propyl | 2-propyl | 2-propyl | —Bn |
| 2-methylpropyl | methyl | 2-butyl | —CH₃ |
| 2-butyl | hydrogen | 2-methylpropyl | —Bn |
| blocked aminoethyl | hydrogen | blocked 4-aminobutyl | —CH₃ |
| blocked aminobutyl | methyl | blocked 3-guanylpropyl | —Bn |
| carbamoylmethyl | 2-propyl | 2-butyl | —Bn |

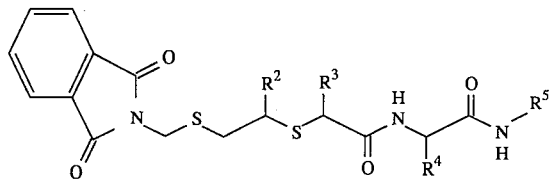

Formula 24 where R⁵ is —CH(R⁶)—C(O)NH₂

| R² | R³ | R⁴ | R⁶ |
|---|---|---|---|
| hydrogen | hydrogen | phenylethyl | hydrogen |
| 2-propyl | methyl | 4-methoxy-phenylmethyl | 2-propyl |
| 2-methylpropyl | 2-propyl | blocked 3-indolylmethyl | methyl |
| 2-butyl | 2-butyl | blocked 4-hydroxyphenyl-methyl | 2-butyl |
| blocked aminoethyl | 2-methylpropyl | benzyl | 2-methylpropyl |
| blocked aminobutyl | blocked 4-hydroxy-phenylmethyl | blocked 4-imidazoylmethyl | blocked 4-aminobutyl |
| carbamoylmethyl | blocked 3-indolyl-methyl | blocked 3-guanylpropyl | blocked 3-guanylpropyl |
| hydrogen | 4-methoxyphenylmethyl | blocked 4-aminobutyl | 2-imidazoyl-methyl |
| 2-propyl | phenylethyl | 2-methylpropyl | hydroxymethyl |
| 2-methylpropyl | phenylethyl | 2-butyl | 1-hydroxyethyl |
| 2-butyl | 4-methoxyphenylmethyl | 2-propyl | thiolmethyl |
| blocked aminoethyl | blocked 3-indolyl-methyl | methyl | methylthio-ethyl |
| blocked aminobutyl | blocked 4-hydroxy-phenylmethyl | hydrogen | methylthio-ethyl |
| carbamoylmethyl | 2-methylpropyl | hydrogen | thiolmethyl |
| hydrogen | 2-butyl | methyl | 1-hydroxyethyl |
| 2-propyl | 2-propyl | 2-propyl | hydroxymethyl |
| 2-methylpropyl | methyl | 2-butyl | 2-imidazoyl-methyl |
| 2-butyl | hydrogen | 2-methylpropyl | blocked 3-guanylpropyl |
| blocked aminoethyl | hydrogen | blocked 4-aminobutyl | blocked 4-aminobutyl |
| blocked aminobutyl | methyl | blocked 3-guanylpropyl | 2-methylpropyl |
| carbamoylmethyl | 2-propyl | 2-butyl | hydrogen |

EXAMPLE 20

Preparation of 2-NO₂C₆H₄SSCH₂(R)CHMe-(S-D-Leu)-Phe-NHMe

20A. Formula 25 Where R² Is Methyl, R³ Is 2-Methylpropyl R⁴ Is Phenylmethyl, R⁵ Is Methyl To a solution of 87 mg of PhtNCH₂SCH₂(R)CHMe-(S-D-Leu)-Phe-NHMe in 1 mL of acetic acid was added 34 mg of 2-NO₂C₆H₄SCl. The mixture was stirred at room temperature for 17 h. The acetic acid was evaporated under vacuum and the residue was purified by flash chromatography (5% EtOAc in CH₂Cl₂) to give mg of 2-NO₂C₆H₄SSCH₂(R)CHMe-(S-D-Leu)-Phe-NHMe at 65% yield. Characteristic analytical data are as follows: ¹H NMR (300 MHz, CDCl₃) δ8.27 (dd, J=1, 8 Hz, 1H), 8.23 (dd, J=1, 8 Hz, 1H), 7.69 (dr, J=1, 7 Hz, 1H), 7.21–7.39 (m, 6H), 6.98 (d, J=8 Hz, 1H), 6.10 (m, 1H), 4.57 (q, J= 8 Hz, 1H), 3.19 (dd, J=6, 8 Hz, 1H), 3.10 (dd, J=7, 14 Hz, 1H), 3.04 (dd, J=8, 14 Hz, 1H), 2.83–2.92 (m, 1H), 2.73 (d, J=5 Hz, 3H), 2.60–2.70 (m, 2H), 1.52–1.69 (m, 2H), 1.40 H), 1.18 (d, J=7 Hz, 3H), 0.82 (d, J=7 Hz, 3H), 0.80 (d, J=7 Hz, 3H).

20B. Preparation of the Corresponding (S) Isomer of Formula 25

By following the procedure described in Example 20A and substituting the (R)-isomer with PhtNCH₂SCH₂(R)CHMe-(S-D-Leu)-Phe-NHMe there is obtained 2-NO₂C₆H₄SSCH₂(R)CHMe-(S-D-Leu)-Phe-NHMe.

20C. Formula 25 Varying R²

By following the procedures described in Example 20A and substituting PhtNCH₂SCH₂(R)CHMe-(S-D-Leu)-Phe-NHMe with other compounds of Formula 24 there are obtained the correspondingly substituted compounds of Formula 25 (where R², R³, R⁴, R⁵ and R⁶ are as indicated in the table below).

Formula 25

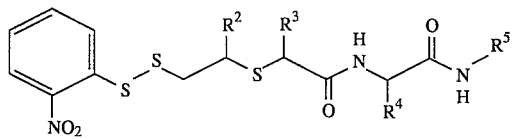

where R³ is 2-methylpropyl, R⁴ is phenylmethyl, R⁵ is methyl

| R² | Name |
|---|---|
| hydrogen | 2-NO₂C₆H₄SSCHCH₂ — (S-D-Leu) — Phe — NHMe |
| 2-propyl | 2-NO₂C₆H₄SSCH₂(R)CH(2-propyl)-(S-D-Leu) — Phe — NHMe |
| 2-methyl-propyl | 2-NO₂CH₄SSCH₂(R)CH(2-methylpropyl)-(S-D-Leu) — Phe — NHMe |
| 2-butyl | 2-NO₂CH₄SSCH₂(R)CH(2-butyl)-(S-D-Leu) — Phe — NHMe |
| blocked aminoethyl | 2-NO₂C₆H₄SSCH₂(R)CH(aminoethyl)-(S-D-Leu) — Phe — NHMe |
| blocked aminobutyl | 2-NO₂C₆H₄SSCH₂(R)CH(aminobutyl)-(S-D-Leu) — Phe — NHMe |
| carbamoyl-methyl | 2-NO₂C₆H₄SSCH₂(R)CH(carbamoylmethyl)-(S-D-Leu) — Phe — NHMe |
| PhtN-ethyl | 2-NO₂C₆H₄SSCH₂(R)CH(PhtN-ethyl)-(S-D-Leu) — Phe — NHMe |
| PhtN-butyl | 2-NO₂C₆H₄SSCH₂(R)CH(PhtN-butyl)-(S-D-Leu) — Phe — NHMe |

20D. Formula 25 Varying R²

By following the procedures described in Example 20B and substituting PhtNCH₂SCH₂(S)CHMe-(S-D-Leu)-Phe-NHMe with other compounds of Formula 24 there are obtained the correspondingly substituted compounds of Formula 25 (where R², R³, R⁴, R⁵ and R⁶ are as indicated in the table below).

Formula 25

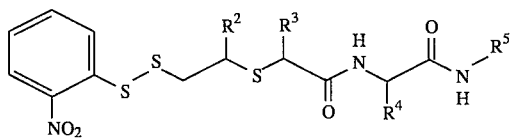

where R³ is 2-methylpropyl, R⁴ is phenylmethyl, R⁵ is methyl

| R² | Name |
|---|---|
| 2-propyl | 2-NO₂C₆H₄SSCH₂(S)CH(2-propyl)-(S-D-Leu) — Phe — NHMe |
| 2-methylpropyl | 2-NO₂C₆H₄SSCH₂(S)CH(2-methylpropyl)-(S-D-Leu) — Phe — NHMe |
| 2-butyl | 2-NO₂C₆H₄SSCH₂(S)CH(2-butyl)-(S-D-Leu) — Phe — NHMe |
| blocked aminoethyl | 2-NO₂C₆H₄SSCH₂(S)CH(aminoethyl)-(S-D-Leu) — Phe — NHMe |
| blocked aminobutyl | 2-NO₂CH₄SSCH₂(S)CH(aminobutyl)-(S-D-Leu) — Phe — NHMe |
| carbamoylmethyl | 2-NO₂CH₄SSCH₂(S)CH(carbamoylmethyl)-(S-D-Leu) — Phe — NHMe |
| PhtN-ethyl | 2-NO₂C₆H₄SSCH₂(S)CH(PhtN-ethyl)-(S-D-Leu) — Phe — NHMe |
| PhtN-butyl | 2-NO₂C₆H₄SSCH₂(S)CH(PhtN-butyl)-(S-D-Leu) — Phe — NHMe |

20E. Formula 25 Varying n, R², R³, R⁴, R⁵ and R⁶

By following the procedures described in Example 20A and substituting PhtNCH₂SCH₂(R)CHMe-(S-D-Leu)-Phe-NHMe with other compounds of Formula 24 (e.g., compound prepared according to Examples 19A-19E) there are obtained the correspondingly substituted compounds of Formula 25 (where n, R², R³, R⁴, R⁵ and R⁶ are as indicated in the tables below).

Formula 25

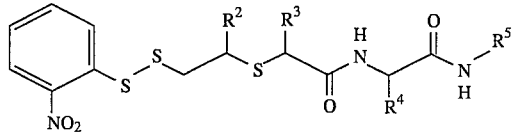

where R⁵ is methyl or phenylmethyl

| R² | R³ | R⁴ | R⁵ |
|---|---|---|---|
| hydrogen | hydrogen | phenylethyl | —CH₃ |
| 2-propyl | methyl | 4-methoxyphenyl-methyl | —Bn |
| 2-methyl-propyl | 2-propyl | blocked 3-indolylmethyl | —CH₃ |
| 2-butyl | 2-butyl | blocked 4-hydroxy-phenylmethyl | —Bn |
| blocked aminoethyl | 2-methylpropyl | benzyl | —CH₃ |
| blocked aminobutyl | blocked 4-hydroxy-phenylmethyl | blocked 4-imidazoylmethyl | —Bn |
| carbamoyl-methyl | blocked 3-indolylmethyl | blocked 3-guanylpropyl | —CH₃ |
| hydrogen | 4-methoxyphenyl-methyl | blocked 4-aminobutyl | —Bn |
| 2-propyl | phenylethyl | 2-methylpropyl | —CH₃ |
| 2-methyl-propyl | phenylethyl | 2-butyl | —Bn |
| 2-butyl | 4-methoxyphenyl-methyl | 2-propyl | —CH₃ |
| blocked aminoethyl | blocked 3-indolylmethyl | methyl | —Bn |
| blocked aminobutyl | blocked 4-hydroxy-phenylmethyl | hydrogen | —CH₃ |
| carbamoyl-methyl | 2-methylpropyl | hydrogen | —Bn |
| hydrogen | 2-butyl | methyl | —CH₃ |
| 2-propyl | 2-propyl | 2-propyl | —Bn |
| 2-methyl-propyl | methyl | 2-butyl | —CH₃ |
| 2-butyl | hydrogen | 2-methylpropyl | —Bn |
| blocked aminoethyl | hydrogen | blocked 4-aminobutyl | —CH₃ |
| blocked aminobutyl | methyl | blocked 3-guanylpropyl | —Bn |
| carbamoyl-methyl | 2-propyl | 2-butyl | —Bn |

Formula 25

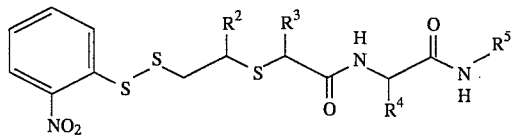

where R⁵ is —CH(R⁶)—C(O)NH₂

| R² | R³ | R⁴ | R⁶ |
|---|---|---|---|
| hydrogen | hydrogen | phenylethyl | hydrogen |
| 2-propyl | methyl | 4-methoxy-phenylmethyl | 2-propyl |
| 2-methyl-propyl | 2-propyl | blocked 3-indolylmethyl | methyl |
| 2-butyl | 2-butyl | blocked 4-hydroxyphenyl-methyl | 2-butyl |
| blocked aminoethyl | 2-methylpropyl | benzyl | 2-methylpropyl |

-continued

Formula 25

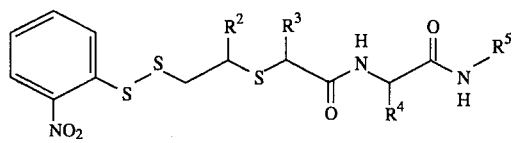

where $R^5$ is $-CH(R^6)-C(O)NH_2$

| $R^2$ | $R^3$ | $R^4$ | $R^6$ |
|---|---|---|---|
| blocked aminobutyl | blocked 4-hydroxyphenylmethyl | blocked 4-imidazoylmethyl | blocked 4-aminobutyl |
| carbamoylmethyl | blocked 3-indolylmethyl | blocked 3-guanylpropyl | blocked 3-guanylpropyl |
| hydrogen | 4-methoxyphenylmethyl | blocked 4-aminobutyl | 2-imidazoylmethyl |
| 2-propyl | phenylethyl | 2-methylpropyl | hydroxymethyl |
| 2-methylpropyl | phenylethyl | 2-butyl | 1-hydroxyethyl |
| 2-butyl | 4-methoxyphenylmethyl | 2-propyl | thiolmethyl |
| blocked aminoethyl | blocked 3-indolylmethyl | methyl | methylthioethyl |
| blocked aminobutyl | blocked 4-hydroxyphenylmethyl | hydrogen | methylthioethyl |
| carbamoylmethyl | 2-methylpropyl | hydrogen | thiolmethyl |
| hydrogen | 2-butyl | methyl | 1-hydroxyethyl |
| 2-propyl | 2-propyl | 2-propyl | hydroxymethyl |
| 2-methylpropyl | methyl | 2-butyl | 2-imidazoylmethyl |
| 2-butyl | hydrogen | 2-methylpropyl | blocked 3-guanylpropyl |
| blocked aminoethyl | hydrogen | blocked 4-aminobutyl | blocked 4-aminobutyl |
| blocked aminobutyl | methyl | blocked 3-guanylpropyl | 2-methylpropyl |
| carbamoylmethyl | 2-propyl | 2-butyl | hydrogen |

EXAMPLE 21

Preparation of HSCH$_2$(R)CHMe-(S-D-Leu)-Phe-NHMe

21A. Formula I Where $R^2$ Is Methyl, $R^3$ Is 2-Methylpropyl, $R^4$ Is Phenylmethyl, $R^5$ Is Methyl To a solution of 30 mg of 2-NO$_2$C$_6$H$_4$SSCH$_2$(R)CHMe-(S-D-Leu)-Phe-NHMe in 0.4 mL of MeOH and 0.1 mL of dioxane was added 0.09 mL of 2-mercaptoethanol and 0.14 mL of 0.4M NaOH. The mixture was stirred at room temperature under nitrogen for 30 min, poured into water, acidified with acetic acid and extracted with CH$_2$Cl$_2$. The organic layer was dried over Na$_2$SO$_4$ and evaporated under vacuum. Purification of the residue by flash chromatography (25% EtOAc in hexane) afforded 12 mg of HSCH$_2$(R)CHMe-(S-D-Leu)-Phe-NHMe as a solid at 56% yield. Characteristic analytical data are as follows: mp 153°–155° C.; $^1$H NMR (300 MHz, CDCl$_3$) δ7.20–7.34 (m, 5H), 7.11 (d, J=8 Hz, 1H), 5.96 (m, 1H), 4.64 (q, J=8 Hz, 1H), 3.34 (dd, J=6, 9 Hz, 1H), 3.14 (dd, J=7, 14 Hz, 1H), 3.08 (dd, J=8, 14 Hz, 1H), 2.75 (d, J=5 Hz, 3H), 2.64–2.73 (m, 1H), 2.44–2.60 (m, 2H), 1.40–1.72 (m, 3H), 1.53 (t, J=8 Hz, 1H, SH), 1.15 (d, J=7 Hz, 3H), 0.89 (d, J=7 Hz, 3H), 0.88 (d, J=7 Hz, 3H).

21B. Preparation of the Corresponding (S) Isomer of Formula I

By following the procedure described in Example 21A and substituting the (R)-isomer with 2-NO$_2$C$_6$H$_4$SSCH$_2$(S)CHMe-(S-D-Leu)-Phe-NHMe there is obtained HSCH$_2$(S)CHMe-(S-D-Leu)-Phe-NHMe.

21C. Formula I Varying $R^2$

By following the procedures described in Example 21A and substituting 2-NO$_2$C$_6$H$_4$SSCH$_2$(R)CHMe-(S-D-Leu)-Phe-NHMe with other compounds of Formula 25 there are obtained the correspondingly substituted compounds of Formula I (where $R^2$, $R^3$, $R^4$, $R^5$ and $R^6$ are as indicated in the table below).

Formula I

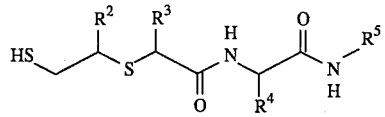

where $R^3$ is 2-methylpropyl, $R^4$ is phenylmethyl, $R^5$ is methyl

| $R^2$ | Name |
|---|---|
| hydrogen | HSCH$_2$CH$_2$—(S-D-Leu)—Phe—NHMe |
| 2-propyl | HSCH$_2$(R)CH(2-propyl)-(S-D-Leu)—Phe—NHMe |
| 2-methylpropyl | HSCH$_2$(R)CH(2-methylpropyl)-(S-D-Leu)—Phe—NHMe |
| 2-butyl | HSCH$_2$(R)CH(2-butyl)-(S-D-Leu)—Phe—NHMe |
| aminoethyl | HSCH$_2$(R)CH(aminoethyl)-(S-D-Leu)—Phe—NHMe |
| aminobutyl | HSCH$_2$(R)CH(aminobutyl)-(S-D-Leu)—Phe—NHMe |
| carbamoylmethyl | HSCH$_2$(R)CH(carbamoylmethyl)-(S-D-Leu)—Phe—NHMe |
| PhtN-ethyl | HSCH$_2$(R)CH(PhtN-ethyl)-(S-D-Leu)—Phe—NHMe |
| PhtN-butyl | HSCH$_2$(R)CH(PhtN-butyl)-(S-D-Leu)—Phe—NHMe |

21D. Formula I Varying $R^2$

By following the procedures described in Example 21B and substituting 2-NO$_2$C$_6$H$_4$SSCH$_2$(S)CHMe-(S-D-Leu)-Phe-NHMe with other compounds of Formula 25 there are obtained the correspondingly substituted compounds of Formula I (where $R^2$, $R^3$, $R^4$, $R^5$ and $R^6$ are as indicated in the table below).

Formula I

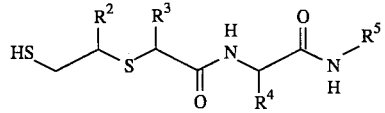

where $R^3$ is 2-methylpropyl, $R^4$ is phenylmethyl, $R^5$ is methyl

| $R^2$ | Name |
|---|---|
| 2-propyl | HSCH$_2$(S)CH(2-propyl)-(S-D-Leu)—Phe—NHMe |
| 2-methylpropyl | HSCH$_2$(S)CH(2-methylpropyl)-(S-D-Leu)—Phe—NHMe |
| 2-butyl | HSCH$_2$(S)CH(2-butyl)-(S-D-Leu)—Phe—NHMe |
| aminoethyl | HSCH$_2$(S)CH(aminoethyl)-(S-D-Leu)—Phe—NHMe |
| aminobutyl | HSCH$_2$(S)CH(aminobutyl)-(S-D-Leu)—Phe—NHMe |
| carbamoylmethyl | HSCH$_2$(S)CH(carbamoylmethyl)-(S-D-Leu)—Phe—NHMe |
| PhtN-ethyl | HSCH$_2$(S)CH(PhtN-ethyl)-(S-D-Leu)—Phe—NHMe |
| PhtN-butyl | HSCH$_2$(S)CH(PhtN-butyl)-(S-D-Leu)— |

-continued

Formula I

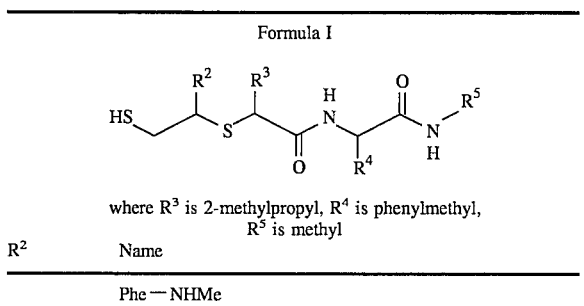

where R³ is 2-methylpropyl, R⁴ is phenylmethyl,
R⁵ is methyl

| R² | Name |
|---|---|
| | Phe—NHMe |

21E. Formula I Varying $R^2$, $R^3$, $R^4$, $R^5$ and $R^6$

By following the procedures described in Example 21A and substituting 2-NO₂C₆H₄SSCH₂(R)CHMe-(S-D-Leu)-Phe-NHMe with other compounds of Formula 25 (e.g., compounds prepared according to Examples 20A–20E) there are obtained the correspondingly substituted compounds of Formula I (where n, $R^2$, $R^3$, $R^4$, $R^5$ and $R^6$ are as indicated in the tables below).

Formula I

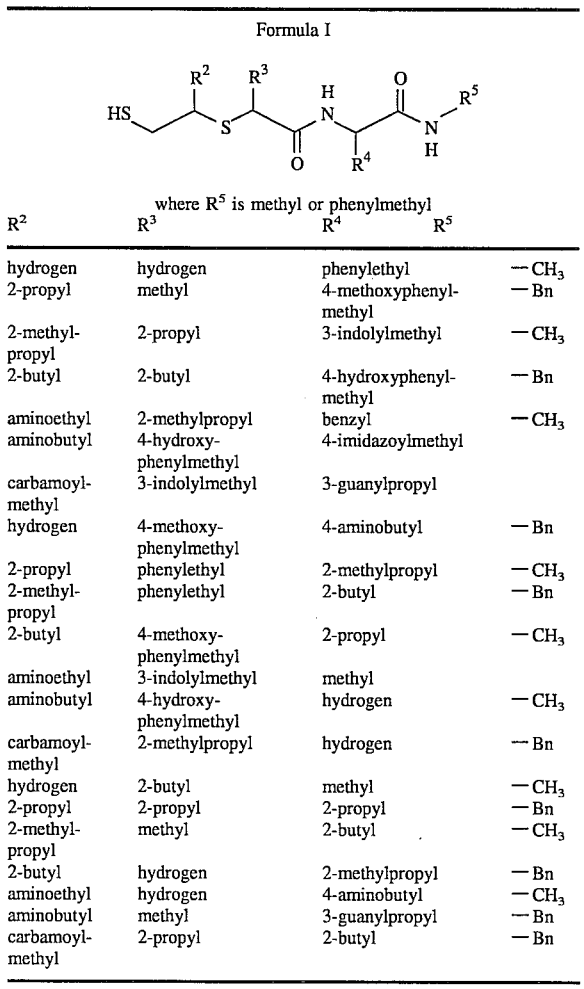

where R⁵ is methyl or phenylmethyl

| R² | R³ | R⁴ | R⁵ |
|---|---|---|---|
| hydrogen | hydrogen | phenylethyl | —CH₃ |
| 2-propyl | methyl | 4-methoxyphenyl-methyl | —Bn |
| 2-methyl-propyl | 2-propyl | 3-indolylmethyl | —CH₃ |
| 2-butyl | 2-butyl | 4-hydroxyphenyl-methyl | —Bn |
| aminoethyl | 2-methylpropyl | benzyl | —CH₃ |
| aminobutyl | 4-hydroxy-phenylmethyl | 4-imidazoylmethyl | |
| carbamoyl-methyl | 3-indolylmethyl | 3-guanylpropyl | |
| hydrogen | 4-methoxy-phenylmethyl | 4-aminobutyl | —Bn |
| 2-propyl | phenylethyl | 2-methylpropyl | —CH₃ |
| 2-methyl-propyl | phenylethyl | 2-butyl | —Bn |
| 2-butyl | 4-methoxy-phenylmethyl | 2-propyl | —CH₃ |
| aminoethyl | 3-indolylmethyl | methyl | |
| aminobutyl | 4-hydroxy-phenylmethyl | hydrogen | —CH₃ |
| carbamoyl-methyl | 2-methylpropyl | hydrogen | —Bn |
| hydrogen | 2-butyl | methyl | —CH₃ |
| 2-propyl | 2-propyl | 2-propyl | —Bn |
| 2-methyl-propyl | methyl | 2-butyl | —CH₃ |
| 2-butyl | hydrogen | 2-methylpropyl | —Bn |
| aminoethyl | hydrogen | 4-aminobutyl | —CH₃ |
| aminobutyl | methyl | 3-guanylpropyl | —Bn |
| carbamoyl-methyl | 2-propyl | 2-butyl | —Bn |

Formula I

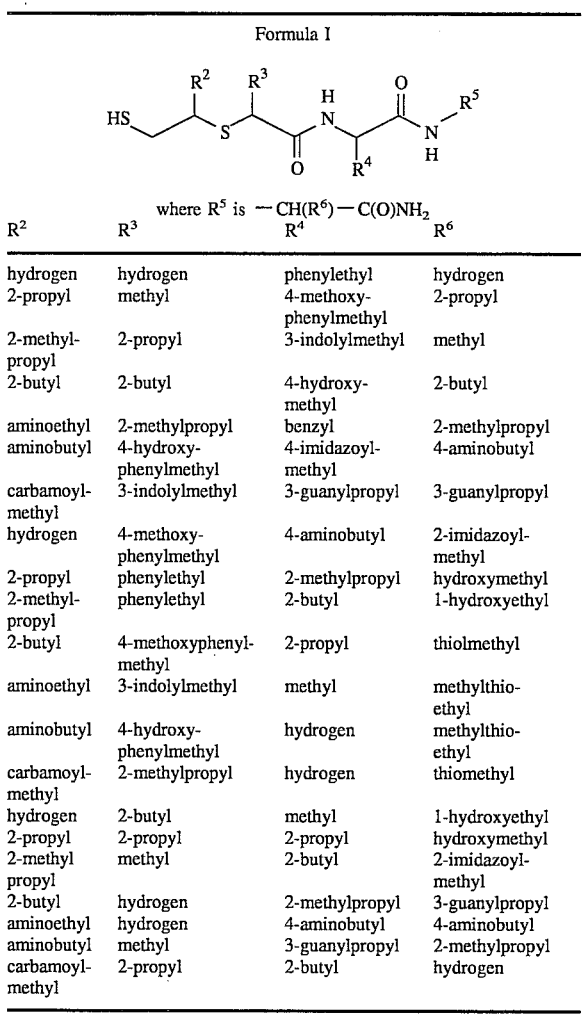

where R⁵ is —CH(R⁶)—C(O)NH₂

| R² | R³ | R⁴ | R⁶ |
|---|---|---|---|
| hydrogen | hydrogen | phenylethyl | hydrogen |
| 2-propyl | methyl | 4-methoxy-phenylmethyl | 2-propyl |
| 2-methyl-propyl | 2-propyl | 3-indolylmethyl | methyl |
| 2-butyl | 2-butyl | 4-hydroxy-methyl | 2-butyl |
| aminoethyl | 2-methylpropyl | benzyl | 2-methylpropyl |
| aminobutyl | 4-hydroxy-phenylmethyl | 4-imidazoyl-methyl | 4-aminobutyl |
| carbamoyl-methyl | 3-indolylmethyl | 3-guanylpropyl | 3-guanylpropyl |
| hydrogen | 4-methoxy-phenylmethyl | 4-aminobutyl | 2-imidazoyl-methyl |
| 2-propyl | phenylethyl | 2-methylpropyl | hydroxymethyl |
| 2-methyl-propyl | phenylethyl | 2-butyl | 1-hydroxyethyl |
| 2-butyl | 4-methoxyphenyl-methyl | 2-propyl | thiolmethyl |
| aminoethyl | 3-indolylmethyl | methyl | methylthio-ethyl |
| aminobutyl | 4-hydroxy-phenylmethyl | hydrogen | methylthio-ethyl |
| carbamoyl-methyl | 2-methylpropyl | hydrogen | thiomethyl |
| hydrogen | 2-butyl | methyl | 1-hydroxyethyl |
| 2-propyl | 2-propyl | 2-propyl | hydroxymethyl |
| 2-methyl propyl | methyl | 2-butyl | 2-imidazoyl-methyl |
| 2-butyl | hydrogen | 2-methylpropyl | 3-guanylpropyl |
| aminoethyl | hydrogen | 4-aminobutyl | 4-aminobutyl |
| aminobutyl | methyl | 3-guanylpropyl | 2-methylpropyl |
| carbamoyl-methyl | 2-propyl | 2-butyl | hydrogen |

EXAMPLE 22

22A. Preparation of Formula 6

1. Formula 6 Where $R^4$ Is Phenylmethyl and $R^5$ Is —CH($R^6$)—C(O)NH₂ Where $R^6$ Is Methyl The following procedure for the preparation of the amino acid residue is a modification of the procedures reported in Bodanszky, M.; Bodanszky, A. *The Practice of Peptide Synthesis;* Springer-Verlag: New York, 1984; p 129–142. A mixture of 5.00 g of Cbz-Phe-OH (Sigma Chemical Company), 2.12 g of N-hydroxysuccinimide and 3.79 g of 1,3-dicyclohexylcarbodiimide in 20 mL of dry THF was kept at 4° C. under N₂ for 26 h. The resulting precipitate was removed by filtration. To the filtrate was added an aqueous solution of 1.79 g of Ala-OH containing 0.802 g of NaOH. The mixture was stirred at room temperature for 18 h. The solid was removed by filtration and the filtrate was diluted with saturated aqueous NaHCO₃ and extracted with CHCl₃. The aqueous layer was acidified with 1M HCl and the resulting precipitate was collected by filtration, washed with water, and dried under vacuum to give 6.00 g (97% yield) of Cbz-Phe-Ala-OH, which was used without further purification. Characteristic analytical data are as follows: mp 153°–154° C.; ¹H NMR (300 MHz, CDCl₃ —CD₃OD)

δ7.38–7.10 (m, 10H, 2×Ph), 6.91– 6.80 (br, 1H, H—N), 5.60–5.52 (br, 1H, H—N), 5.03 (s, 2H, CH$_2$-Bn), 4.45–4.38 (m, 2H, Hα-(Phe)+Hα-(Ala)), 3.01 (m, 2H, CH$_2$-(Phe)), 1.35 (d, J= 7 Hz, 3H, CH$_3$-(Ala)).

The above described procedure was repeated using 5.65 g of Cbz-Phe-Ala-OH and excess anhydrous ammonia in THF to obtain 7.16 g of crude Cbz-Phe-Ala-NH$_2$. The crude product was then subjected to hydrogenolysis in MeOH over 10% Pd/C to afford 3.42 g (95% yield) of Phe-Ala-NH$_2$ as a yellow solid after flash chromatography (EtOAc-MeOH 10:1). Characteristic analytical data are as follows: mp 95°–97° C.; R$_F$ 0.10 (1:2 MeOH:EtOAc); $^1$H NMR (300 MHz, CDCl$_3$) δ 7.80–7.72 (br, 1H, H—N), 7.35–7.18 (m, 5H, Ph), 6.58–6.45 (br, 1H, H—N), 5.70–5.60 (br, 1H, H—N), 4.46 (quint, J=7 Hz, 1H, Hα-(Ala)), 3.62 (dd, J=4, 9 Hz, 1H, Hα-(Phe)), 3.21 (dd, J=4, 11 Hz, 1H, Hβ-(Phe)), 2.72 (dd, J=9, 11 Hz, 1H, Hβ-(Phe)), 1.35 (d, J=7 Hz, 3H, CH$_3$); $^{13}$C NMR (75 MHz, CDCl$_3$) δ175.3 (C=O), 174.8 (C=O), 137.6 (C-Ph), 129.4 (CH-Ph), 128.8 (CH-Ph), 127.0 (CH-Ph), 56.0 (CH-α), 48.0 (CH-α), 40.5 (CH$_2$), 17.7 (CH$_3$); [α]$_D^{25}$ − 25.6° (C=1.90, EtOH).

2. Formula 6 Where R$^4$ Is 3-indolylmethyl and R$^5$ Is Phenylmethyl

The coupling procedure described above for the preparation of Cbz-Phe-Ala-NH$_2$ was employed using 10.0 g of Cbz-Trp-OH (Sigma Chemical Company) and 4.84 mL of freshly distilled BnNH$_2$ in dry THF to give 11.3 g (89% yield) of crystalline Cbz-Trp-NHBn. Characteristic analytical data are as follows: mp 104°–105° C.; $^1$H NMR (300 MHz, CDCl$_3$) δ8.00–6.88 (m, 16H, Ar), 5.85 (br, 1H, H-α), 5.45 (br, 1H, H—N), 5.10 (s, 2H, CH$_2$—O), 4.57–4.45 (br, H—), 4.27 (t, 6H, CH$_2$—N), 3.38 (dd, J=4, 14 Hz, 1H, H-β), 3.16 (dd, J=8, 14 Hz, 1H, H-β); mass spectrum (EI), m/e 427 (M$^+$), 336 (M$^+$-Bn), 277 (M$^+$ -Cbz-NH), 130 (M$^{30}$ -Cbz-NH—CH—CONH-Bn), 91 (Bn$^+$); [α]$_D^{25}$ +7.0° (c=0.20, EtOAc).

A solution of 2.20 g (5.15 mmol) Cbz-Trp-NHBn in 60 mL of MeOH was subjected to hydrogenolysis over Pd/C to give 1.43 g (4.88 mmol, 95%) of Trp-NHBn. Characteristic analytical data are as follows: mp 112°–114° C.; $^1$H NMR (300 MHz, CDCl$_3$) δ8.40–7.00 (m, 11H, Ar), 4.44 (d, J=6 Hz, 2H, CH$_2$ —N), 3.77 (dd, J=4 Hz, 9H, H-α), 3.42 (dd, J=4, 14 Hz, 1H, H-β), 2.98 (dd, J=9, 14 Hz, 1H, H-β); mass spectrum (EI), m/e 293 (M$^+$), 277 (M$^+$-NH$_2$), 130 (M +-H$_2$N—CH—CONH-Bn); [α]$_D^{25}$ +42.1° (c=1.02, MeOH).

3. Formula 6 Where R$^4$ Is Phenylmethyl and R$^5$ Is Methyl

A mixture of 1.00 g of Cbz-Phe-OH (Sigma Chemical Company), 0.385 g of N-hydroxysuccinimide and 0.541 g of 1,3-dicyclohexylcarbodiimide in 5 mL of dry THF was kept at 4° C. under N$_2$ overnight. The resulting precipitate was removed by filtration, and to the filtrate was added excess 40% aqueous methylamine at room temperature. The mixture was stirred at room temperature for 30 min. The solid was removed by filtration and the filtrate was partitioned between saturated aqueous NaHCO$_3$ and CH$_2$Cl$_2$. The organic layer was separated, dried over anhydrous Na$_2$SO$_4$, and evaporated under reduced pressure to give 1.12 g of the crude Cbz-Phe-NHMe.

To a solution of the crude product in 30 mL of MeOH was added 0.21 g of 10% Pd/C and H$_2$ was bubbled through the mixture via a dispersion tube until TLC analysis showed completion of the hydrogenolysis (3 h). The catalyst was removed by filtration and the solvent was evaporated under reduced pressure. The residue was partitioned between CHCl$_3$ and water and the aqueous layer was acidified with 1M HCl to approximately pH 2 and was extracted with CHCl$_3$ (3×). The aqueous layer was then neutralized with 10% NaOH and again was extracted with CHCl$_3$ (3×). The latter organic extract was dried over anhydrous Na$_2$SO$_4$ and was evaporated under reduced pressure to give 0.554 g (93% yield) of Phe-NHMe. Characteristic analytical data are as follows: mp 48°–50° C.; R$_F$ 0.10 (EtOAc); $^1$H NMR (300 MHz, CDCl$_3$) δ7.34–7.20 (m, 5H, Ph), 3.60 (dd, J=4, 9 Hz, 1H, H-α), 3.30 (dd, J=4, 11 Hz, 1H, H-β), 2.81 (d, 5H, CH$_3$—N), 2.65 (dd, J=9, 11 Hz, 1H, H-β); $^{13}$C NMR (75 MHz, CDCl$_3$) δ175.6 (C=O), 138.6 (C-Ph), 129.9 (CH-Ph), 129.3 (CH-Ph), 127.3 (CH-Ph), 56.8 (CH$_3$), 41.3 (CH), 26.0 (CH$_2$); mass spectrum (PCI), m/e 179 (M+1); [α]$_D^{25}$ +8.5° (c=4.20, EtOH).

5B. Formula 6 Varying R$^4$, R$^5$ and R$^6$

By following the procedures described in Example 5A and substituting CBz-Phe-OH and Ala-OH with other compounds of Formulae 6A and 6B, respectively [where the substituents R$^4$ (Formula 6A), and R$^5$ and R$^6$ (Formula 6B) are as indicated in the table below] there are obtained the correspondingly substituted compounds of Formula 6.

Formula 6

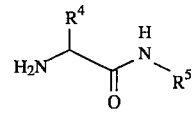

where R$^5$ is methyl or phenylmethyl

| R$^4$ | R$^5$ | Name |
|---|---|---|
| hydrogen | —CH$_3$ | Gly—CH$_3$ |
| methyl | —Bn | Ala—Bn |
| 2-propyl | —CH$_3$ | Val—CH$_3$ |
| 2-butyl | —Bn | Leu—Bn |
| 2-methylpropyl | —CH$_3$ | Ile—CH$_3$ |
| blocked 4-aminobutyl | —Bn | Lys—Bn |
| blocked 3-guanylpropyl | —CH$_3$ | Arg—CH$_3$ |
| blocked 4-imidazoylmethyl | —Bn | His—Bn |
| benzyl | —CH$_3$ | Phe—CH$_3$ |
| blocked 4-hydroxyphenylmethyl | —Bn | Tyr—Bn |
| blocked 3-indolylmethyl | —CH$_3$ | Trp—CH$_3$ |
| 4-methoxyphenylmethyl | —Bn | (Tyr—OCH$_3$)—Bn |
| phenylethyl | —CH$_3$ | (Phet)—CH$_3$ |

Formula 6

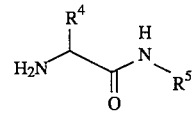

where R$^5$ is —CH—(R$^6$)—C(O)NH$_2$

| R$^4$ | R$^6$ | Name |
|---|---|---|
| hydrogen | methyl | Gly—Ala—NH$_2$ |
| methyl | 2-butyl | Ala—Ile—NH$_2$ |
| 2-propyl | 2-methylpropyl | Val—Leu—NH$_2$ |
| 2-butyl | hydrogen | Leu—Gly—NH$_2$ |
| 2-methylpropyl | 2-propyl | Ile—Val—NH$_2$ |
| blocked 4-aminobutyl | 2-methylpropyl | Lys—Leu—NH$_2$ |
| blocked 3-guanylpropyl | methyl | Arg—Ala—NH$_2$ |
| blocked 4-imidazoylmethyl | 2-butyl | His—Ile—NH$_2$ |
| benzyl | 2-methylpropyl | Phe—Leu—NH$_2$ |
| blocked 4-hydroxyphenylmethyl | hydrogen | Tyr—Gly—NH$_2$ |

-continued

Formula 6

$$H_2N-\underset{R^4}{C}H-\underset{O}{C}-\underset{H}{N}-R^5$$

where $R^5$ is $-CH-(R^6)-C(O)NH_2$

| $R^4$ | $R^6$ | Name |
|---|---|---|
| blocked 3-indolylmethyl | 2-propyl | Trp—Val—NH$_2$ |
| 4-methoxyphenylmethyl | 2-methylpropyl | (Tyr—OCH$_3$)—Leu—NH$_2$ |
| phenylethyl | methyl | (Phet)—Ala—NH$_2$ |
| hydrogen | blocked 4-aminobutyl | Gly—Lys—NH$_2$ |
| methyl | blocked 3-guanylpropyl | Ala—Arg—NH$_2$ |
| 2-propyl | 2-imidazoylmethyl | Val—His—NH$_2$ |
| 2-butyl | blocked 4-aminobutyl | Leu—Lys—NH$_2$ |
| 2-methylpropyl | blocked 3-guanylpropyl | Ile—Arg—NH$_2$ |
| blocked 4-aminobutyl | 2-imidazoylmethyl | Lys—His—NH$_2$ |
| blocked 3-guanylpropyl | blocked 4-aminobutyl | Arg—Lys—NH$_2$ |
| blocked 4-imidazoylmethyl | blocked 3-guanylpropyl | His—Arg—NH$_2$ |
| benzyl | 2-imidazoylmethyl | Phe—His—NH$_2$ |
| blocked 4-hydroxyphenylmethyl | blocked 4-aminobutyl | Tyr—Lys—NH$_2$ |
| blocked 3-indolylmethyl | blocked 3-guanylpropyl | Trp—Arg—NH$_2$ |
| 4-methoxyphenylmethyl | 2-imidazoylmethyl | (Tyr—OCH$_3$)—His—NH$_2$ |
| phenylethyl | blocked 4-aminobutyl | (Phet)—Lys—NH$_2$ |
| hydrogen | thiolmethyl | Gly—Cys—NH$_2$ |
| methyl | methylthioethyl | Ala—Met—NH$_2$ |
| 2-propyl | hydroxymethyl | Val—Ser—NH$_2$ |
| 2-butyl | 1-hydroxyethyl | Leu—Thr—NH$_2$ |
| 2-methylpropyl | thiolmethyl | Ile—Cys—NH$_2$ |
| blocked 4-aminobutyl | methylthioethyl | Lys—Met—NH$_2$ |
| blocked 3-guanylpropyl | hydroxymethyl | Arg—Ser—NH$_2$ |
| blocked 4-imidazoylmethyl | 1-hydroxyethyl | His—Thr—NH$_2$ |
| benzyl | thiolmethyl | Phe—Cys—NH$_2$ |
| blocked 4-hydroxyphenylmethyl | methylthioethyl | Tyr—Met—NH$_2$ |
| blocked 3-indolylmethyl | hydroxymethyl | Trp—Ser—NH$_2$ |
| 4-methoxyphenylmethyl | 1-hydroxyethyl | (Tyr—OCH$_3$)—Thr—NH$_2$ |
| phenylethyl | hydroxymethyl | (Phet)—Ser—NH$_2$ |
| blocked 3-guanylpropyl | methylthioethyl | Arg—Met—NH$_2$ |

EXAMPLE 23

Determination of Fibroblast Collagenase (HFC) Inhibition

Starting Materials and Reagents

Pro-HFC was purified from the harvest media of human gingival fibroblasts following procedures described in Birkedal-Hansen, H. *Methods Enzymol.* 1987, 144, 140–171.

The HFC used in the assays was either zymogen that had undergone spontaneous activation, or zymogen that had been activated by treatment with 100 μg/mL of trypsin for 15 min at 23° C., followed by the addition of a 4-fold excess of soybean trypsin inhibitor.

Kinetic Measurements

Assays were performed in 50 mM Tricine, 0.2M NaCl, 10 mM CaCl$_2$, pH 7.5 containing 5% methanol once the substrate and inhibitor were diluted into it. The buffer was freed from adventitious metal ions by extraction with dithizone in carbon tetrachloride (Holmquist, B. *Methods Enzymol.* 1988, 158, 6–10). Stock solutions of inhibitors were prepared in 100% methanol. The concentrations of the stock solutions of sulfhydryl-containing inhibitors were determined spectrophotometrically by reaction with Ellman's reagent (Riddles, P. W.; Blakeley, R. L.; Zerner, B. *Anal. Biochem.* 1979, 94, 75–81) immediately prior to their use. Stock solutions of the substrate were prepared in 50% aqueous methanol at a concentration of 0.2 mM.

The assay method used was based on the hydrolysis of DNP-Pro-Leu-Ala-Leu-Trp-Ala-Arg at 24° C. (Netzel-Arnett, S.; Mallya, S. K.; Nagase, H.; Birkedal-Hansen, H.; Van Wart, H. E. *Anal. Biochem.* 1991, 195, 86–92). The fluorescence changes were monitored with a Perkin-Elmer Model LS-5 fluorometer using an excitation wavelength of 280 nm and an emission wavelength of 360 nm. The substrate concentration used in the assays was either 5 μM or 10 μM. The inhibitor was diluted into the assays using 100% methanol, and controls substituted an equal volume of methanol so that the final methanol concentration from inhibitor and substrate dilutions in all assays was 5%. For each assay, the enzyme and inhibitor were incubated in the assay buffer at 24° C. for 30 min, then the substrate was added and the rate of hydrolysis was measured by monitoring the increase in fluorescence intensity at 360 nm over a period of approximately 30 min. The inhibition results are expressed as the inhibitor concentration that produced 50% inhibition (IC$_{50}$) of activity at the substrate concentration used.

Representative compounds of the present invention exhibited inhibition of HFC when tested by this method.

EXAMPLE 23

Determination of Neutrophil Collagenase (NHC) Inhibition

Starting Materials and Reagents

HNC (58 kDa active form) was isolated from human buffy coats following procedures described in Mookhtiar, K. A.; Van Wart, H. E. *Biochemistry* 1990, 29, 10620–10627.

HNC was isolated in active form and no additional treatments were performed before use in assays.

Kinetic Measurements

The preparation of enzyme, inhibitor and substrate solutions; and the assay method were performed using the procedure described in Example 21 (Kinetic Measurements Section).

Representative compounds of the present invention exhibited inhibition of HNC when tested by this method.

EXAMPLE 24

Determination of Fibroblast Gelatinase (HFG) Inhibition

Starting Materials and Reagents

Pro-HFG was purified from the harvest media of human gingival fibroblasts following procedures described in Birkedal-Hansen, H. *Methods Enzymol.* 1987, 144, 140–171.

Spontaneously activated HFG was used without additional treatment.

Kinetic Measurements

The preparation of enzyme, inhibitor and substrate solutions; and the assay method were performed using the procedure described in Example 21 (Kinetic Measurements Section).

Representative compounds of the present invention exhibited inhibition of HFG when tested by this method.

EXAMPLE 25

Determination of Neutrophil Gelatinase (HNG) Inhibition

Starting Materials and Reagents

Pro-HNG was isolated from human buffy coats following procedures described in Mookhtiar, K. A.; Van Wart, H. E. *Biochemistry* 1990, 29, 10620– 10627.

Spontaneously activated HNG was used without additional treatment.

Kinetic Measurements

The preparation of enzyme, inhibitor and substrate solutions; and the assay method were performed using the procedure described in Example 21 (Kinetic Measurements Section).

Representative compounds of the present invention exhibited inhibition of HNG when tested by this method.

EXAMPLE 26

Determination of Stromelysin (HFS) Inhibition

Starting Materials and Reagents

Pro-HFS was isolated from the culture medium of human rheumatoid synovial cells stimulated with rabbit macrophage-conditioned medium by affinity chromatography using sheep anti-HFS IgG coupled to Affi-Gel 10 following procedures described in Ito, A.; Nagase, H. *Arch. Biochem. Biophys.* 1988, 267, 211–216.

Pro-HFS was activated by treatment with 1 mM p-aminophenylmercuric acetate (APMA) for 24 hr at 37° C. to give a mixture of 45 and 28 kDa species, which are known to have indistinguishable specific activities and specificities (following procedures described in Okada, Y.; Nagase, H.; Harris, E. D., Jr. *J. Biol. Chem.* 1986, 261, 14245–14255). HFS was separated from the APMA by chromatography over Sephacryl S-200 and it was stored at 4° C.

Kinetic Measurements

The preparation of enzyme, inhibitor and substrate solutions; and the assay method were performed using the procedure described in Example 21 (Kinetic Measurements Section).

Representative compounds of the present invention exhibited inhibition of HFS when tested by this method.

EXAMPLE 27

Determination of Matrilysin (PUMP) Inhibition

Starting Materials and Reagents

Pro-PUMP was isolated from Chinese hamster ovary cells carrying an amplified pro-PUMP cDNA (Yuan et al., in preparation). Briefly, conditioned medium was collected from cells grown in serum-free medium, concentrated, applied to a blue-Sepharose column and eluted in 20 mM Tris, 5 mM $CaCl_2$, 0.05% Brij-35, pH 7.4 with a 0–1.5M NaCl gradient. Fractions containing pro-PUMP were pooled and loaded directly onto a zinc-Sepharose column, and eluted with a 0–600 mM glycine gradient. The final purification was achieved by chromatography over S-Sepharose using a linear 0–1M NaCl gradient for elution.

Pro-PUMP was activated by treatment with 1 mM PCMB for 2 hr at 37° C. and then dialyzed against 50 mM Tricine, 0.2M NaCl, 10 mM $CaCl_2$, 50 µM $ZnSO_4$, 0.05% Brij-35, pH 7.5 to remove all traces of PCMB.

Kinetic Measurements

The preparation of enzyme, inhibitor and substrate solutions; and the assay method were performed using the procedure described in Example 21 (Kinetic Measurements Section).

Representative compounds of the present invention exhibited inhibition of PUMP when tested by this method.

EXAMPLE 28

Capsule Formulation

This example illustrates the preparation of a representative pharmaceutical formulation for oral administration containing an active compound of Formula I, e.g., $HS(CH_2)_2$—(S-D-Leu)-Phe-NHMe.

| Ingredients | Quantity (mg/capsule) |
|---|---|
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Reaction Schemes A, B and C, and Examples 1–22 can be used as the active compound in the preparation of the orally administrable formulations of this example.

EXAMPLE 29

Oral Formulation

This example illustrates the preparation of a representative pharmaceutical formulation containing an active compound of Formula I, e.g., $HSCH_2(R)CHMe$-(S-D-Leu)-Phe-NHMe.

An suspension for oral administration is prepared having the following composition:

| Ingredients | Quantity |
|---|---|
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Other compounds of Formula I, such as those prepared in accordance with Reaction Schemes A, B and C, and Examples 1–22 can be used as the active compound in the preparation of the orally administrable formulations of this example.

EXAMPLE 30

Tablet Formulation

This example illustrates the preparation of a representative pharmaceutical formulation containing an active compound of Formula I, e.g., HS(R)CHMeCH$_2$-(S-D-Leu)-Phe-NHMe.

A tablet for oral administration is prepared having the following composition:

| Ingredients | Quantity (mg/tablet) |
| --- | --- |
| Active compound | 400 |
| corn starch | 50 |
| lactose | 145 |
| magnesium stearate | 5 |

The above ingredients are mixed intimately and pressed into single scored tablets.

Other compounds of Formula I, such as those prepared in accordance with Reaction Schemes A, B and C, and Examples 1–22 can be used as the active compound in the preparation of the tablet formulations of this example.

EXAMPLE 31

Injectable Formulation

This example illustrates the preparation of a representative pharmaceutical formulation containing an active compound of Formula I, e.g., HS(CH$_2$)$_2$—(S-D-Leu)-Phe-NHMe.

An injectable preparation is prepared having the following composition:

| Ingredients | Quantity |
| --- | --- |
| Active compound | 0.2 g |
| water (distilled, sterile) | q.s. to 20.0 mL |

Other compounds of Formula I, such as those prepared in accordance with Reaction Schemes A, B and C, and Examples 1–22 can be used as the active compound in the preparation of the injection administrable formulations of this example.

EXAMPLE 32

Suppository Formulation

This example illustrates the preparation of a representative pharmaceutical formulation containing an active compound of Formula I, e.g., HSCH$_2$(R)CHMe-(S-D-Leu)-Phe-NHMe.

A suppository totalling 2.5 grams is prepared having the following composition:

| Ingredients | Quantity |
| --- | --- |
| Active compound | 500 mg |
| witepsol H-15* | q.s. to 2.5 g |

(*triglycerides of saturated vegatable fatty acid; a product of Riches-Nelson, Inc., New York, N.Y.).

Other compounds of Formula I, such as those prepared in accordance with Reaction Schemes A, B and C, and Examples 1–22 can be used as the active compound in the preparation of the suppository formulations of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula, $$HS-CH(R^1)-(CH_2)_n-S-CH(R^2)-CH(R^3)-C(O)-NH-CH(R^4)-C(O)-NH(R^5)$$

wherein:

n is 0 or 1;

$R^1$ is selected from the group consisting of hydrogen, lower alkyl, amino lower alkyl, carbamoyl lower alkyl, PhtN(lower alkyl), TsNH(lower alkyl); and $R^2$ is selected from the group consisting of hydrogen, lower alkyl, amino lower alkyl, carbamoyl lower alkyl, PhtN(lower alkyl), TsNH(lower alkyl); or $R^1$ and $R^2$ together are —CH$_2$—CH$_2$—CH$_2$—;

$R^3$ is selected from the group consisting of hydrogen, lower alkyl, aralkyl and heteroaralkyl; and $R^4$ is selected from the group consisting of hydrogen, lower alkyl, amino lower-alkyl, guanyl lower-alkyl, imidazoylalkyl, aralkyl and 2-indolylmethyl; and $R^5$ is selected from the group consisting of lower alkyl, aralkyl and —CH($R^6$)—C(O)NH$_2$, wherein $R^6$ is selected from the group consisting of hydrogen, lower-alkyl, amino lower-alkyl, guanyl lower-alkyl, imidazoylalkyl, hydroxymethyl, 1-hydroxyethyl, mercapto lower-alkyl, and methylthio lower-alkyl;

or a pharmaceutically acceptable ester, ether or salt thereof.

2. The compound of claim 1 wherein n is 0.

3. The compound of claim 2 wherein $R^3$ is lower-alkyl.

4. The compound of claim 3 wherein the carbon that is the point of attachment for $R^3$ is in the D-configuration.

5. The compound of claim 4 wherein $R^3$ is 2-methylpropyl.

6. The compound of claim 5 wherein $R^4$ is aralkyl.

7. The compound of claim 6 wherein $R^4$ is phenylmethyl.

8. The compound of claim 6 wherein $R^5$ is lower-alkyl.

9. The compound of claim 8 wherein $R^5$ is methyl.

10. The compound of claim 6 wherein $R^5$ is aralkyl.

11. The compound of claim 10 wherein $R^5$ is phenylmethyl.

12. The compound of claim 6 wherein $R^5$ is —CH($R^6$)—C(O)NH$_2$.

13. The compound of claim 12 wherein $R^6$ is lower alkyl.

14. The compound of claim 12 wherein $R^6$ is methyl.

15. The compound of claim 12 wherein $R^1$ and $R^2$ together are —CH$_2$—CH$_2$—CH$_2$.

16. The compound of claim 12 wherein $R^2$ is hydrogen.

17. The compound of claim 16 wherein $R^1$ is selected from the group consisting of hydrogen, lower alkyl and PhtN(lower alkyl).

18. The compound of claim 17 wherein $R^1$ is hydrogen.

19. The compound of claim 17 wherein $R^1$ is methyl.

20. The compound of claim 17 wherein $R^1$ is PhtNBu.

21. The compound of claim 17 wherein $R^1$ is PhtNEt.

22. The compound of claim 1 wherein n is 1.

23. The compound of claim 22 wherein $R^3$ is lower-alkyl.

24. The compound of claim 23 wherein the carbon that is the point of attachment for $R^3$ is in the D-configuration.

25. The compound of claim 24 wherein $R^3$ is 2-methylpropyl.

26. The compound of claim 25 wherein $R^4$ is aralkyl.

27. The compound of claim 26 wherein $R^4$ is phenylmethyl.

28. The compound of claim 26 wherein $R^5$ is lower alkyl.

29. The compound of claim 28 wherein $R^5$ is methyl.

30. The compound of claim 26 wherein $R^5$ is aralkyl.

31. The compound of claim 30 wherein $R^5$ is phenylmethyl.

32. The compound of claim 26 wherein $R^5$ is —CH($R^6$)—C(O)NH$_2$.

33. The compound of claim 32 wherein $R^6$ is lower alkyl.

34. The compound of claim 33 wherein $R^6$ is methyl.

35. The compound of claim 1 that is HS(CH$_3$)$_2$—(S-D-Leu)-Phe-NHMe.

36. The compound of claim 1 that is HS(S)CHMeCH$_2$—(S-D-Leu)-Phe-NHMe.

37. The compound of claim 1 that is HS(S)CH(PhtN-Bu)CH$_2$—(S-D-Leu)-Phe-NHMe.

38. The compound of claim 1 that is HS(S)CH(PhtNEt)CH$_2$—(S-D-Leu)-Phe-NHMe.

39. The compound of claim 1 that is HS(1,2-cyclopentyl)(S-D-Leu)-Phe-NHMe.

40. A compound of the formula,

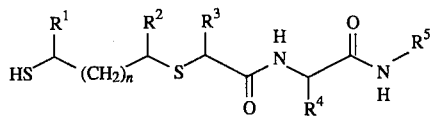

wherein:

n is 0 or 1;

$R^1$ is selected from the group consisting of hydrogen, lower alkyl, amino lower alkyl, carbamoyl lower alkyl, PhtN(lower alkyl), TsNH(lower alkyl); and $R^2$ is selected from the group consisting of hydrogen, lower alkyl, amino lower alkyl, carbamoyl lower alkyl, PhtN(lower alkyl), TsNH(lower alkyl); or $R^1$ and $R^2$ together are —CH$_2$—CH$_2$—CH$_2$—;

$R^3$ is selected from the group consisting of hydrogen, lower alkyl, aralkyl and heteroaralkyl; and $R^4$ is selected from the group consisting of hydrogen, lower alkyl, amino lower-alkyl, guanyl lower-alkyl, imidazoylalkyl, aralkyl and 2-indolylmethyl; and $R^5$ is selected from the group consisting of lower alkyl, aralkyl and —CH($R^6$)—C(O)NH$_2$, wherein $R^6$ is selected from the group consisting of hydrogen, lower-alkyl, amino lower-alkyl, guanyl lower-alkyl, imidazoylalkyl, hydroxymethyl, 1-hydroxyethyl, mercapto lower-alkyl, and methylthio lower-alkyl;

or a pharmaceutically acceptable ester, ether or salt thereof used for inhibiting metalloproteinase activity.

41. A pharmaceutical composition comprising a compound of the formula

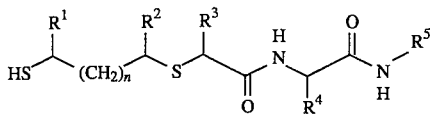

wherein:

n is 0 or 1;

$R^1$ is selected from the group consisting of hydrogen, lower alkyl, amino lower alkyl, carbamoyl lower alkyl, PhtN(lower alkyl), TsNH(lower alkyl); and $R^2$ is selected from the group consisting of hydrogen, lower alkyl, amino lower alkyl, carbamoyl lower alkyl, PhtN(lower alkyl), TsNH(lower alkyl); or $R^1$ and $R^2$ together are —CH$_2$—CH$_2$—CH$_2$—;

$R^3$ is selected from the group consisting of hydrogen, lower alkyl, aralkyl and heteroaralkyl; and $R^4$ is selected from the group consisting of hydrogen, lower alkyl, amino lower-alkyl, guanyl lower-alkyl, imidazoylalkyl, aralkyl and 2-indolylmethyl; and $R^5$ is selected from the group consisting of lower alkyl, aralkyl and —CH($R^6$)—C(O)NH$_2$, wherein $R^6$ is selected from the group consisting of hydrogen, lower-alkyl, amino lower-alkyl, guanyl lower-alkyl, imidazoylalkyl, hydroxymethyl, 1-hydroxyethyl, mercapto lower-alkyl, and methylthio lower-alkyl;

or a pharmaceutically acceptable ester, ether or salt thereof and pharmaceutically acceptable excipients useful for modulating physiological functions or treating diseases and disease conditions associated with matrix metalloproteinase modulation.

* * * * *

UNITED STATES PATENT AND TRADEMARK OFFICE
CERTIFICATE OF CORRECTION

PATENT NO. : 5,455,262
DATED : October 3, 1995
INVENTOR(S) : Martin A. Schwartz and Harold Van Wart It is certified that error appears in the above-identified patent and that said Letters Patent is hereby corrected as shown below:

In column 105, Claim 15, line 2, after "are" should read "$-CH_2-CH_2-CH_2-$."

In column 105, Claim 35, lines 1 and 2, after "is" should read "$HS(CH_2)_2-(S-D-Leu)-Phe-NHMe$.".

Signed and Sealed this

Nineteenth Day of March, 1996

Attest:

BRUCE LEHMAN

*Attesting Officer*   *Commissioner of Patents and Trademarks*